(12) United States Patent
Yu et al.

(10) Patent No.: US 11,795,579 B2
(45) Date of Patent: Oct. 24, 2023

(54) YEAST DISPLAY OF PROTEINS IN THE PERIPLASMIC SPACE

(71) Applicant: Abalone Bio, Inc., Richmond, CA (US)

(72) Inventors: Richard Yu, Richmond, CA (US); Carlos Gustavo Pesce, Richmond, CA (US); Rodrigo Baltanas, Richmond, CA (US); Brett Robison, Richmond, CA (US)

(73) Assignee: Abalone Bio, Inc., Richmond, CA (US)

( * ) Notice: Subject to any disclaimer, the term of this patent is extended or adjusted under 35 U.S.C. 154(b) by 456 days.

(21) Appl. No.: 16/771,128

(22) PCT Filed: Dec. 10, 2018

(86) PCT No.: PCT/US2018/064775
§ 371 (c)(1),
(2) Date: Jun. 9, 2020

(87) PCT Pub. No.: WO2019/118362
PCT Pub. Date: Jun. 20, 2019

(65) Prior Publication Data
US 2021/0198806 A1    Jul. 1, 2021

Related U.S. Application Data

(60) Provisional application No. 62/597,388, filed on Dec. 11, 2017.

(51) Int. Cl.
*C40B 40/02* (2006.01)
*C07K 16/28* (2006.01)
(Continued)

(52) U.S. Cl.
CPC .............. *C40B 40/02* (2013.01); *C07K 16/00* (2013.01); *C07K 16/28* (2013.01);
(Continued)

(58) Field of Classification Search
None
See application file for complete search history.

(56) References Cited

U.S. PATENT DOCUMENTS

| 4,946,783 A | 8/1990 | Beckwith et al. |
| 5,210,019 A | 5/1993 | Margalit |

(Continued)

FOREIGN PATENT DOCUMENTS

| AU | 2004204462 B2 | 3/2012 |
| AU | 2018383600 A1 | 6/2020 |

(Continued)

OTHER PUBLICATIONS

Arai, R. et al. (2001). "Design of the Linkers Which Effectively Separate Domains of a Bifunctional Fusion Protein," Protein Eng. 14(8):529-532.

(Continued)

*Primary Examiner* — Christian C Boesen
(74) *Attorney, Agent, or Firm* — MORRISON & FOERSTER LLP

(57) ABSTRACT

Compositions and methods for displaying antibodies in the periplasmic space of yeast cells are disclosed. In particular, antibodies are linked to a cell membrane-spanning transmembrane domain, a cell-membrane associated protein domain that is on the external face of the yeast cell membrane, a protein that binds to the inner face of the yeast cell wall, or a periplasmic protein in order to display the antibodies in the yeast periplasmic space. In addition, a target protein of interest can be coexpressed in yeast such that it is localized to the plasma membrane or periplasmic space and accessible to binding by displayed antibodies. The disclosure further relates to high-throughput screening of antibody libraries using yeast cell periplasmic display.

12 Claims, 12 Drawing Sheets

(51) Int. Cl.
  *C12N 15/10* (2006.01)
  *C40B 30/04* (2006.01)
  *C40B 30/06* (2006.01)
  *C07K 16/00* (2006.01)
(52) U.S. Cl.
  CPC .......... *C12N 15/1037* (2013.01); *C40B 30/04* (2013.01); *C40B 30/06* (2013.01)

(56) References Cited

U.S. PATENT DOCUMENTS

| | | | |
|---|---|---|---|
| 7,435,804 | B2 | 10/2008 | Kordyum et al. |
| 7,611,866 | B2 | 11/2009 | Georgiou et al. |
| 8,722,584 | B2 | 5/2014 | Delisa et al. |
| 8,841,238 | B2 | 9/2014 | Martineau et al. |
| 8,987,173 | B2 | 3/2015 | Delisa et al. |
| 9,244,070 | B2 | 1/2016 | Georgiou et al. |
| 9,934,344 | B2 | 4/2018 | Liu et al. |
| 10,725,037 | B2 | 7/2020 | Georgiou et al. |
| 2005/0147962 | A1 | 7/2005 | Wagstrom et al. |
| 2005/0202403 | A1 | 9/2005 | Fowlkes et al. |
| 2006/0029947 | A1 | 2/2006 | Georgiou et al. |
| 2006/0121565 | A1 | 6/2006 | Jonson et al. |
| 2007/0099267 | A1 | 5/2007 | Harvey et al. |
| 2011/0076752 | A1 | 3/2011 | Wu et al. |
| 2014/0235482 | A1 | 8/2014 | Georgiou et al. |
| 2015/0316561 | A1* | 11/2015 | Zhang ................ C07K 16/2866 506/9 |
| 2016/0060642 | A1 | 3/2016 | Trowell et al. |
| 2018/0119075 | A1 | 5/2018 | Vernhet et al. |
| 2020/0157529 | A1 | 5/2020 | Weiner et al. |

FOREIGN PATENT DOCUMENTS

| | | |
|---|---|---|
| CA | 2528202 C | 1/2012 |
| CA | 2645194 C | 2/2012 |
| CA | 2501188 C | 5/2012 |
| CA | 2475929 C | 1/2013 |
| CA | 2964910 C | 1/2018 |
| EA | 013225 B1 | 4/2010 |
| EP | 0300035 B1 | 5/1995 |
| EP | 1745066 A2 | 1/2007 |
| EP | 3526330 A1 | 8/2019 |
| EP | 3286315 B1 | 5/2021 |
| KR | 102048037 B1 | 11/2013 |
| WO | 2004061104 A2 | 7/2004 |
| WO | 2004061104 A3 | 11/2004 |
| WO | 2005095988 A2 | 10/2005 |
| WO | 2005095988 A3 | 3/2006 |
| WO | 2006023248 A2 | 3/2006 |
| WO | 2006023248 A3 | 5/2009 |
| WO | 2009111183 A1 | 9/2009 |
| WO | 2013023251 A1 | 2/2013 |
| WO | 2014035693 A2 | 3/2014 |
| WO | 2014035693 A3 | 4/2014 |
| WO | 2016174515 A1 | 11/2016 |
| WO | 2017087811 A1 | 5/2017 |
| WO | 2018232282 A1 | 12/2018 |
| WO | 2019118362 A1 | 6/2019 |
| WO | 2019231403 A1 | 12/2019 |

OTHER PUBLICATIONS

Armaleo, D. et al. (1990). Biolistic Nuclear Transformation of *Saccharomyces cerevisiae* and Other Fungi, Curr. Genet. 17(2):97-103.
Avery, O.T. et al. (May 1995). "Studies on the Chemical Nature of the Substance Inducing Transformation of Pneumococcal Types," Mol. Med. 1(4):344-365.
Baranick, B.T. et al, (Mar. 25, 2008), "Splicing Mediated the Activity of Four Putative Cellular Internal Ribsome Entry Sites," Proc. Natl. Acad. Sci. USA. 105(12):4733-4738.
Bert, A.G. et al. (2006). "Assessing IRES Activity in the HIF-1α and Other Cellular 5' UTRs," RNA 12(6): 1074-1083.
Boder, E.T. et al. (Jun. 1997). "Yeast Surface Display for Screening Combinatorial Polypeptide Libraries," Nat. Biotechnol. 15:553-557.
Bose, J.L. (2016). "Chemical and UV mutagenesis," Methods Mol. Biol. 1373:111-115.
Bupp, K. et al. (Mar. 2002). "Altering Retroviral Tropism Using a Random-Display Envelope Library," Mol. Ther. 5(3):329-335.
Cherf, G.M. et al. (2015). "Applications of Yeast Surface Display for Protein Engineering," Methods Mol. Biol. 1319:155-175, 21 pages.
Cox, J.C. et al. (2001). "Automated Selection of Anti-Protein Aptamers," Bioorg Med Chem. 9(10): 2525-2531.
Cox, J.C, et al. (2002). "Automated Selection of Aptamers Against Protein Targets Translated in Vitro: From Gene to Aptamer," Nucleic Acids Res. 30(20); e108, 14 pages.
Crasto, C.J. et al. (2000). "Linker: A Program to Generate Linker Sequences for Fusion Protein," Protein Eng. 13 (5):309-312.
Cumber, A.J. et al. (Jul. 1992). "Comparative Stabilities In Vitro and In Vivo of a Recombinant Mouse Antibody FvCys Fragment and a bisFvCys Conjugate," J Immunology 149(1):120-126.
Dalbie-McFarland, G. et al. (Nov. 1982). "Oligonucleotide-Directed Mutagenesis as a General and Powerful Method for Studies of Protein Function," Proc. Natl. Acad. Sci. USA 79:6409-6413.
Desmet, J. et al. (Oct. 30, 2014). "Structural Basis of IL-23 Antagonism by an Alphabody Protein Scaffold," Nature Communications 5:5237, 12 pages.
Dobrikova, E. et al. (Dec. 9, 2003). "Activity of a Type 1 Picornavirus Internal Ribosomal Entry Site is Determined by Sequences Within 3' Nontranslated Region," Proc. Natl. Acad. Sci. 100(25):15125-15130.
Ehrlich, P.H. et al. (Aug. 19, 1980). "Isolation of An Active Heavy-Chain Variable Domain From a Homogeneous Rabbit Antibody By Cathepsin B Digestion of the Aminoethylated Heavy Chain," Biochem 19(17):4091-4096.
Furler, S. et ai. (2001), "Recombinant AAV Vectors Containing the Foot andMouth Disease Virus 2A Sequence Confer EfficientBicistronic Gene Expression in Cultured Cells and RatSubstantia Nigra Neurons," Gene Ther. 8 (11):864-873.
Garlapati, S. et al. (Jan. 20, 2004). "Identification of a Novel Internal Ribosome Entry Site inGiardiavirus That Extends to Both Sides of the Initiation Codon," Biol. Chem. 279(5):3389-3397.
George, R.A. et al. (2002). "An Analysis of Protein Domain Linkers: Their Classification and Role in Protein Folding," Protein Eng. 15(11):871-879.
Gietz, R.D. et al. (2007). "High Efficiency DNA Transformation of *Saccharomyces cerevisiae* with theLIAc/SS-DNA/PEG Method," Nat. Protoc. 2(1):38-41.
Grabulovski, D. et al. (Feb. 2007). "A Novel, Non-immunogenic Fyn SH3-derived Binding Protein with Tumor Vascular Targeting Properties," J. Biol. Chem. 282 (5):3196-3204.
Graham, F.L. et al. (Apr. 1973). "A New Technique for the Assay of Infectivity of Human Adenovirus 5 DNA," Virology 52(2):456-467.
Grussenmeyer, T. et al. (Dec. 1985). "Complexes of Polyoma Virus Medium T Antigen and Cellular Proteins," Proc. Natl. Acad. Sci. USA 82:7952-7954.
Hanes, J. et al. (May 1997). "In vitro Selection and Evolution of Functional Proteins by Using Ribosome Display," PNAS USA 94:4937-4942.
Hinnen, A. et al. (Apr. 1978). Transformation of Yeast, Proc. Natl. Acad. Sci. USA 75(4):1929-1933.
Hopp, T.P. et al. (1988). "A Short Polypeptide Marker Sequence Useful For Recombinant Protein Identification and Purification," BioTechnoiogy 6:1204-1210.
Huston, J.R. et al. (Aug. 1988). "Protein Engineering of Antibody Binding Sites: Recovery of Specific Activity in an Anti-Digoxin Single-Chain Fv Analogue Produced in *Escherichia coli*," Proc. Natl. Acad. Sci. U.S.A. 85(16)5879-5883.
Inbar, D. et al. (Sep. 1972). "Localization of Antibody-Combining Sites within the Variable Portions of Heavy and Light Chains," Proc. Natl. Acad. Sci. USA 69:2659-2662.
Innis, M.A. et al. (1990). Optimization of PCRs, in PCR Protocols: A Guide to Methods and Applications, 11 pages.

(56) References Cited

OTHER PUBLICATIONS

International Preliminary Report on Patentability dated Jun. 25, 2020, for Patent Application No. PCT/US18/64775, filed Dec. 10, 2018, 14 pages.
International Search Report and Written Opinion of the International Searching Authority dated Apr. 8, 2019, for Patent Application No. PCT/US18/64775, filed Dec. 10, 2018, 22 pages.
Ito, H. et al. (Jan. 1983). "Transformation of Intact Yeast Cells Treated with Alkall Cations," J. Bacteriol. 153 (1):163-168.
Jang, S.K. et al. (Apr. 1989). "Initiation of Protein Synthesis by Internal Entry of Ribosomes into the 5' Nontranslated Region of Encephalomyocarditis Virus RNA In Vivo," J Virol. 63(4):1651-1660.
Jay, E. et al. (May 25, 1984). "Chemical Synthesis of a Biologically Active Gene for Human immune interferon-γ," J. Biol. Chem. 259(10):6311-6317.
Kaufman, R.J. et al. (1991). "Improved Vectors for Stable Expression of Foreign genes in Mammalian Cells by use of the Untranslated Leader Sequence From EMC Virus," Nuc. Acids Res. 19(16):4485-4490.
Kawai, S. et al., (Nov./Dec. 2010). "Transformation of *Saccharomyces cerevisiae* and Other Fungi," Bioeng. Bugs. 1(6):395-403.
Kegler-Ebo, D.M. et al. (1994). "Codon Cassette Mutagenesis: A General Method to Insert or Replace Individual Codons by Using Universal Mutagenic Cassettes," Nucleic Acids Research. 22 (9):1593-1599.
Kim, J.H. et al. (Apr. 2011). "High Cleavage Efficiency of a 2A Peptide Derived from Porcine Teschovirus-1 in Human Cell Lines, Zebrafish and Mice," PLOS One 6(4):e18556, 8 pages.
Kobayashi, M. et al. (Sep. 1996). "Improved Dicistronic mRNA Expression Vectors for Efficient Selection of Transfectants Highly Expressing Foreign Genes," BioTechniques 21(3):398-402.
Koide, A. et al. (2007). "Monobodies. Antibody Mimics bases on the Scaffold of the Fibronectin Type III Domain," Methods Mol. Biol. 352:95-109.
Krah, S. et al. (2016). "Single-Domain Antibodies for Biomedical Applications," Immunopharmacoi. Immunotoxicol. 38 (1):21-28, 23 pages.
Krehenbrink, M. et al. (2008, e-pub. Sep. 16, 2008). "Artificial Binding Proteins (Affitins) as Probes for Conformational Changes in Secretin PulD," J. Mol. Biol. 383(5):1058-1068.
Lu, Z. et al. (Apr. 1995). "Expression of Thioredoxin Random Peptide Libraries on the scherichia coil Cell Surface as FunctionalFusions to Flagellin: A System Designed for Exploring Protein-Protein Interactions," Biotechnology 13:366-372.
Lyu, Y. et al. (2016)/ Generating Cell Targeting Aptamers for Nanotheranostics Using Cell-SELEX, Theranostics 6 (9):1440-1452.
Madzak, C. (2015). "Yarrowia Lipolytica: Recent Achievements in Heterologous Protein Expression and Pathway Engineering," Appl. Microbiol. Biotechnol. 99(11):4559-4577.
Martin, M.M. et al. (Dec. 2003). "Translation of the Human Angiotensin II Type 1 Receptor mRNA is Mediated by a Highly Efficient internal Ribosome Entry Site," Mol. Ceil Endocrinol. 212:51-61.
Martineau, Y. et al. (Sep. 2004). "Internal Ribosome Entry Site Structural Motifs Conserved Among Mammalian Fibroblast Growth Factor 1 Alternatively Spliced mRNAs," Mol. Cell. Biol. 24(17):7622-7635.
McCullum, E.O. et al. (2010). "Random Mutagenesis by Error-Prone PCR," Chapter 7 in Methods Mol. Biol. 634:103-109.
Mosser, D.D. et al. (Jan. 1997). "Use of a Dicistronic Expression Cassette Encoding the Green Fluorescent Protein for the Screening and Selection of Cells Expressing Inducible Gene Products," BioTechniques 22(1):150-161.
Muteeb, G. et al. (2010). "Random Mutagenesis Using a Mutator Strain," Chapter 29 in Methods Mol. Biol. 634:411-419.

Nambair, K.P. et al. (Mar. 23, 1984). "Total Synthesis and Cloning of a Gene Coding for the Ribonuclease S Protein," Science 223:1299-1301.
Nguyen, J.T. et al. (Jun. 12, 2000). "improving SH3 Domain Ligand Selectivity Using a Non-Natural Scaffold," Chem. Biol. 7(7):463-473.
Nilsson, B. et al. (1985). "Immobilization and Purification of Enzymes with Staphylococcal Protein A Gene Fusion Vectors," EMBO J. 4(4):1075-1080.
Nygren, P-A. (2008). "Alternative Binding Proteins: Affibody Binding Proteins Developed From A Small Three-Helix Bundles Scaffold," FEBS J. 275(11):2668-2676.
Pack, P. et al. (Feb. 18, 1992). "Miniantibodies: Use of Amphipathic Helices to Produce functional, Flexibly Linked Dimeric FV Fragments with High Avidity in *Escherichia coli*," Biochem. 31(61:1579-1584.
Pedersen, S.K. et al. (2002). "Human Insulin-Like Growth factor II Leader 2 Mediates Internal Initiation of Translation," Biochem. J. 363:37-44.
Provost, E. et al. (2007). "Viral 2A Peptides Allow Expression of Multiple Proteins From a Single ORF in Transgenic Zebrafish Embryos," Genesis 45(10):625-629.
Ramesh, N. et al. (1996). "High-Titer Bicistronic Retroviral Vectors Employing Foot-and Mouth Disease Virus Internal Ribosome Entry Site," Nucl. Acid Res. 24(14):2697-2700.
Rees, S. et al. (1996). "Bicistronic Vector for the Creation of Stable Mammalian Cell Lines That Predisposes All Antibiotic-Resistant Cells to Express Recombinant Protein," BioTechniques 20(1): 102-110.
Riechmann, L. et al. (Mar. 24, 1988). "Reshaping Human Antibodies for Therapy," Nature 33(6162):323-327.
Silverman, J. et al. (Dec. 2005, e-pub. Nov. 20, 2005). "Multivalent Avimer Proteins Evolved By Exon Shuffling of a Family of Human Receptor Domains," Nature Biotechnology 23(12):1556-1 561.
Simon, R.J. et al. (Oct. 1992). "Peptoids: A Modular Approach to Drug Discovery," Proc. Nat'l. Acad. Sci. USA 89 (20):9367-9371.
Skerra, A. (2008). "Alternative Binding Proteins: Anticalins—Harnessing the Structural Plasticity of the Lipocaiin Ligand Pocket to Engineer Novel Binding Activities," FEBS J. 275(11):2677-2683.
Smith, G.P. et al. (1985). "Filamentous Fusion Phage: Novel Expression Factors that Display Cloned Antigens on the Virion Surface," Science 228:1315-1317.
Smith, T.F. et al. (1981). "Comparison of Biosequences," Advances in Appl. Math. 2:482-489.
Stein, I. et al. (Jun. 1998). "Translation of Vascular Endothelial Growth Factor mRNA by Internal Ribosome Entry: Implications for Translation Under Hypoxia," Mol. Cell. Biol. 18(6):3112-3119.
Stemmer, W.P.C. et al. (1995). "Single-Step Assembly of a Gene and Entire Plasmid From Large Numbers of Oligodeoxyribonucleotides," Gene 164:49-53.
Trichas, G. et al. (Sep. 15, 2008). "Use of the Viral 2A Peptide for Bicistronic Expression in Transgenic Mice," BMC Biol. 6(40):1-15.
Verhoeyan, M. et al. (Mar. 25, 1988). "Reshaping Human Antibodies: Grafting an Antilysozyme Activity," Science 239:1534-1536.
Vinckc, C. et al. (2012). "Introduction to Heavy Chain Antibodies and Derived Nanobodies," Methods Mol. Biol. 911:15-26.
Wang, T-T. et al. (2001). "Transformation Systems of Non-*Saccharomyces* Yeasts," Crit. Rev. Biotechnoi. 21 (3):177-218.
Wang, Y. et al. (2016). "Nanobody-Derived Nanobiotechnoiogy Tool Kits for Diverse Biomedical and Biotechnology Applications," Int. J. Nanomedicine 11:3287-3303.
Wilson et al. "The Use of mRNA Display to Select High-Affinity Protein-Binding Peptides," Proc Natl Acad Sci USA (2001) 98(7): 3750-3755.
Winter, G. et al. (Jan. 24, 1991). "Man-Made Antibodies," Nature 349(6307):293-299.
Yang, N-S. et al. (Dec. 1990). "In Vivo and In Vitro Gene Transfer to Mammalian Somatic Cells by Particle Bombardment," Proc. Natl. Acad. Sci. USA 87:9568-9572.
Yonezawa, M. et al., (2003). "DNA Display for in Vitro Selection of Diverse Peptide Libraries," Nucleic Acids Res. 31 (19):e118:1-5.

(56) References Cited

OTHER PUBLICATIONS

Argos, P. (1990). "An Investigation of Oligopeptides Linking Domains in Protein Tertiary Structures and Possible Candidates for General Gene Fusion," J. Mol. Biol. 211 (4):943-958.

Buerth, C. et al. (Jun. 29, 2016). "Candida utilis and Cyberlindnera (Pichia) jadinii: Yeast Relatives With Expanding Applications," Appl. Microbiol. Biotechnol. 100(16):6981-6990.

Chu, G. et al. (Mar. 1981) SV40 DNA Transfection of Cells in Suspension: Analysis of the Efficiency of Transcription and Translation of T-Antigen, Gene 13(2):197-202.

Dayhoff, M.O., ed. (1978). "A Model of Evolutionary Change in Proteins," Chapter 22 in Atlas of Protein Sequence and Structure, National Biomedical Research Foundation, Washington DC, 5(Supp. 3):345-358.

Dohmen, R.J. et al. (1991) "An Efficient Transformation Procedure Enabling Long-Term Storage of Competent Cells of Various Yeast Genera," Yeast 7(7):691-692.

Ebersbach, H. et al. (Sep. 7, 2007). "Affilin—Novel Binding Molecules Based on Human γ-B-Crystallin, an All β-Sheet Protein," J. Mol. Biol. 372 (1):172-185.

Edge, M.D. et al. (Aug. 20, 1981). "Total Synthesis of a Human Leukocyte Interferon Gene," Nature 292:756-762.

Extended European Search Report dated Nov. 8, 2021, for European Patent Application No. 18889782.1, filed on Jun. 3, 2020, 9 pages.

Ford, C.F. et al. (1991). "Fusion Tails for the Recovery and Purification of Recombinant Proteins," Protein Expression and Purification 2:95-107.

Fujii, R. et al. (Jun. 27, 2014). "Error-Prone Rolling Circle Amplification Greatly Simplifies Random Mutagenesis," Chapter 2 in Methods Mol. Biol. 1179:23-29.

Gietz, R.D. et al. (Apr. 15, 1995). "Studies on the Transformation of Intact Yeast Cells by the LIAc/SS-DNA/PEG procedure," Yeast 11(4):355-360.

Gollihar, Jr., J.D. (Aug. 2017). "Methods in Protein Engineering and Screening: From Rational Design to Directed Evolution and Beyond," Dissertation the University of Texas at Austin, Doctor of Philosophy, 376 pages.

Gray S.A. et al. (Apr. 1, 2010). "Flow Cytometry-Based Methods for Assessing Soluble scFv Activities and Detecting Antigens in Solution," Biotechnol Bioeng. 105(5):973-981, 16 pages.

Gurtu, V. et al. (Dec. 4, 1996). "IRES Bicistronic Expression Vectors for Efficient Creation of Stable Mammalian Cell Lines," Biochem. Biophys. Res. Comm. 229(1):295-298.

Harvey, B.R. et al. (Jun. 22, 2004). "Anchored Periplasmic Expression, A Versatile Technology for the Isolation of High-Affinity Antibodies From Escherichia coli-Express Libraries," Proceedings of the National Academy of Sciences 101(25):9193-9198.

Hayama, Y. et al. (2002). "Extremely Simple, Rapid and Highly Efficient Transformation Method for the Yeast Saccharomyces cerevisiae Using Glutathione and Early Log Phase Cells," J. Biosci. Bioeng. 94(2):166-171.

IGEM Registry of Standard Biological Parts. (2021). "International Genetically Engineered Machine," iGEM Foundation, 4 pages.

Ishii, J. et al. (May 18, 2012). "Cell Wall Trapping of Autocrine Peptides for Human G-protein-Coupled Receptors on the Yeast Cell Surface," PLoS ONE 7(5)e37136, 1-10.

Johnson, A. et al. (Aug. 2012, e-pub. Jul. 10, 2012). "Sensitive Affimer and Antibody Based Impedimetric Label-Free Assays for C-Reactive Protein," Anal. Chem. 84 (15):6553-6560.

Johnston, S.A. et al. (Jun. 10, 1988). "Mitochondrial Transformation in Yeast by Bombardment With Microprojectiles," Science 240:1538-1541.

Kenan, D.J. et al. (1999). "In Vitro Selection of Aptamers From RNA Libraries," Methods Mol. Biol. 118:217-231.

Labrou, N.E. (Feb. 2010). "Random Mutagenesis Methods for in Vitro Directed Enzyme Evolution," Curr Protein Pept Sci. 11(1):91-100.

Müller, O.J. et al. (Sep. 2003, e-pub. Aug. 3, 2003). "Random Peptide Libraries Displayed on Adeno-Associated Virus to Select for Targeted Gene Therapy Vectors," Nat. Biotechnol. 21:1040-1046.

Nilsson, B. et al. (1991). "Expression and Purification of Recombinant Insulin-Like Growth Factors From Escherichia coli," Methods Enzymol. 198:3-16.

Platella, C. et al. (2017, e-pub. Nov. 16, 2016). "G-Quadruplex-Based Aptamers Against Proteins Targets in Therapy and Diagnostics," Biochim. Biophys. 1861:1429-1447.

Smith, D.B. et al. (Jul. 1988). "Single-Step Purification of Polypeptides Expressed in Escherichia coli as Fusions With Glutathione S-Transferase," Gene 67(1):31-40.

Stumpp, M.T. et al. (Aug. 2008). "DARPins: A New Generation of Protein Therapeutics," Drug Discov. Today 13 (15-16):695-701.

Tanaka, T. et al. (Aug. 2012, e-pub. Jun. 1, 2012). "Recent Developments in Yeast Cell Surface Display Toward Extended Applications in Biotechnology," Appl. Microbiol. Biotechnol. 95(3):577-591.

Wilson, A.C. et al. (2011). "Transposon-Mediated Random Mutagenesis of Bacillus subtilis," Chapter 21 in Methods Mol. Biol. 765:359-371.

Worrall, A.F. (1994). "Site-Directed Mutagenesis by the Cassette Method," Chapter 16 in Methods Mol. Biol. 30:199-210.

Zoller, M.J. et al. (1983). "Oligonucleotide-Directed Mutagenesis of DNA Fragments Cloned Into M13 Vectors," Methods Enzymol. 100:468-500.

Petrovskaya, L.E. et al. (2011). "Alternative Scaffold Proteins," institution of the Russian Academy of Sciences Institute of Bioorganic Chemistry Acad., 22 pages. (Translation of the English Abstract).

* cited by examiner

YEAST DISPLAY OF PROTEINS IN THE PERIPLASMIC SPACE

CROSS-REFERENCE TO RELATED APPLICATION

This application is a national stage application under 35 U.S.C. § 371 of International Application No. PCT/US2018/064775, filed internationally on Dec. 10, 2018, which claims priority to U.S. Provisional Application No. 62/597,388 filed on Dec. 11, 2017, the contents of which are incorporated herein by reference in their entirety.

STATEMENT REGARDING FEDERALLY SPONSORED RESEARCH

This invention was made with government support under Grant No. 1747391 awarded by the National Science Foundation. The government has certain rights in the invention.

TECHNICAL FIELD

The disclosure relates to cell display and methods of high-throughput screening of protein libraries. In particular, the disclosure relates to methods for displaying proteins in the periplasmic space of yeast and the use of such methods for screening protein libraries for specific binding or functional characteristics.

BACKGROUND

Molecular display technology has proven invaluable for the discovery, production, and optimization of proteins and peptides for a variety of biotechnological and biomedical applications. Various approaches including phage display (Smith (1985) Science 228:1315-1317), mRNA (Wilson et al. (2001) Proc. Natl. Acad. Sci. USA 98:3750-3755) and DNA display (Yonezawa et al. (2003) Nucleic Acids Res. 31:e118), ribosome display (Hanes & Pluckthun (1997) Proc. Natl. Acad. Sci. USA 94:4937-4942), eukaryotic virus display (Bupp & Roth (2002) Mol. Ther. 5:329-335; Muller et al. (2003) Nat. Biotechnol. 21:1040-1046), bacterial display (Lu et al. (1995) Biotechnology 13:366-372), and yeast display (Boder & Wittrup (1997) Nat. Biotechnol. 15:553-557) have been developed to screen combinatorial libraries of recombinant proteins for desired characteristics. Such display technologies have been widely used in protein engineering to identify proteins having improved stability and desired binding affinities and enzymatic activities, and have found use in various applications, including directed evolution, affinity maturation, therapeutic protein and antibody engineering, biofuel production, adsorption of environmental pollutants, epitope mapping, and study of protein-protein interactions.

In particular, yeast display has been used to display a wide variety of prokaryotic and eukaryotic proteins (Cherf et al. (2015) Methods Mol. Biol. 1319:155-175). Expression in yeast cells provides the advantage of allowing proper folding and glycosylation of eukaryotic proteins. In conventional yeast display, recombinant proteins are displayed on the surface of yeast cells by fusion to a cell wall protein. Although *Saccharomyces cerevisiae* has been the most commonly used species for cell surface display, other yeast species, including *Pichia, Candida,* and *Yarrowia* strains have found use for some applications (Tanaka et al. (2012) Appl. Microbiol. Biotechnol. 95(3):577-591, Buerth et al. (2016) Appl. Microbiol. Biotechnol. 100(16):6981-6990, Madzak (2015) Appl. Microbiol. Biotechnol. 99(11):4559-4577).

There remains a need for improved methods that more effectively display proteins, particularly for high-throughput screening of protein-protein interactions with membrane proteins.

SUMMARY

The present disclosure relates to high-throughput screening of protein libraries for specific binding or functional characteristics by displaying proteins in the periplasmic space of yeast cells.

In one aspect, the invention includes a yeast periplasmic display library comprising a plurality of yeast host cells, wherein each yeast host cell comprises: a) a protein variant for display in the yeast host cell periplasmic space, wherein the displayed protein variant is different in each yeast host cell such that the plurality of yeast host cells displays a plurality of protein variants; b) a periplasm anchor protein, wherein the periplasm anchor protein is linked to the protein variant such that the protein variant is displayed in the periplasmic space; and c) a target membrane protein of interest, wherein the membrane protein of interest is located in the yeast host cell plasma membrane and accessible to the protein variant displayed in the yeast host cell periplasmic space. The yeast host cells may be haploid or diploid.

In certain embodiments, the protein variant and the periplasm anchor protein are covalently linked together in a fusion protein. In other embodiments, the protein variant and the periplasm anchor protein are noncovalently linked together by molecular binding interactions in a complex. In other embodiments, the protein variant and the periplasm anchor protein are linced by a linked by a non-peptidic bond in a complex. In some embodiments, the non-peptidic bond is a disulfide bond.

In certain embodiments, the periplasm anchor protein comprises a signal sequence that directs transport of the fusion protein to the yeast host cell periplasm, plasma membrane, or cell wall such that the fused protein variant is displayed in the periplasm. An exemplary signal sequence that can be used is the prepro-alpha-factor signal sequence.

In certain embodiments, the periplasm anchor protein comprises a membrane-spanning transmembrane domain that projects the fused protein variant into the periplasm.

In certain embodiments, the periplasm anchor protein comprises a cell-membrane associated protein domain that localizes to an external face of the cell membrane such that the displayed protein variant is projected into the periplasm. In certain embodiments, the cell-membrane associated protein domain is a glycosylphosphatidylinositol (GPI)-plasma membrane anchoring domain. For example, the GPI-plasma membrane anchoring domain may be a yapsin GPI plasma membrane anchoring domain such as, but not limited to, a YPS1, YPS2, YPS3, YPS4, YPS5, YPS6, or YPS7 yapsin GPI plasma membrane anchoring domain.

In certain embodiments, the periplasm anchor protein is a protein that binds to an inner face of the cell wall such that the displayed protein variant is projected into the periplasm.

In certain embodiments, the periplasm anchor protein comprises a signal sequence that directs transport of the fusion protein to the yeast host cell periplasm, and the periplasm anchor protein is sufficiently large that the fusion protein is retained in the periplasm.

In certain embodiments, the anchor protein is a component of a periplasmic protein complex that is sufficiently large that formation of the complex in the periplasm results in retention of the fusion protein in the periplasm.

In another embodiment, the fusion protein further comprises a tag.

In certain embodiments, the protein variants are antibodies, antibody mimetics, aptamers, antigens, enzymes, receptors, hormones, substrates, agonists, antagonists, or ligands.

In certain embodiments, the protein variants are antibodies selected from the group consisting of monoclonal antibodies, chimeric antibodies, nanobodies, recombinant fragments of antibodies, Fab fragments, Fab' fragments, F(ab')$_2$ fragments, F$_v$ fragments, and scFv fragments.

In certain embodiments, each yeast host cell in the yeast periplasmic display library further comprises a target protein of interest that is expressed in a location accessible to the displayed protein variant (e.g., in close enough proximity for the displayed protein variant to bind to the target protein of interest). For example, the target protein of interest may be located in the yeast host cell plasma membrane or periplasm. The target protein of interest can be, for example, a membrane protein, a receptor, an ion channel, or a transporter. In one embodiment, the target protein of interest is a G-protein coupled receptor (GPCR).

In certain embodiments, each yeast host cell further comprises a reporter system for detecting a response of the target protein of interest to a protein-protein interaction with the displayed protein variant. In certain embodiments, the displayed protein variant is an antagonist of the target protein of interest, and the response is a decrease in activity of the target protein of interest upon binding of the antagonist to the target protein of interest, wherein the reporter system detects the decrease in activity of the target protein of interest upon binding of the antagonist to the target protein of interest. In other embodiments, the displayed protein variant is an agonist of the target protein of interest, and the response is an increase in activity of the target protein of interest upon binding of the agonist to the target protein of interest, wherein the reporter system detects the increase in activity of the target protein of interest upon binding of the agonist to the target protein of interest.

In certain embodiments, activation of the target protein of interest increases growth of the yeast host cells. In this case, the yeast periplasmic display library may be screened for an agonist of the target protein of interest by culturing at least a subset of the yeast host cells of the yeast periplasmic display library in a media, wherein growth of a yeast host cell in the media indicates that the protein variant displayed in the yeast host cell is an agonist of the target protein of interest.

In other embodiments, activation of the target protein of interest decreases growth of the yeast host cells. In this case, the yeast periplasmic display library may be screened for an antagonist of the target protein of interest by culturing at least a subset of the yeast host cells of the yeast periplasmic display library in a media, wherein growth of a yeast host cell in the media indicates that the protein variant displayed in the yeast host cell is an antagonist of the target protein of interest.

In another embodiment, the invention includes a yeast periplasmic display library comprising a plurality of yeast host cells, wherein each yeast host cell comprises: a) a fusion protein comprising a periplasm anchor protein fused to an antibody for display in the yeast host cell periplasmic space, wherein the displayed antibody is different in each yeast host cell such that the plurality of yeast host cells displays a plurality of antibodies; and b) a target membrane protein of interest, wherein the membrane protein of interest is located in the yeast host cell plasma membrane and accessible to the antibody displayed in the yeast host cell periplasmic space.

The target membrane protein of interest may be, for example, a receptor, an ion channel, and a transporter. In some embodiments, the target membrane protein of interest comprises a mutation that increases or decreases its activity.

Antibodies that may be displayed with the target membrane protein of interest may include, but are not limited to, monoclonal antibodies, chimeric antibodies, humanized antibodies, nanobodies, recombinant fragments of antibodies, Fab fragments, Fab' fragments, F(ab')$_2$ fragments, F$_v$ fragments, and scFv fragments.

In certain embodiments, the yeast periplasmic display library further comprises a reporter system comprising a reporter gene operably linked to an inducible promoter that is activated when the target membrane protein of interest is activated to allow detection of increases or decreases in activity of the target membrane protein of interest upon binding of the antibody to the target membrane protein of interest. For example, the reporter gene may be a nutritional marker (e.g., HIS3, HIS7, ARG6, LEU2, URA3, and TRP1), antibiotic resistance marker (e.g., confers resistance to an antibiotic such as geneticin (e.g., aphA1), zeocin (e.g., ble), hygromycin B, nourseothricin, or bialaphos), fluorescent marker (e.g., of a green fluorescent protein, a red fluorescent protein, a blue fluorescent protein, a cyan fluorescent protein, a yellow fluorescent protein, and an orange fluorescent protein), bioluminescent marker (e.g., luciferase or aequorin), or counter-selectable marker (e.g., CAN1, URA3, MET15, TRP1, and TK). In certain embodiments, the reporter gene is a selectable marker such that increases in activity of the target membrane protein of interest upon binding of the antibody to the target membrane protein of interest are detectable by growth of the yeast host cells on a positive selection media. In other embodiments, the reporter gene is a counter-selectable marker such that decreases in activity of the target membrane protein of interest upon binding of the antibody to the target membrane protein of interest are detectable by growth of the yeast host cells on media comprising a counterselection agent.

In certain embodiments, the target membrane protein of interest is a G-protein coupled receptor (GPCR), for example, an exogenous GPCR such as a mammalian GPCR (e.g., from human or nonhuman primate, rodent, laboratory animal, livestock). In certain embodiments, the mammalian GPCR is a human GPCR selected from the group consisting of CXCR4, CXCR5, SSTR2, MOR, AVPR2, FPR2/ALX, ADORA2A, CHRM3, CGRP2, CCR2, CCR4, CCR5, CHRM4, PAC1, b2AR, CXCR2, CYSLTR2, KSHV vGPCR, PKR1, PKR2, CB1, CB2, A3AR, and AT1R.

In certain embodiments, the yeast periplasmic display library further comprises an engineered Gα subunit capable of being activated by the GPCR, wherein the activated engineered Gα subunit is capable of activating a detectable pheromone response in the yeast host cell.

In certain embodiments, the engineered Gα subunit is a chimeric G protein alpha (Gα) subunit comprising an N-terminal domain of a yeast Gα subunit and a C-terminal domain of an exogenous Gα subunit. For example, the yeast Gα subunit may belong to a Gαi, Gαq, Gαs, or Gαo family G protein. In the chimeric Gα subunit, at least five C-terminal residues of a yeast Gα subunit may be replaced with corresponding C-terminal residues of a mammalian Gα subunit such that the chimeric Gα subunit is capable of being activated by a mammalian GPCR. In some embodiments, at least 20 C-terminal residues of the yeast Gα subunit are replaced with corresponding C-terminal residues of the mammalian Gα subunit such that the chimeric Gα subunit is capable of being activated by the mammalian GPCR. In another embodiment, the chimeric Gα subunit comprises at least 41 N-terminal residues of the yeast Gα subunit.

Exemplary mammalian Gα subunits include G alpha-S, G alpha-I, G alpha-O, G alpha-T, G alpha-Z, G alpha-Q, G alpha-11, G alpha-12, G alpha-13, and transducin.

In some embodiments, the target GPCR of interest has constitutive ligand-independent activity. In other embodiments, a ligand is added to activate the target GPCR of interest.

In certain embodiments, the yeast host cell is a haploid or diploid yeast host cell. In certain embodiments, the yeast host cell is a Δfar1, Δsst2, Δste14, Δste3 or Δmat strain. A Δmat strain may comprise, for example, a deleted or inactivated MATα locus or a deleted or inactivated MATα locus.

In another embodiment, the yeast host cell further comprises a modified CLN3 protein comprising a C-terminal truncation that increases abundance of CLN3 in the yeast host cell compared to a wild-type CLN3 protein. For example, the modified CLN3 protein may retain at least N-terminal amino acids 1-387 or 1-408 of the wild-type CLN3 protein, or any number of N-terminal amino acids within these ranges, such as 1-388, 1-389, 1-390, 1-391, 1-392, 1-393, 1-394, 1-395, 1-396, 1-397, 1-398, 1-399, 1-400, 1-401, 1-402, 1-403, 1-404, 1-405, 1-406, 1-407, or 1-408, wherein the C-terminal truncation comprises a deletion of all or some of the remaining residues of the wild-type CLN3 protein.

In another embodiment, the yeast host cell is a FAR1 strain for selection of antibody antagonists of a GPCR.

In another embodiment, the yeast host cell is a Marl strain comprising a pheromone-inducible PRM1 promoter operably linked to a reporter gene for selection of antibody agonists of a GPCR.

In another aspect, the invention provides a yeast periplasmic display library comprising a plurality of yeast host cells, wherein each yeast host cell comprises: a) an antibody for display in the yeast host cell periplasmic space, wherein the displayed antibody is different in each yeast host cell such that the plurality of yeast host cells displays a plurality of antibodies, wherein the antibody is linked to a signal sequence that directs transport of the antibody to the yeast host cell periplasm, plasma membrane or cell wall, such that the antibody is displayed in the yeast host cell periplasmic space; and b) a target membrane protein of interest, wherein the membrane protein of interest is located in the yeast host cell plasma membrane and accessible to the antibody displayed in the yeast host cell periplasmic space.

In another aspect, the invention includes a method of making a yeast periplasmic display library described herein, the method comprising: a) providing a plurality of recombinant polynucleotides encoding fusion proteins, wherein each recombinant polynucleotide encodes a different fusion protein comprising the periplasm anchor protein fused to a different antibody for display; b) transfecting the plurality of yeast host cells with the plurality of recombinant polynucleotides encoding the fusion proteins; c) transfecting the plurality of yeast host cells with a recombinant polynucleotide encoding the target membrane protein of interest; and d) culturing the plurality of yeast host cells under conditions that permit expression of the fusion proteins and the target membrane protein of interest, wherein each yeast host cell displays a different antibody in the periplasmic space and the target membrane protein of interest localizes to the plasma membrane (i.e., where it is accessible to binding by the displayed antibody). In certain embodiments, the recombinant polynucleotides encoding the fusion proteins or the recombinant polynucleotide encoding the target membrane protein of interest are provided by expression vectors. In other embodiments, the recombinant polynucleotides encoding the fusion proteins or the target membrane protein of interest are integrated into the yeast host cell genome at a target locus.

In another aspect, the invention provides a method of making the yeast periplasmic display library, the method comprising: a) providing a first plurality of recombinant polynucleotides encoding the antibodies for display in the yeast host cell periplasmic space, wherein the displayed antibody is different in each yeast host cell such that the plurality of yeast host cells displays a plurality of antibodies; b) providing a second recombinant polynucleotide encoding the periplasm anchor protein, wherein the periplasm anchor protein is linked to the antibody such that the antibody is displayed in the periplasmic space; c) transfecting the plurality of yeast host cells with the first plurality of recombinant polynucleotides and the second recombinant polynucleotide; d) transfecting the plurality of yeast host cells with a recombinant polynucleotide encoding the target membrane protein of interest; and e) culturing the plurality of yeast host cells under conditions that permit expression of the antibodies, the periplasm anchor protein and the target membrane protein of interest, wherein each yeast host cell displays a different antibody in the periplasmic space and the target membrane protein of interest localizes to the plasma membrane, such that the yeast periplasmic display library is produced.

Expression of the fusion proteins and the target membrane protein of interest will generally depend on the presence of a promoter, which may be included in a vector or at a chromosomal locus in which the recombinant polynucleotides are integrated. The promoter may be a constitutive or an inducible promoter. In certain embodiments, each recombinant polynucleotide comprises a promoter operably linked to a polynucleotide encoding a fusion protein or a target membrane protein of interest. The recombinant polynucleotide may be provided by a vector comprising the promoter. In other embodiments, a chromosomal target locus comprises a promoter that becomes operably linked to a polynucleotide encoding a fusion protein or a target membrane protein of interest that integrates at a chromosomal target locus.

In another embodiment, the method further comprises introducing into the plurality of yeast host cells a recombinant polynucleotide encoding an engineered Gα subunit capable of being activated by the GPCR, wherein the activated engineered Gα subunit is capable of activating a detectable pheromone response in the yeast host cell.

In another embodiment, the invention includes a periplasm-targeting expression vector comprising: a) a polynucleotide encoding a signal peptide; b) a cloning site suitable for in-frame insertion of a polynucleotide encoding a protein variant after the polynucleotide encoding the signal peptide; c) a polynucleotide encoding a glycophosphatidylinositol (GPI) plasma membrane anchoring domain, positioned such that the vector is capable of producing a fusion protein comprising the signal peptide and the protein variant fused to the GPI plasma membrane anchoring domain; and d) a promoter operably linked to sequences encoding the fusion protein. In one embodiment, the signal peptide comprises a prepro-alpha-factor signal sequence. In another embodiment, the cloning site comprises one or more restriction sites. In certain embodiments, the GPI plasma membrane anchoring domain is a yapsin GPI plasma membrane anchoring domain such as, but not limited to, a YPS1, YPS2, YPS3, YPS4, YPS5, YPS6, or YPS7 yapsin GPI plasma membrane anchoring domain. In another embodiment, the periplasm-targeting expression vector further comprises a polynucleotide encoding a linker, wherein said polynucleotide encoding the linker is positioned in between the cloning site and the polynucleotide encoding the GPI plasma membrane anchoring domain. The linker may further comprise a tag. In another embodiment, the periplasm-targeting expression vector further comprises a selectable marker.

In another aspect, the invention includes a method of making a yeast periplasmic display library described herein, the method comprising: a) providing a plurality of recombinant polynucleotides encoding antibody variants, wherein each recombinant polynucleotide encodes a different antibody variant; b) transfecting the plurality of yeast host cells with a periplasm-targeting expression vector described herein c) transfecting the plurality of yeast host cells with the plurality of recombinant polynucleotides encoding the antibody variants, wherein in each yeast host cell, a recombinant polynucleotide encoding an antibody variant is integrated into the cloning site of the periplasm-targeting expression vector by homologous recombination to allow expression of a fusion protein comprising a periplasm anchor protein fused to an antibody variant for display; c) transfecting the plurality of yeast host cells with a recombinant polynucleotide encoding the target membrane protein of interest; and d) culturing the plurality of yeast host cells under conditions that permit expression of the fusion proteins and the target membrane protein of interest, wherein each yeast host cell displays a different antibody in the periplasmic space and the target membrane protein of interest localizes to the plasma membrane (i.e., where it is accessible to binding by the displayed antibody). In another embodiment, the method further comprises introducing into the plurality of yeast host cells a recombinant polynucleotide encoding an engineered Gα subunit capable of being activated by the GPCR, wherein the activated engineered Gα subunit is capable of activating a detectable pheromone response in the yeast host cell.

In another aspect, the invention includes a method of screening a yeast periplasmic display library comprising a reporter system, as described herein, for an antibody that modulates activity of the target membrane protein of interest, the method comprising culturing at least a subset of the yeast host cells of a yeast periplasmic display library described herein in a selection media; and detecting expression of the reporter gene, wherein increased expression of a reporter gene indicates that the antibody increases activity of target membrane protein of interest and decreased expression of the reporter gene indicates that the antibody decreases activity of the target membrane protein of interest.

Exemplary reporter genes include a nutritional marker (e.g., HIS3, HIS7, ARG6, LEU2, URA3, and TRP1), an antibiotic resistance marker (e.g., confers resistance to an antibiotic such as geneticin (aphA1), zeocin (ble), hygromycin B, nourseothricin, and bialaphos), a fluorescent marker (e.g., of a green fluorescent protein, a red fluorescent protein, a blue fluorescent protein, a cyan fluorescent protein, a yellow fluorescent protein, and an orange fluorescent protein), bioluminescent marker (e.g., luciferase or aequorin), and a counter-selectable marker (e.g., CAN1, URA3, MET15, TRP1, and TK).

In another embodiment, the method further comprises positive selection for expression of a nutritional marker, wherein growth of the yeast host cells in a nutrient-deficient selection media indicates the target membrane protein of interest is activated.

In another embodiment, the method further comprises positive selection for expression of an antibiotic resistance marker, wherein growth of the yeast host cells in a selection media comprising an antibiotic indicates the target membrane protein of interest is activated.

In another embodiment, the method further comprises positive selection for expression of a fluorescent marker, wherein detection of fluorescence emitted by the yeast host cells indicates the target membrane protein of interest is activated.

In another embodiment, the method further comprises positive selection for expression of a bioluminescent marker, wherein detection of bioluminescence emitted by the yeast host cells indicates the target membrane protein of interest is activated.

In another embodiment, the method further comprises negative selection for expression of the counter-selectable marker, wherein decreases in activity of the target membrane protein of interest upon binding of the displayed antibody to the target membrane protein of interest are detectable by growth of the yeast host cells in a media comprising an agent that selects against cells expressing the counter-selectable marker.

In another embodiment, the invention includes a method of screening a yeast periplasmic display library for an antibody that modulates the activity of a target GPCR of interest, the method comprising culturing at least a subset of the yeast host cells of the yeast periplasmic display library in a media, wherein detection of activation or inhibition of the pheromone response in at least one yeast host cell compared to a control yeast host cell not having an antibody displayed in the periplasmic space indicates that the displayed antibody in said at least one yeast host cell binds to and modulates the activity of the GPCR. In some embodiments, the method further comprises contacting the human GPCR with a ligand. In other embodiments, the GPCR has constitutive ligand-independent activity.

In certain embodiments, the yeast host cell comprises an engineered Gα subunit capable of being activated by the GPCR, wherein the activated engineered Gα subunit is capable of activating a detectable pheromone response in the yeast host cell. In certain embodiments, the engineered Gα subunit is a chimeric G protein alpha (Gα) subunit comprising an N-terminal domain of a yeast Gα subunit and a C-terminal domain of an exogenous Gα subunit. For example, the yeast Gα subunit may belong to a Gαi, Gαq, Gαs, or Gαo family G protein. In the chimeric Gα subunit, at least five C-terminal residues of a yeast Gα subunit may be replaced with corresponding C-terminal residues of a mammalian Gα subunit such that the chimeric Gα subunit is capable of being activated by a mammalian GPCR. In some embodiments, at least 20 C-terminal residues of the yeast Gα subunit are replaced with corresponding C-terminal residues of the mammalian Gα subunit such that the chimeric Gα subunit is capable of being activated by the mammalian GPCR. In another embodiment, the chimeric Gα subunit comprises at least 41 N-terminal residues of the yeast Gα subunit. Exemplary mammalian Gα subunits include G alpha-S, G alpha-I, G alpha-O, G alpha-T, G alpha-Z, G alpha-Q, G alpha-11, G alpha-12, G alpha-13, and transducin.

In certain embodiments, the yeast host cell is a FAR1 strain, wherein inhibition of the pheromone response by an antibody acting as an antagonist that binds to an inhibits the GPCR in the yeast host cell results in cessation of cell cycle arrest and growth of the yeast host cell. In other embodiments, the yeast host cell is a Δfar1 strain comprising a pheromone-inducible PRM1 promoter operably linked to a reporter gene, wherein activation of the pheromone response by an antibody acting as an agonist that binds to and activates the GPCR in the yeast host cell results in increased expression of the reporter gene.

In another aspect, the invention provides a yeast host cell comprising: a) an antibody for display in the yeast host cell periplasmic space, b) a periplasm anchor protein, wherein the periplasm anchor protein is linked to the antibody such that the antibody is displayed in the periplasmic space; and c) a target membrane protein of interest, wherein the membrane protein of interest is located in the yeast host cell plasma membrane and accessible to the antibody displayed in the yeast host cell periplasmic space.

In another aspect, the invention provides an antibody linked to a periplasm anchor protein. In some embodiments, the antibody is produced in a yeast host cell, the antibody is localized to the yeast host cell periplasmic space. In some embodiments, the antibody and the periplasm anchor protein are noncovalently linked together by molecular binding interactions in a complex or are linked by a covalent non-peptidic bond in a complex. In some embodiments, the non-peptidic bond is a disulfide bond. In some embodiments, the antibody and the periplasm anchor protein are covalently linked together in a fusion protein.

In another aspect, the invention provides a method of localizing an antibody to a yeast host cell periplasmic space comprising linking the antibody to a periplasm anchor protein such that the antibody is localized to the periplasmic space. In some embodiments, the antibody and the periplasm anchor protein are noncovalently linked together by molecular binding interactions in a complex or are linked by a covalent non-peptidic bond in a complex. In some embodiments, the non-peptidic bond is a disulfide bond. In some embodiments, the antibody and the periplasm anchor protein are covalently linked together in a fusion protein.

In another aspect, the invention includes a kit comprising a yeast periplasmic display library described herein and instructions for screening a plurality of protein variants for their ability to bind and/or modulate activity of a target protein of interest.

These and other embodiments of the subject invention will readily occur to those of skill in the art in view of the disclosure herein.

BRIEF DESCRIPTION OF THE DRAWINGS

FIG. 1A shows the unique combination of 1) functional human GPCR-yeast coupling to 2) affinity molecule secretion and 3) affinity molecule localization, together in a high-throughput, highly engineerable yeast cellular platform. Functional, properly folded GPCR yields ScFvs (which can easily be converted to IgG antibodies) or nanobodies that are more likely to function as therapeutics in the human organismal context. FIG. 1B shows use of an "antagonist selection strain" to find antagonists. FIG. 1C shows use of an "agonist selection strain" to find agonists. By altering the logic of reporters and selectable markers coupled to the pheromone response system output, the platform can be used to select for agonists or antagonists. FIG. 1D shows direct functional screening yields therapeutic antibody candidates that would normally be missed in traditional screening, which could yield novel binding modes and functional modulation of GPCR targets. Because of the ease of genetic engineering in yeast, we can both adjust antibody and GPCR expression levels, and tune selectable and screenable reporters to be very sensitive. Both enable us to find low-affinity but functional candidates, which can easily be affinity matured later.

FIG. 4A shows that if an expressed anti-GFP nanobody properly folds and localizes, a GFP applied from the outside of the cell (after cell wall digestion) should label the cell membrane. FIG. 4B shows images of yeast expressing an anti-GFP nanobody using our targeting vector, after cell wall digestion and applying purified GFP protein indicate GFP binding at the membrane. No fluorescence was observed in control cells (data not shown) Left, brightfield; Right, GFP channel.

FIG. 5A shows a schematic of the strategy. FIG. 5B shows an example of a "candidate" clone that exhibited alpha factor-resistant growth as analyzed by a halo assay, and then showed no resistance after forcing the plasmid to drop.

DETAILED DESCRIPTION OF THE INVENTION

Figure 1A:
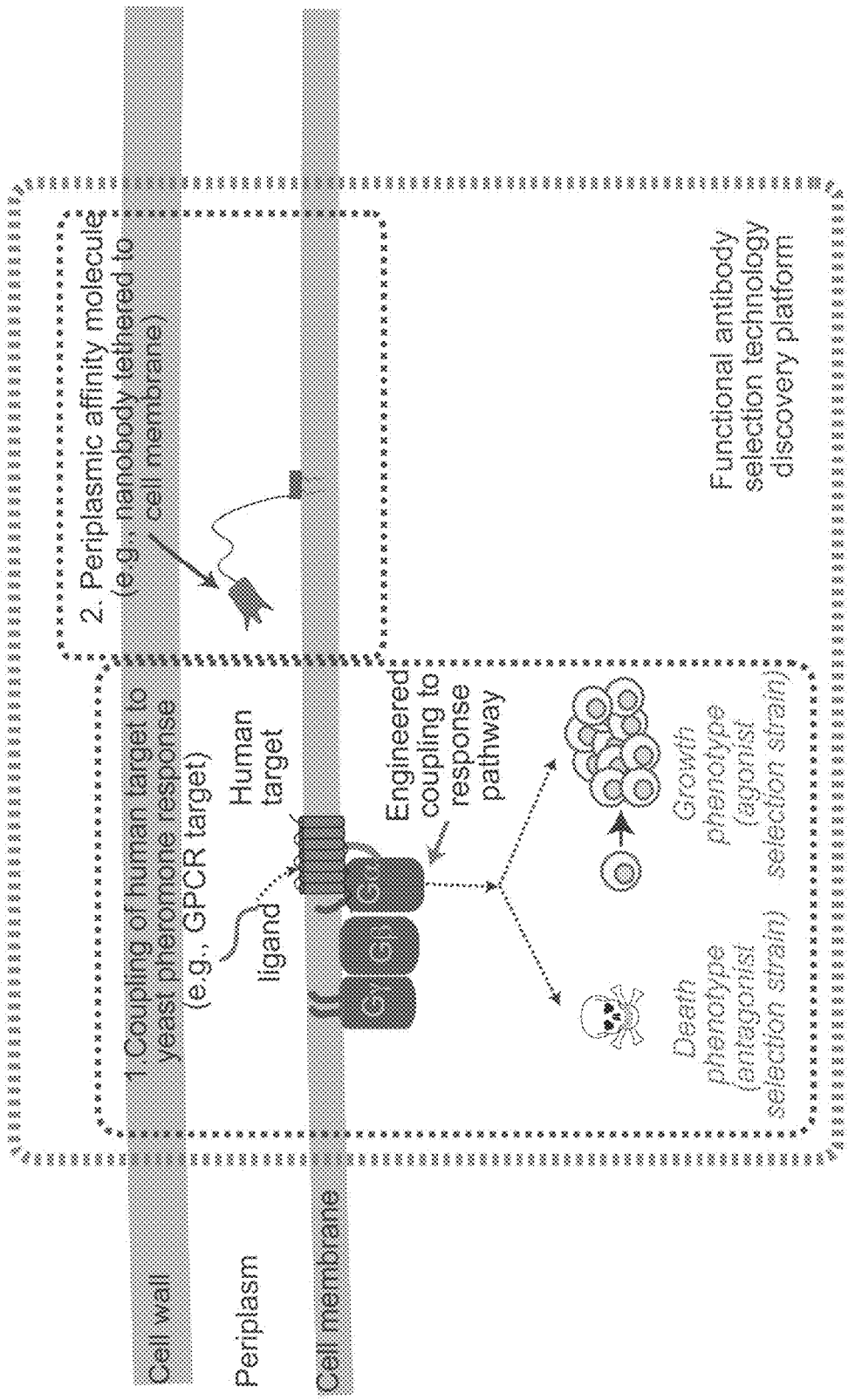
FIGS. 1A-1D show novel yeast cell display method for screening for antibodies that modulate the function of GPCRs.
Figure 1B:
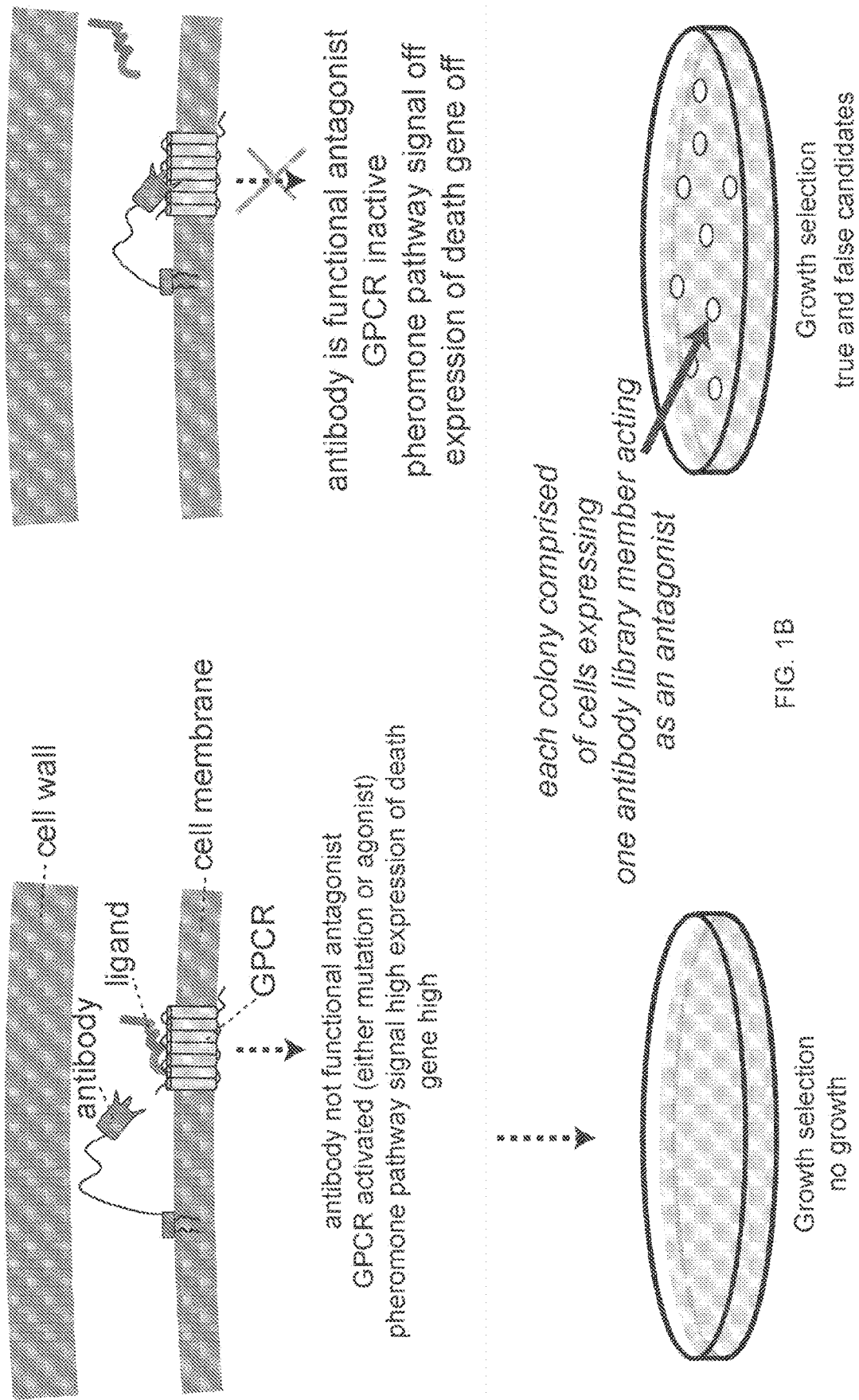
Figure 1C:
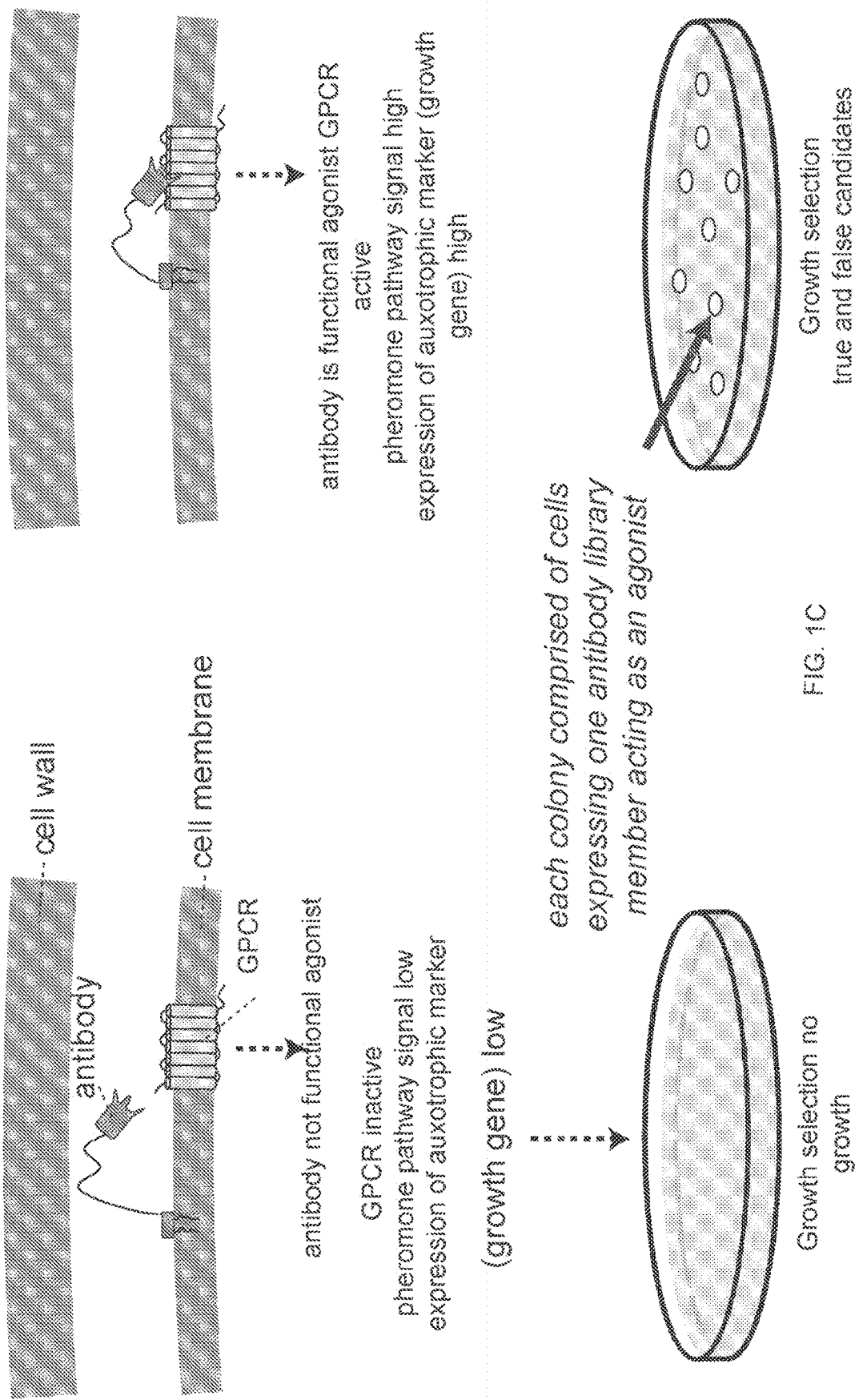
Figure 1D:
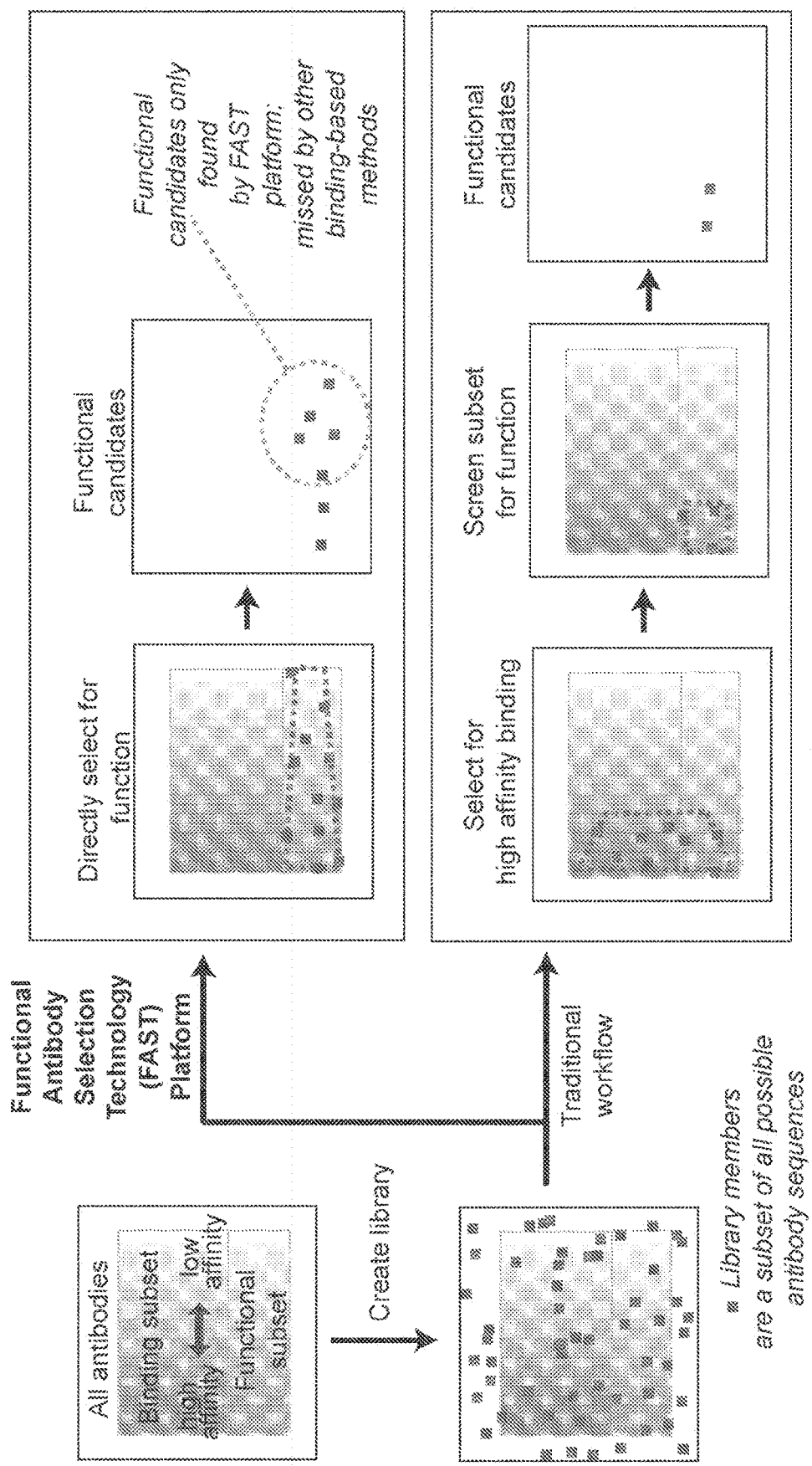
Figure 2:
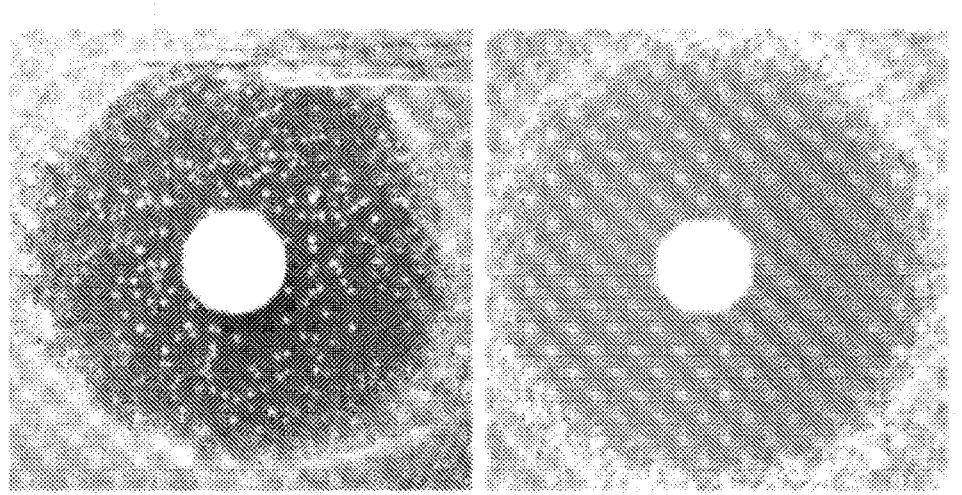
FIG. 2 shows method of reducing background/false positive in "halo assays". $10^7$ cells of the parental strain (left) and the current platform strain (NIY326, right) were plated on agar media. A filter paper disc was placed onto the plate and spotted with 3 μl of 1 mM alpha factor. A zone of no-growth in response to ligand (the desired phenotypic response) was observed in both, but in the parental strain (Left), suppressor mutants arise and grow into colonies in the presence of pheromone (colonies in halo region). In platform strain NI326 (Right), we have reduced the background rate to ~$10^{-7}$, as demonstrated in the clear halo zone and lack of background suppressor mutations that would act as false positives in an antagonist selection.
Figure 3:
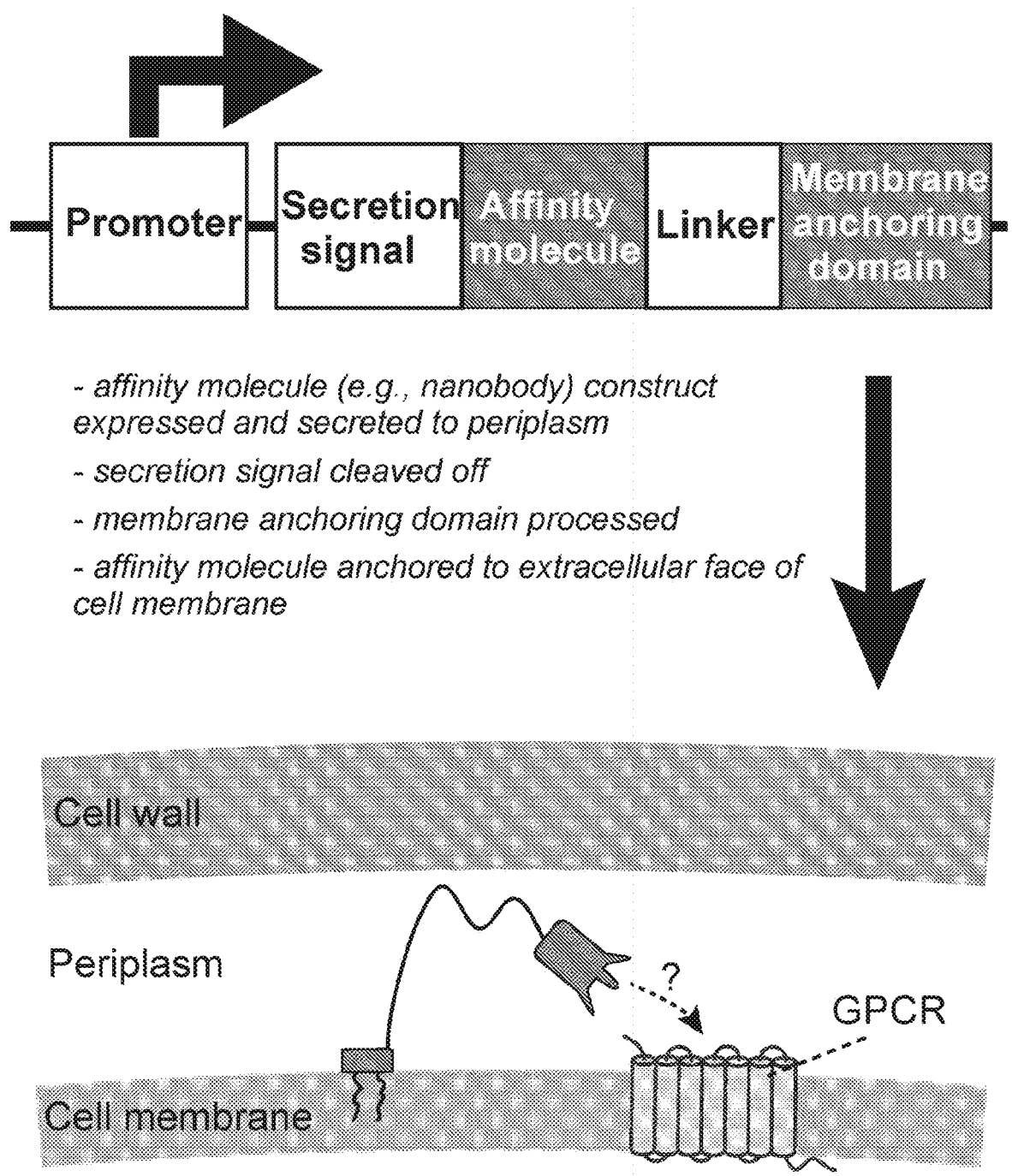
FIG. 3 shows affinity molecule targeting vector structure and concept. We cloned the affinity molecule downstream of a secretion signal and upstream of a linker and extracellular membrane-anchoring domain from GPI. When expressed in cells, the protein is secreted into the extracellular space, and then the GPI domain is processed to leave a domain with a GPI that binds to the membrane, which tethers the affinity molecules to this cell and leaves it free to interact with the target GPCR on its extracellular face.

A plethora of therapeutic targets in such diseases as cancer and inflammation involve cell membrane-associated proteins. However, many cell membrane-associated proteins with the greatest therapeutic potential for high-impact diseases are difficult to drug. Although small molecules affecting the function of these proteins are easily found, they are often non-specific. Unlike small molecules, antibodies and related affinity molecules (e.g., nobodies and ScFvs and Fabs), are an appealing therapeutic class due to their potentially superior specificity, functional diversity, and pharmacological properties. Additionally, antibodies can better interact with extracellular domains and loops, which can modulate the structure (and thus function) of cell membrane-associated proteins, such as GPCRs, in more sophisticated ways than small molecules. However, there is to date not a single approved GPCR antibody therapeutic in the United States, and only one worldwide, in Japan.

Current yeast or phage display workflows identify antibodies that tightly bind but often do not affect the function of cell membrane-associated proteins, such as GPCRs. The antigens used are often fragments that do not represent the functional protein accessible to the antibody in vivo, or are heterogeneously structured full-length protein preparations. The workflow also overlooks a tremendous fraction of total functional diversity, because most antibodies are never functionally assayed. What is needed is a high-throughput platform to directly select for antibodies that modulate the function of cell membrane-associated proteins, such as GPCRs.

It is much less straightforward to develop antibodies that alter the function of cell membrane-associated proteins, such as GPCRs (Jo 2015, Hutchings 2010). This is due primarily to the following issues with many current solutions: 1) The antigens used are lacking. Antigens derived from extracellular peptides or fragments may be good for developing antibodies for Western blots, but do not structurally represent therapeutically relevant targets. Further, homogenously, functionally folded full-length protein in lipids or detergents can be hard to prepare in sufficient amounts for immunization, phage display, or yeast display. 2) Antibodies selected for their high affinity are mostly non-functional; they bind to regions in the protein that do not affect function. 3) Workflows lose significant antibody diversity—and therefore functionality—in selected antibodies. By first selecting for antibodies that bind tightly and discarding the rest, huge amounts of functional diversity are lost. Mammalian cell systems have been created to functionally screen antibody candidate subsets in an autocrine fashion (Zhang 2014), which partially addresses issue 2, but due to transformation efficiencies ($\sim 10^4$) and limited engineerability of selectable/screenable readouts, they are limited to screens of small subsets of candidates.

Our innovation includes combining cell membrane-associated protein-to-yeast pheromone response coupling and expressing affinity molecules that act in cis in the same cell in a high-throughput platform. This enables direct and high-throughput functional selection of affinity molecules in the yeast periplasmic space. Antibodies and related affinity molecules are large molecules with complex folding patterns that must be maintained to retain binding activity. While unstructured, short peptides may be able to be localized to the yeast periplasmic space, it was not previously known that antibodies and related affinity molecules could be displayed in the yeast periplasmic space and retain binding activity.

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., *High Throughput Screening: Methods and Protocols* (Methods in Molecular Biology, W. P. Janzen ed., Humana Press, 3$^{rd}$ edition, 2016); *G Protein-Coupled Receptors: Structure, Signaling, and Physiology* (S. Siehler and G. Milligan eds., Cambridge University Press, 2010); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a cell" includes a mixture of two or more cells, and the like.

The term "about," particularly in reference to a given quantity, is meant to encompass deviations of plus or minus five percent.

The term "about," particularly in reference to a given quantity, encompasses and describes the given quantity itself.

The terms "polypeptide" and "protein" refer to a polymer of amino acid residues and are not limited to a minimum length. Thus, peptides, oligopeptides, dimers, multimers, and the like, are included within the definition. Both full length proteins and fragments thereof are encompassed by the definition. The terms also include post expression modifications of the polypeptide, for example, glycosylation, acetylation, phosphorylation, hydroxylation, and the like. Furthermore, for purposes of the present invention, a "polypeptide" refers to a protein which includes modifications, such as deletions, additions and substitutions to the native sequence. These modifications may be deliberate, as through site directed mutagenesis, or may be accidental, such as through mutations of hosts which produce the proteins or errors due to PCR amplification.

The term "antibody" encompasses monoclonal antibodies as well as hybrid antibodies, altered antibodies, chimeric antibodies, and humanized antibodies. The term antibody includes: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain F$_v$ molecules (scFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) *J Immunology* 149B: 120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule.

The phrase "specifically (or selectively) binds" with reference to binding of an antibody to an antigen (e.g., GPCR) refers to a binding reaction that is determinative of the presence of the antigen in a heterogeneous population of proteins and other biologics. Thus, under designated immunoassay conditions, the specified antibodies bind to a particular antigen at least two times the background and do not substantially bind in a significant amount to other antigens present in the sample. Specific binding to an antigen under such conditions may require an antibody that is selected for its specificity for a particular antigen. For example, antibodies raised to an antigen from specific species such as rat, mouse, or human can be selected to obtain only those antibodies that are specifically immunoreactive with the antigen and not with other proteins, except for polymorphic variants and alleles. This selection may be achieved by subtracting out antibodies that cross-react with molecules from other species. A variety of immunoassay formats may be used to select antibodies specifically immunoreactive with a particular antigen. For example, solid-phase ELISA immunoassays are routinely used to select antibodies specifically immunoreactive with a protein (see, e.g., Harlow & Lane. Antibodies, A Laboratory Manual (1988), for a description of immunoassay formats and conditions that can be used to determine specific immunoreactivity). Typically, a specific or selective reaction will be at least twice background signal or noise and more typically more than 10 to 100 times background.

A protein is said to "interact" with another protein if it binds specifically (e.g., in a lock-and-key type mechanism), non-specifically or in some combination of specific and non-specific binding. A first protein "interacts preferentially" with a second protein if it binds (non-specifically and/or specifically) to the second protein with greater affinity and/or greater specificity than it binds to other proteins. The term "affinity" refers to the strength of binding and can be expressed quantitatively as a dissociation constant ($K_d$). It is to be understood that specific binding does not necessarily require interaction between specific amino acid residues and/or motifs of each protein. For example, in certain embodiments, a first protein may interact preferentially with a second protein but, nonetheless, may be capable of binding other polypeptides at a weak, yet detectable, level (e.g., 10% or less of the binding shown to the polypeptide of interest). Typically, weak binding, or background binding, is readily discernible from the preferential interaction with the compound or polypeptide of interest, e.g., by use of appropriate controls.

As used herein, the term "binding pair" refers to first and second molecules that specifically bind to each other. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. Examples include antigen-antibody, receptor-hormone, receptor-ligand, receptor-agonist, and receptor-antagonist binding pairs.

As used herein, the term "ligand" refers to a molecule that binds to another molecule, e.g., an antigen binding to an antibody, a hormone, agonist, or antagonist binding to a receptor, a neurotransmitter binding to an ion channel, or a substrate, inhibitor, or allosteric effector binding to an enzyme and includes natural and synthetic biomolecules, such as proteins, polypeptides, peptides, nucleic acid molecules, carbohydrates, sugars, lipids, lipoproteins, small molecules, natural and synthetic organic and inorganic materials, synthetic polymers, aptamers, and the like.

The term "polynucleotide," as known in the art, generally refers to a nucleic acid molecule. A "polynucleotide" can include both double- and single-stranded sequences and refers to, but is not limited to, prokaryotic sequences, eukaryotic mRNA, cDNA from viral, prokaryotic or eukaryotic mRNA, genomic RNA and DNA sequences from viral (e.g. RNA and DNA viruses and retroviruses), prokaryotic DNA or eukaryotic (e.g., mammalian) DNA, and especially synthetic DNA sequences. The term also captures sequences that include any of the known base analogs of DNA and RNA, and includes modifications such as deletions, additions and substitutions (generally conservative in nature), to the native sequence. These modifications may be deliberate, as through site-directed mutagenesis, or may be accidental, such as through mutations of hosts including polynucleotides encoding variant polypeptides for display. Modifications of polynucleotides may have any number of effects including, for example, facilitating expression of the polypeptide product in a host cell.

A polynucleotide can encode a biologically active protein or polypeptide. Depending on the nature of the polypeptide encoded by the polynucleotide, a polynucleotide can include as little as 10 nucleotides, e.g., where the polynucleotide encodes an antigen or epitope. Typically, the polynucleotide encodes peptides of at least 10, 11, 12, 13, 14, 15, 16, 17, 18, 19, 20, 21, 22, 23, 24, 25, 30 or even more amino acids.

The terms "variant," "analog" and "mutein" refer to biologically active derivatives of the reference molecule that retain desired activity (e.g., efficient polypeptide display) as described herein. In general, the terms "variant" and "analog" refer to compounds having a native polypeptide sequence and structure with one or more amino acid additions, substitutions and/or deletions relative to the native molecule, as long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem. Biol. (2000) 7:463-473; and Simon et al., Proc. Natl. Acad. Sci. USA (1992) 89:9367-9371 for descriptions of peptoids). Methods for making polypeptide analogs and muteins are known in the art and are described further below.

Analogs generally include substitutions that are conservative in nature, i.e., those substitutions that take place within a family of amino acids that are related in their side chains. Specifically, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein, polypeptide, or peptide means a polypeptide produced by expression of a recombinant polynucleotide. In general, the gene of interest is cloned and then expressed in transformed organisms, as described further below. The host organism expresses the foreign gene to produce the protein under expression conditions.

A "polynucleotide coding sequence" or a sequence that "encodes" a selected polypeptide, is a nucleic acid molecule that is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A transcription termination sequence may be located 3' to the coding sequence. Typical "control elements," include, but are not limited to, transcription regulators, such as promoters, transcription enhancer elements, transcription termination signals, and polyadenylation sequences; and translation regulators, such as sequences for optimization of initiation of translation, e.g., Shine-Dalgarno (ribosome binding site) sequences, Kozak sequences (i.e., sequences for the optimization of translation, located, for example, 5' to the coding sequence), leader sequences (heterologous or native), translation initiation codon (e.g., ATG), and translation termination sequences. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

By "fragment" is intended a molecule consisting of only a part of the intact full-length sequence and structure. The fragment can include a C-terminal deletion an N-terminal deletion, and/or an internal deletion of the peptide. Active fragments of a particular protein or peptide will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the full-length sequence, provided that the fragment in question retains biological activity.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide molecules. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid or viral vector construct. In addition to the components of the expression cassette, the construct may also include, one or more selectable markers, a signal which allows the construct to exist as single stranded DNA (e.g., a M13 origin of replication), at least one multiple cloning site, and an origin of replication (e.g., autonomously replicating sequence in yeast).

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as plasmid and viral vectors.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures," and other such terms denoting microorganisms or eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

The terms "label" and "detectable label" refer to a molecule capable of detection, including, but not limited to, radioactive isotopes, stable (non-radioactive) heavy isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to radiolabels (e.g., $^3$H, $^{125}$I, $^{35}$S, $^{14}$C, or $^{32}$P), stable (non-radioactive) heavy isotopes (e.g., $^{13}$C or $^{15}$N), phycoerythrin, fluorescein, 7-nitrobenzo-2-oxa-1,3-diazole (NBD), YPet, CyPet, Cascade blue, allophycocyanin, Alexa dyes (e.g., Alexa 350, Alexa 430, Alexa 488, Alexa 532, Alexa 546, Alexa 555, Alexa 594, Alexa 647, Alexa 660, Alexa 680, and Alexa 750), Atto dyes (e.g., Atto 488, Atto 532, Atto 550, Atto 565, Atto 590, Atto 610, Atto 620, Atto 635, Atto 647, Atto 655, and Atto 680), cyanine dyes (e.g., Cy3, Cy5, and Cy7), TYE 563, TYE 665, TYE 705, TEX 615, JOE, TET, HEX, TAMRA, ROX, rhodamine, dansyl, umbelliferone, Texas red, luminol, acradimum esters, biotin or other streptavidin-binding proteins, magnetic beads, electron dense reagents, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, rsCherry, rsCherryRev, firefly luciferase, *Renilla* luciferase, NADPH, beta-galactosidase, horseradish peroxidase, glucose oxidase, alkaline phosphatase, chloramphenical acetyl transferase, and urease. Enzyme tags are used with their cognate substrate. As with many of the standard procedures associated with the practice of the invention, skilled artisans will be aware of additional labels that can be used.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the development of methods for displaying recombinant proteins in the periplasmic space of yeast cells. In particular, recombinant proteins are linked to a cell membrane-spanning transmembrane domain, a cell-membrane associated protein domain that is on the external face of the yeast cell membrane, a protein that binds to the inner face of the yeast cell wall, or a periplasmic protein in order to display proteins in the yeast periplasmic space. Recombinant proteins can also be targeted to the periplasm by linking the recombinant protein to a secretion signal. In addition, a target protein of interest can be coexpressed in yeast such that it is localized to the plasma membrane or periplasmic space and accessible to displayed proteins. In particular embodiments, the inventors have used their method of yeast periplasmic display to screen for antibodies that bind to and modulate the function of human GPCRs (see Examples). Antibodies displayed in the periplasmic space of a yeast cell are in sufficient proximity to bind to a GPCR expressed in the cell membrane. The inventors have further developed a method for high-throughput screening of GPCRs for antagonists and agonists using periplasmic display by coupling human GPCRs to the yeast pheromone response pathway.

In order to further an understanding of the invention, a more detailed discussion is provided below regarding yeast periplasmic display and methods of using it for high-throughput screening of protein libraries.

A. Periplasmic Display of Recombinant Proteins in Yeast

In one aspect, the invention relates to the display of a protein in the periplasmic space of a yeast host cell. In some embodiments, the yeast host cell comprises a protein for display in the yeast periplasmic space, a periplasm anchor protein linked to the protein to be displayed in the periplasmic space, and a target membrane protein of interest located in the periplasmic space of the yeast host cell. In some embodiments, the yeast host cell can be used to determine if the protein to be displayed in the periplasmic space specifically binds to or affects the function of the target membrane protein of interest. The protein to be displayed in the periplasmic space of the yeast host cell can be prepared by linking a recombinant protein to a periplasm anchor protein that localizes the recombinant protein to the periplasmic space of a yeast cell. Linkage can be covalent or noncovalent. For example, a recombinant protein may be linked covalently to a periplasm anchor protein in a fusion protein. Alternatively, a recombinant protein variant may form a complex with a periplasmic anchor protein, wherein the recombinant protein and the periplasmic anchor protein are linked noncovalently by molecular binding interactions in the complex. Alternatively, a recombinant protein variant and the periplasmic anchor protein are linked covalently by a non-peptidic bond in a complex. In some embodiments, the non-peptidic bond is a disulfide bond. A protein to be displayed in the periplasmic space of the yeast host cell can also be prepared by linking the protein to be displayed to a secretion signal. In some embodiments, the genus of the yeast host cell is selected from the group consisting of *Saccharomyces, Candida, Pichia, Kluyveromyces,* and *Yarrowia*. In some embodiments, the genus of the yeast host cells is *Saccharomyces*. In some embodiments, the species of the yeast host cell is *Saccharomyces cerevisiae*.

In another aspect, the invention relates to an antibody linked to a periplasm anchor protein. In some embodiments, the antibody linked to a periplasm anchor protein further comprises an additional modification, moiety or interacting protein. In some embodiments, the additional modification is a post-translational modification. In some embodiments, the moiety is an affinity tag, epitope, label or the like. In some embodiments, the antibody is localized to a yeast host cell periplasmic space. In some embodiments, when the antibody is produced in or introduced to a yeast host cell, the antibody is localized to a yeast host cell periplasmic space. In some embodiments, the antibody is linked to a periplasm anchor protein such that the antibody is localized to the periplasmic space. Linkage of the antibody to the periplasm anchor protein can be covalent or noncovalent. For example, an antibody may be linked covalently to a periplasm anchor protein in a fusion protein. Alternatively, an antibody may form a complex with a periplasmic anchor protein, wherein the antibody and the periplasmic anchor protein are linked noncovalently by molecular binding interactions in the complex. Alternatively, an antibody and the periplasmic anchor protein are linked covalently by a non-peptidic bond in a complex. In some embodiments, the non-peptidic bond is a disulfide bond. Also provided are yeast host cells comprising an antibody as described herein. In some embodiments, the genus of the yeast host cell is selected from the group consisting of *Saccharomyces, Candida, Pichia, Kluyveromyces,* and *Yarrowia*. In some embodiments, the genus of the yeast host cells is *Saccharomyces*. In some embodiments, the species of the yeast host cell is *Saccharomyces cerevisiae*.

In another aspect, the invention relates to methods of localizing an antibody to a yeast host cell periplasmic space comprising linking the antibody to a periplasm anchor protein such that the antibody is localized to the periplasmic space. In some embodiments, the antibody is linked to a periplasm anchor protein such that the antibody is localized to the periplasmic space. Linkage of the antibody to the periplasm anchor protein can be covalent or noncovalent. For example, an antibody may be linked covalently to a periplasm anchor protein in a fusion protein. Alternatively, an antibody may form a complex with a periplasmic anchor protein, wherein the antibody and the periplasmic anchor protein are linked noncovalently by molecular binding interactions in the complex. Alternatively, an antibody and the periplasmic anchor protein are linked covalently by a non-peptidic bond in a complex. In some embodiments, the non-peptidic bond is a disulfide bond. In some embodiments, the genus of the yeast host cell is selected from the group consisting of *Saccharomyces, Candida, Pichia, Kluyveromyces*, and *Yarrowia*. In some embodiments, the genus of the yeast host cells is *Saccharomyces*. In some embodiments, the species of the yeast host cell is *Saccharomyces cerevisiae*.

In another aspect, the invention relates to methods of high-throughput screening of protein libraries for specific binding or functional characteristics by displaying proteins in the periplasmic space of yeast. A yeast periplasmic display library can be prepared by linking recombinant proteins to a periplasm anchor protein that localizes recombinant proteins to the periplasmic space of a yeast cell. Linkage can be covalent or noncovalent. For example, a recombinant protein may be linked covalently to a periplasm anchor protein in a fusion protein. Alternatively, a recombinant protein variant may form a complex with a periplasmic anchor protein, wherein the recombinant protein and the periplasmic anchor protein are linked noncovalently by molecular binding interactions in the complex. Alternatively, a recombinant protein variant and the periplasmic anchor protein are linked covalently by a non-peptidic bond in a complex. In some embodiments, the non-peptidic bond is a disulfide bond. A yeast periplasmic display library can also be prepared by linking recombinant proteins to secretion signals. In some embodiments, the genus of the yeast host cell is selected from the group consisting of *Saccharomyces, Candida, Pichia, Kluyveromyces*, and *Yarrowia*. In some embodiments, the genus of the yeast host cells is *Saccharomyces*. In some embodiments, the species of the yeast host cell is *Saccharomyces cerevisiae*.

Localization to the periplasmic space can be accomplished in a variety of ways. In certain embodiments, the recombinant protein is localized to the periplasm by linking the recombinant protein to a secretion signal that results in the recombinant protein being secreted into the extracellular space. In certain embodiments, a periplasm anchor protein comprises a signal sequence that directs transport of the periplasm anchor protein to the yeast host cell periplasm, plasma membrane, or cell wall such that a linked recombinant protein is displayed in the periplasm. For example, the periplasm anchor protein may comprise a signal sequence that directs transport of the periplasm anchor protein and the linked recombinant protein to the yeast host cell periplasm. Preferably, the periplasm anchor protein is sufficiently large that the periplasm anchor protein and the linked recombinant protein are retained in the periplasm. Alternatively, the periplasm anchor protein may be a component of a periplasmic protein complex that is sufficiently large that formation of the complex in the periplasm results in retention in the periplasm. In other embodiments, the periplasm anchor protein comprises a membrane-spanning transmembrane domain or a membrane-associated protein domain that localizes to an external face of the cell membrane such that the linked recombinant protein is projected into the periplasm. For example, a glycosylphosphatidylinositol (GPI)-anchoring domain that localizes to the plasma membrane can be used for this purpose. In one embodiment, the GPI-plasma membrane anchoring domain is a yapsin GPI plasma membrane anchoring domain such as, but not limited to, a YPS1, YPS2, YPS3, YPS4, YPS5, YPS6, or YPS7 yapsin GPI plasma membrane anchoring domain. In another embodiment, the periplasm anchor protein is a protein that binds to an inner face of the cell wall such that the displayed protein variant is projected into the periplasm. In certain embodiments, the periplasm anchor protein and the recombinant protein are covalently linked in a fusion protein variant and the periplasm anchor protein comprises a signal sequence that directs transport of the fusion protein to the yeast host cell periplasm, plasma membrane, or cell wall such that the fused protein variant is displayed in the periplasm. For example, the periplasm anchor protein may comprise a signal sequence that directs transport of the fusion protein to the yeast host cell periplasm. Preferably, the periplasm anchor protein is sufficiently large that the fusion protein is retained in the periplasm. Alternatively, the periplasm anchor protein may be a component of a periplasmic protein complex that is sufficiently large that formation of the complex in the periplasm results in retention of the fusion protein in the periplasm. In other embodiments, the periplasm anchor protein comprises a membrane-spanning transmembrane domain or a membrane-associated protein domain that localizes to an external face of the cell membrane such that the fused protein variant is projected into the periplasm. For example, a glycosylphosphatidylinositol (GPI)-anchoring domain that localizes to the plasma membrane can be used for this purpose. In one embodiment, the GPI-plasma membrane anchoring domain is a yapsin GPI plasma membrane anchoring domain such as, but not limited to, a YPS1, YPS2, YPS3, YPS4, YPS5, YPS6, or YPS7 yapsin GPI plasma membrane anchoring domain. In another embodiment, the periplasm anchor protein is a protein that binds to an inner face of the cell wall such that the displayed protein variant is projected into the periplasm. In certain embodiments, the periplasm anchor protein is a fragment of a full-length protein that retains the ability to be localized to the periplasm.

Any type of protein may be displayed in the periplasmic space of a yeast cell, including, but not limited to antibodies, antibody mimetics, aptamers, antigens, enzymes, receptors, transporters, ion channels, hormones, substrates, agonists, antagonists, or ligands. The yeast periplasmic display library presents a plurality of such proteins, which can be screened for binding and/or biological activity in the presence of a target molecule of interest. If located extracellularly, the target molecule must be able to penetrate the yeast cell wall to reach the displayed proteins for screening. In certain embodiments, a target protein of interest is coexpressed with a displayed protein variant in a yeast cell at a location accessible to the displayed protein variant (e.g., in close enough proximity for the displayed protein variant to bind to and/or modulate the activity of the target protein of interest). For example, the target protein of interest may be localized to the yeast host cell plasma membrane or periplasm near where the protein variant is displayed. In particular, this method is applicable to receptors, ion channels, transporters, and other membrane proteins which localize to the plasma membrane. Thus, yeast periplasmic display can be used to present proteins to a target membrane protein in an environment substantially similar to its native environment.

Any polypeptides included in a fusion construct, including the periplasm anchor protein and displayed protein variant may be connected directly to each other by peptide bonds or may be separated by intervening amino acid sequences or linkers. Linker amino acid sequences will typically be short, e.g., 20 or fewer amino acids (i.e., 20, 19, 18, 17, 16, 15, 14, 13, 12, 11, 10, 9, 8, 7, 6, 5, 4, 3, 2, or 1). Examples include short peptide sequences which facilitate cloning, poly-glycine linkers ($Gly_n$ where n=2, 3, 4, 5, 6, 7, 8, 9, 10 or more), histidine tags ($His_n$ where n=3, 4, 5, 6, 7, 8, 9, 10 or more), linkers composed of glycine and serine residues, wherein n=1, 2, 3, 4, 5, 6, 7, 8, 9, 10, 11, 12, 13, 14, 15 or more), GSAT, SEG, and Z-EGFR linkers. Linkers may include restriction sites, which aid cloning and manipulation. Other suitable linker amino acid sequences will be apparent to those skilled in the art. (See e.g., Argos (1990) J. Mol. Biol. 211(4):943-958; Crasto et al. (2000) Protein Eng. 13:309-312; George et al. (2002) Protein Eng. 15:871-879; Arai et al. (2001) Protein Eng. 14:529-532; and the Registry of Standard Biological Parts (partsregistry.org/Protein_domains/Linker).

Optionally, a tag may be included in fusion constructs. Tags that can be used in the practice of the invention include, but are not limited to a His-tag, a Strep-tag, a TAP-tag, an S-tag, an SBP-tag, an Arg-tag, a calmodulin-binding peptide tag, a cellulose-binding domain tag, a DsbA tag, a c-myc tag, a glutathione S-transferase tag, a FLAG tag, a HAT-tag, a maltose-binding protein tag, a NusA tag, and a thioredoxin tag.

B. Polynucleotides Encoding Periplasm-Anchored Protein Variants and Target Proteins and Library Construction Polynucleotides encoding periplasm-anchored protein variants and target proteins of interest can be produced in any number of ways, all of which are well known in the art. For example, polynucleotides can be generated using recombinant techniques, well known in the art. One of skill in the art can readily determining nucleotide sequences that encode the desired proteins using standard methodology and the teachings herein.

Oligonucleotide probes can be devised based on known gene sequences and used to probe genomic or cDNA libraries. The polynucleotides with desired sequences can then be further isolated using standard techniques and, e.g., restriction enzymes employed to truncate a gene at desired portions of the full-length sequence. Similarly, polynucleotides with sequences of interest can be isolated directly from cells and tissues containing the same, using known techniques, such as phenol extraction and the sequence further manipulated to produce desired protein variants. See, e.g., Sambrook et al., supra, for a description of techniques used to obtain and isolate DNA.

The sequences encoding protein variants can also be produced synthetically, for example, based on known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311; Stemmer et al. (1995) Gene 164:49-53.

Recombinant techniques are readily used to clone sequences encoding protein variants (e.g., antibodies) useful in the claimed invention that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, Methods Enzymol. (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. Proc. Natl. Acad. Sci. USA (1982) 79:6409.

The diversity of a display library will depend on the method of mutagenesis that is used. Cassette mutagenesis can be used to quickly generate a large number of mutations by insertion of mutagenic cassettes into a nucleic acid (see, e.g., Worrall (1994) Methods Mol. Biol. 30:199-210, Kegler-Ebo et al. (1994) Nucleic Acids Research. 22 (9):1593-1599). In addition, random mutagenesis can also be used to generate large numbers of variants for a display library. Suitable methods of random mutagenesis include, but are not limited to, error-prone PCR, rolling circle error-prone PCR, chemical mutagenesis, mutagenesis in a mutator strain with deficient DNA repair pathways, insertion mutagenesis using a transposon system, or DNA shuffling (see, e.g., McCullum et al. (2010) Methods Mol. Biol. 634:103-109, Fujii et al. (2014) Methods Mol. Biol. 1179:23-29, Muteeb (2010) Methods Mol. Biol. 634:411-419, Bose (2016) Methods Mol. Biol. 1373:111-115, Labrou (2010) Curr Protein Pept Sci. 11(1):91-100, Wilson et al. (2011) Methods Mol. Biol. 765:359-371). Such methods can be used to efficiently generate a large number of variants with modifications to a parent nucleic acid molecule. In some embodiments, a DNA library is constructed containing at least $10^6$, preferably at least $10^8$, and more preferably at least $10^{10}$ variants with unique sequences, using methods known in the art.

In some embodiments, antibody libraries are constructed for yeast periplasmic display by cloning natural antibodies from B lymphocytes obtained from blood donors. Nucleic acids encoding antibody light and heavy chains or fragments thereof containing variable domain complementarity-determining regions (e.g., Fab) can be amplified by PCR and cloned into vectors. ScFv antibodies can be generated by cloning into a vector that connects the light and heavy chains via a linker in one open reading frame. The blood donor can be of any species. In some embodiments, human blood donors are used for generation of a library of human antibodies. In other embodiments, camelid blood donors are used for generation of a library of camelid antibodies. Camelid antibodies may be derived, for example, from Dromedary camels, bactrian camels, llamas and alpacas. Such camelids produce a unique type of antibody that lacks a light chain. These heavy-chain antibodies (HCAbs) or variable domain fragments thereof (e.g., single-domain antibodies or nanobodies) can be used to construct an antibody library (see, e.g., Vincke et al. (2012) Methods Mol. Biol. 911:15-26, Krah et al. (2016) Immunopharmacol. Immunotoxicol. 38(1):21-8; herein incorporated by reference).

Once coding sequences for protein variants (e.g., antibodies) have been isolated and/or synthesized, they can be cloned into any suitable vector or replicon for expression in yeast. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III Enhancer elements may be used in association with the promoter to increase expression levels of the constructs. In certain embodiments, an expression vector comprises a promoter "operably linked" to a polynucleotide encoding a fusion protein or target protein of interest. The phrase "operably linked" or "under transcriptional control" as used herein means that the promoter is in the correct location and orientation in relation to a polynucleotide to control the initiation of transcription by RNA polymerase and expression of the fusion protein or target protein of interest.

Typically, transcription terminator/polyadenylation signals will also be present in the expression construct. Examples of such sequences include, but are not limited to, those derived from SV40, as described in Sambrook et al., supra, as well as a bovine growth hormone terminator sequence (see, e.g., U.S. Pat. No. 5,122,458). Additionally, 5'-UTR sequences can be placed adjacent to the coding sequence in order to enhance expression of the same. Such sequences may include UTRs comprising an internal ribosome entry site (IRES).

Inclusion of an IRES permits the translation of one or more open reading frames from a vector. The IRES element attracts a eukaryotic ribosomal translation initiation complex and promotes translation initiation. See, e.g., Kaufman et al., *Nuc. Acids Res.* (1991) 19:4485-4490; Gurtu et al., *Biochem. Biophys. Res. Comm.* (1996) 229:295-298; Rees et al., *BioTechniques* (1996) 20:102-110; Kobayashi et al., *BioTechniques* (1996) 21:399-402; and Mosser et al., BioTechniques (1997 22 150-161. A multitude of IRES sequences are known and include sequences derived from a wide variety of viruses, such as from leader sequences of picornaviruses such as the encephalomyocarditis virus (EMCV) UTR (Jang et al. *J. Vivol.* (1989) 63:1651-1660), the polio leader sequence, the hepatitis A virus leader, the hepatitis C virus IRES, human rhinovirus type 2 IRES (Dobrikova et al., *Proc. Natl. Acad. Sci.* (2003) 100(25): 15125-15130), an IRES element from the foot and mouth disease virus (Ramesh et al., *Nucl. Acid Res.* (1996) 24:2697-2700), a giardiavirus IRES (Garlapati et al., *J. Biol. Chem.* (2004) 279(5):3389-3397), and the like. A variety of nonviral IRES sequences will also find use herein, including, but not limited to IRES sequences from yeast, as well as the human angiotensin II type 1 receptor IRES (Martin et al., *Mol. Cell Endocrinol.* (2003) 212:51-61), fibroblast growth factor IRESs (FGF-1 IRES and FGF-2 IRES, Martineau et al. (2004) *Mol. Cell. Biol.* 24(17):7622-7635), vascular endothelial growth factor IRES (Baranick et al. (2008) Proc. Natl. Acad. Sci. U.S.A. 105(12):4733-4738, Stein et al. (1998) *Mol. Cell. Biol.* 18(6):3112-3119, Bert et al. (2006) RNA 12(6):1074-1083), and insulin-like growth factor 2 IRES (Pedersen et al. (2002) *Biochem. J.* 363(Pt 1):37-44). These elements are readily commercially available in plasmids sold, e.g., by Clontech (Mountain View, Calif.), Invivogen (San Diego, Calif.), Addgene (Cambridge, Mass.) and GeneCopoeia (Rockville, Md.). See also IRESite: The database of experimentally verified IRES structures (iresite.org). An IRES sequence may be included in a vector, for example, to express a fusion protein comprising a periplasm anchor protein fused to a protein variant for display in combination with a target protein of interest from an expression cassette.

Alternatively, a polynucleotide encoding a viral T2A peptide can be used to allow production of multiple protein products from a single vector. 2A linker peptides are inserted between the coding sequences in the multicistronic construct. The 2A peptide, which is self-cleaving, allows co-expressed proteins from the multicistronic construct to be produced at equimolar levels. 2A peptides from various viruses may be used, including, but not limited to 2A peptides derived from the foot-and-mouth disease virus, equine rhinitis A virus, *Thosea asigna* virus and porcine teschovirus-1. See, e.g., Kim et al. (2011) PLoS One 6(4): e18556, Trichas et al. (2008) BMC Biol. 6:40, Provost et al. (2007) Genesis 45(10):625-629, Furler et al. (2001) Gene Ther. 8(11):864-873; herein incorporated by reference in their entireties.

In certain embodiments, the expression construct comprises a plasmid suitable for transforming a yeast cell. Yeast expression plasmids typically contain a yeast-specific origin of replication (ORI) and nutritional selection markers (e.g., HIS3, URA3, LYS2, LEU2, TRP1, MET15, ura4+, leu1+, ade6+), antibiotic selection markers (e.g., aphA1 or ble), fluorescent markers (e.g., mCherry, green fluorescent protein), bioluminescent markers (e.g., luciferase), or other markers for selection of transformed yeast cells. The yeast plasmid may further contain components to allow shuttling between a bacterial host (e.g., *E. coli*) and yeast cells. A number of different types of yeast plasmids are available including yeast integrating plasmids (YIp), which lack an ORI and are integrated into host chromosomes by homologous recombination; yeast replicating plasmids (YRp), which contain an autonomously replicating sequence (ARS) and can replicate independently; yeast centromere plasmids (YCp), which are low copy vectors containing a part of an ARS and part of a centromere sequence (CEN); and yeast episomal plasmids (YEp), which are high copy number plasmids comprising a fragment from a 2 micron circle (a natural yeast plasmid) that allows for 50 or more copies to be stably propagated per cell.

Inclusion of regulatory sequences may also be desirable, which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. For example, a pheromone-inducible promoter, such as a PRM1 or FUS2 promoter can be used to make transcription dependent on activation of the pheromone signaling pathway. The control sequences and other regulatory sequences may be ligated to the coding sequence prior to insertion into a vector. Alternatively, the coding sequence can be cloned directly into an expression vector that already contains the control sequences and an appropriate restriction site.

In some cases, it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

In one embodiment, recombinant polynucleotides encoding protein variants are cloned into a periplasm-targeting expression vector comprising: a) a polynucleotide encoding a signal peptide; b) a cloning site suitable for in-frame insertion of a polynucleotide encoding a protein variant after the polynucleotide encoding the signal peptide; c) a polynucleotide encoding a glycophosphatidylinositol (GPI) plasma membrane anchoring domain, positioned such that the vector is capable of producing a fusion protein comprising the signal peptide and the protein variant fused to the GPI plasma membrane anchoring domain; and d) a promoter operably linked to sequences encoding the fusion protein. In certain embodiments, the GPI plasma membrane anchoring domain is a yapsin GPI plasma membrane anchoring domain such as, but not limited to, a YPS1, YPS2, YPS3, YPS4, YPS5, YPS6, or YPS7 yapsin GPI plasma membrane anchoring domain. The periplasm-targeting expression vector may further comprise a polynucleotide encoding a linker positioned in between the cloning site and the polynucleotide encoding the GPI plasma membrane anchoring domain. The cloning site may comprise one or more restriction sites. The periplasm-targeting expression vector may further comprise a selectable marker.

In some embodiments, an affinity tag, epitope, label, or the like, is added to the protein variant to allow measurement of the total display level in yeast cells. As used herein, the term "affinity tag" refers to a biomolecule, such as a polypeptide segment, that can be attached to a second biomolecule to provide for purification or detection of the second biomolecule or provide sites for attachment of the second biomolecule to a substrate. Examples of affinity tags include a poly-histidine tract, protein A (Nilsson et al. (1985) EMBO J. 4:1075; Nilsson et al. (1991) Methods Enzymol. 198:3, glutathione S transferase (Smith and Johnson (1988) Gene 67:31), Glu-Glu affinity tag (Grussenmeyer et al., (1985) PNAS USA 82:7952), substance P, FLAG peptide (Hopp et al. (1988) Biotechnology 6:1204), streptavidin binding peptide, or other antigenic epitope or binding domain, and the like, (Ford et al. (1991) Protein Expression and Purification 2:950), all of which are herein incorporated by reference. As used herein, a "label" is a molecule or atom which can be conjugated to a biomolecule to render the biomolecule or a form of the biomolecule, such as a conjugate, detectable or measurable. Examples of labels include fluorescent agents, bioluminescent proteins, photoactive agents, radioisotopes, paramagnetic ions, chelators, and the like.

An expression vector is used to transform an appropriate yeast host cell. A number of yeast hosts are known in the art, including but not limited to, *Saccharomyces arboricolus, Saccharomyces bayanus, Saccharomyces boulardii, Saccharomyces bulderi, Saccharomyces cariocanus, Saccharomyces cariocus, Saccharomyces cerevisiae, Saccharomyces chevalieri, Saccharomyces dairenensis, Saccharomyces ellipsoideus, Saccharomyces eubayanus, Saccharomyces exiguus, Saccharomyces florentinus, Saccharomyces fragilis, Saccharomyces kluyveri, Saccharomyces kudriavzevii, Saccharomyces martiniae, Saccharomyces mikatae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum, Saccharomyces zonatus, Candida albicans, Candida ascalaphidarum, Candida amphixiae, Candida antarctica, Candida argentea, Candida atlantica, Candida atmosphaerica, Candida auris, Candida blattae, Candida bromeliacearum, Candida carpophila, Candida carvajalis, Candida cerambycidarum, Candida chauliodes, Candida corydali, Candida dosseyi, Candida dubliniensis, Candida ergatensis, Candida fructus, Candida glabrata, Candida fermentati, Candida guilliermondii, Candida haemulonii, Candida humilis, Candida insectamens, Candida insectorum, Candida intermedia, Candida jeffresii, Candida kefyr, Candida keroseneae, Candida krusei, Candida lusitaniae, Candida lyxosophila, Candida maltosa, Candida marina, Candida membranifaciens, Candida mogii, Candida oleophila, Candida oregonensis, Candida parapsilosis, Candida quercitrusa, Candida rugosa, Candida sake, Candida shehatea, Candida temnochilae, Candida tenuis, Candida theae, Candida tolerans, Candida tropicalis, Candida tsuchiyae, Candida sinolaborantium, Candida sojae, Candida subhashii, Candida viswanathii, Candida utilis, Candida ubatubensis, Candida zemplinina, Pichia farinosa, Pichia anomala, Pichia heedii, Pichia guilliermondii, Pichia kluyveri, Pichia membranifaciens, Pichia norvegensis, Pichia ohmeri, Pichia pastoris, Pichia methanolica, Pichia subpelliculosa, Kluyveromyces aestuarii, Kluyveromyces africanus, Kluyveromyces bacillisporus, Kluyveromyces blattae, Kluyveromyces dobzhanskii, Kluyveromyces hub eiensis, Kluyveromyces lactis, Kluyveromyces lodderae, Kluyveromyces marxianus, Kluyveromyces nonfermentans, Kluyveromyces piceae, Kluyveromyces sinensis, Kluyveromyces thermotolerans, Kluyveromyces waltii, Kluyveromyces wickerhamii, Kluyveromyces yarrowii, Yarrowia bubula, Yarrowia deformans, Yarrowia hpolytica, Yarrowia porcina,* and *Yarrowia yakushimensis,* which will find use with the present expression constructs. In some embodiments, the yeast is a *Saccharomyces* species. In some embodiments, the yeast is *Saccharomyces cerevisiae*.

In order to effect expression of sense or antisense gene constructs, the expression construct must be delivered into a yeast cell. This delivery may be accomplished in vitro using laboratory procedures for transforming yeast cells well-known in the art, such as spheroplast transformation, alkaline ion treatment (e.g., $Cs^+$ or $Li^+$), electroporation, trans-kingdom conjugation, electroporation, and biolistic and glass bead methods (see, e.g., Kawai et al. (2010) Bioeng. Bugs. 1(6):395-403, Gietz et al. (1995) Yeast 11(4):355-360, Gietz et al. (2007) Nat. Protoc. 2(1):38-41, Hinnen et al. (1978) Proc. Natl. Acad. Sci. USA 75:1929-1933, Avery et al. (1995) Mol. Med. 1(4):344-365, Ito et al. (1983) J. Bacteriol. 153:163-168, Johnston et al. (1988) Science 240: 1538-1541, Dohmen et al. (1991) Yeast 7(7):691-246, Hayama et al. (2002) J. Biosci. Bioeng. 94(2):166-171, and Wang et al. (2001) Crit. Rev. Biotechnol. 21(3):177-218; herein incorporated by reference).

Once an expression construct has been delivered into the cell, the nucleic acid encoding the gene of interest may be positioned and expressed at different sites. In certain embodiments, the nucleic acid encoding the gene may be stably integrated into the genome of the cell via homologous recombination. This integration may be in the cognate location and orientation (gene replacement), within a gene (gene disruption), or in a random, non-specific location (gene augmentation). Integration of a construct at a target locus that disrupts a gene may be acceptable as long as the gene disruption does not interfere with cell growth or screening of the yeast periplasmic display library (e.g., avoid disruption of pheromone response if used in screening) In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments, the expression construct may simply consist of naked recombinant DNA or plasmids. Transfer of the construct may be performed by any of the methods mentioned above which physically or chemically permeabilize the cell membrane.

In still another embodiment, a naked DNA expression construct may be transferred into cells by particle bombardment. This method depends on the ability to accelerate DNA-coated microprojectiles to a high velocity allowing them to pierce yeast cell walls and membranes and enter cells without killing them (Armaleo et al. (1990) Curr. Genet. 17(2):97-103). Several devices for accelerating small particles have been developed. One such device relies on a high voltage discharge to generate an electrical current, which in turn provides the motive force (Yang et al. (1990) Proc. Natl. Acad. Sci. USA 87:9568-9572). The microprojectiles may consist of biologically inert substances, such as tungsten or gold beads.

In some embodiments, a collection of linear DNA molecules encoding protein variants are generated. Rather than cloning the linear DNA molecules into a vector prior to transformation, the yeast cells are transformed with an empty vector together with the collection of linear DNA molecules encoding the protein variants, which subsequently integrate into the vector in vivo, e.g., by homologous recombination in the yeast host cells.

C. Kits

A kit may include a yeast periplasmic display library, as described herein, or agents for preparing a yeast periplasmic display library, such as suitable vectors for cloning nucleic acids encoding protein variants for production of protein variants linked to a periplasm anchor protein, yeast cells, transfection agents, media suitable for growing yeast cells, agents for positive and negative selection of cells, and other reagents that are required. Instructions (e.g., written, CD-ROM, DVD, Blu-ray, flash drive, digital download, etc.) for production and/or screening of a yeast periplasmic display library as described herein usually will be included in the kit.

A kit may include a yeast periplasmic display library, as described herein, or agents for preparing a yeast periplasmic display library, such as suitable vectors for cloning nucleic acids encoding protein variants for production of fusions with a periplasm anchor protein, yeast cells, transfection agents, media suitable for growing yeast cells, agents for positive and negative selection of cells, and other reagents that are required. Instructions (e.g., written, CD-ROM, DVD, Blu-ray, flash drive, digital download, etc.) for production and/or screening of a yeast periplasmic display library as described herein usually will be included in the kit.

In one embodiment, the kit comprises a periplasm-targeting expression vector comprising: a) a polynucleotide encoding a signal peptide; b) a cloning site suitable for in-frame insertion of a polynucleotide encoding a protein variant (e.g., antibody) after the polynucleotide encoding the signal peptide; c) a polynucleotide encoding a glycophosphatidylinositol (GPI) plasma membrane anchoring domain, positioned such that the vector is capable of producing a fusion protein comprising the signal peptide and the protein variant fused to the GPI plasma membrane anchoring domain; and d) a promoter operably linked to sequences encoding the fusion protein. In another embodiment, the signal peptide comprises a prepro-alpha-factor signal sequence. In certain embodiments, the GPI plasma membrane anchoring domain is a yapsin GPI plasma membrane anchoring domain such as, but not limited to, a YPS1, YPS2, YPS3, YPS4, YPS5, YPS6, or YPS7 yapsin GPI plasma membrane anchoring domain. In another embodiment, the periplasm-targeting expression vector further comprises a polynucleotide encoding a linker, wherein said polynucleotide encoding the linker is positioned in between the cloning site and the polynucleotide encoding the GPI plasma membrane anchoring domain. The linker may further comprise a tag. In another embodiment, the periplasm-targeting expression vector further comprises a selectable marker. In another embodiment, the cloning site comprises one or more restriction sites.

In another embodiment, the kit includes a yeast periplasmic display library comprising a plurality of yeast host cells, each yeast host cell comprising: a) a fusion protein comprising a periplasm anchor protein fused to a protein variant (e.g., antibody) for display in the yeast host cell periplasmic space, wherein the displayed protein variant is different in each yeast host cell such that the plurality of yeast host cells displays a plurality of protein variants; b) a target G-protein coupled receptor (GPCR) of interest, wherein the target GPCR of interest is located in the yeast host cell plasma membrane and accessible to the protein variant displayed in the yeast host cell periplasmic space; and c) an engineered Gα subunit capable of being activated by the GPCR, wherein the activated engineered Gα subunit is capable of activating a detectable pheromone response in the yeast host cell. In certain embodiments, the engineered Gα subunit is a chimeric G protein alpha (Gα) subunit comprising an N-terminal domain of a yeast Gα subunit and a C-terminal domain of an exogenous Gα subunit. For example, the yeast Gα subunit may belong to a Gαi, Gαq, Gαs, or Gαo family G protein. In the chimeric Gα subunit, at least five C-terminal residues of a yeast Gα subunit may be replaced with corresponding C-terminal residues of a mammalian Gα subunit such that the chimeric Gα subunit is capable of being activated by a mammalian GPCR. In some embodiments, at least 20 C-terminal residues of the yeast Gα subunit are replaced with corresponding C-terminal residues of the mammalian Gα subunit such that the chimeric Gα subunit is capable of being activated by the mammalian GPCR. In another embodiment, the chimeric Gα subunit comprises at least 41 N-terminal residues of the yeast Gα subunit. In certain embodiments, the mammalian GPCR is a mouse GPCR. In certain embodiments, the mammalian GPCR is a human GPCR selected from the group consisting of CXCR4, CXCR5, SSTR2, MOR, AVPR2, FPR2/ALX, ADORA2A, CHRM3, CGRP2, CCR2, CCR4, CCR5, CHRM4, PAC1, b2AR, CXCR2, CYSLTR2, KSHV vGPCR, PKR1, PKR2, CB1, CB2, A3AR, and AT1R.

In another embodiment, the kit includes a yeast periplasmic display library comprising: a plurality of yeast host cells, each yeast host cell comprising a fusion protein comprising a periplasm anchor protein fused to a protein variant for display, wherein the periplasm anchor protein is sufficiently large that the fusion protein is retained in the periplasm, and the displayed protein variant is different in each yeast host cell such that the plurality of yeast host cells displays a plurality of protein variants.

In another embodiment, the kit includes a yeast periplasmic display library comprising: a plurality of yeast host cells, each yeast host cell comprising a fusion protein comprising a protein variant for display linked to a target membrane protein of interest, wherein the displayed protein variant is different in each yeast host cell such that the plurality of yeast host cells displays a plurality of protein variants with the target membrane protein of interest.

D. Applications

The present invention may be broadly applied in screening for proteins that perform useful or desired functions including binding, catalysis, assembly, transport, and the like. For example, yeast periplasmic display can be used in identifying agonists and antagonists for receptors, engineering therapeutic proteins and antibodies, identifying protein-protein interactions, and epitope mapping.

Yeast periplasmic display is particularly well-suited for screening a protein library for candidates that bind to and/or modulate the function of a target protein that is a membrane protein, such as a receptor, an ion channel, or a transporter. Localization of a protein to the membrane makes it accessible to the displayed protein variants in the periplasmic space (e.g., in close enough proximity for a displayed protein variant to bind to the target protein of interest).

In certain embodiments, activation of the target protein of interest increases growth of the yeast host cells. In this case, the yeast periplasmic display library may be screened for an agonist of the target protein of interest by culturing at least a subset of the yeast host cells of the yeast periplasmic display library in a media, wherein growth of a yeast host cell in the media indicates that the protein variant displayed in the yeast host cell is an agonist of the target protein of interest.

In other embodiments, activation of the target protein of interest decreases growth of the yeast host cells. In this case, the yeast periplasmic display library may be screened for an antagonist of the target protein of interest by culturing at least a subset of the yeast host cells of the yeast periplasmic display library in a media, wherein growth of a yeast host cell in the media indicates that the protein variant displayed in the yeast host cell is an antagonist of the target protein of interest.

In certain embodiments, each yeast host cell further comprises a reporter system comprising a reporter gene operably linked to an inducible promoter that is activated when the target protein of interest is activated to allow detection of increases or decreases in activity of the target protein of interest upon binding of the displayed protein variant to the target protein of interest. For example, the reporter gene may be a nutritional marker (e.g., HIS3, HIS7, ARG6, LEU2, URA3, and TRP1), antibiotic resistance marker (e.g., confers resistance to an antibiotic such as geneticin (e.g., aphA1), zeocin (e.g., ble), hygromycin B, nourseothricin, or bialaphos), fluorescent marker (e.g., a green fluorescent protein, a red fluorescent protein, a blue fluorescent protein, a cyan fluorescent protein, a yellow fluorescent protein, and an orange fluorescent protein), bioluminescent marker (e.g., luciferase and aequorin), or counter-selectable marker (e.g., CAN1, URA3, MET15, TRP1, and TK).

For example, positive selection (i.e., selection for the activation of expression of the reporter gene) can be used to detect increases in activity of the target membrane protein of interest upon binding of the displayed protein variant to the target membrane protein of interest. Expression of a nutritional marker can be detected, for example, by growth of the yeast host cells in a nutrient-deficient selection media. Expression of an antibiotic resistance marker can be detected, for example, by growth of the yeast host cells in a selection media comprising an antibiotic. Expression of a fluorescent marker can be detected, for example, by fluorescence emitted by the yeast host cells. Expression of a bioluminescent marker can be detected, for example, by bioluminescence emitted by the yeast host cells.

Alternatively, counterselection (i.e., growth-based selection for the loss of expression of the reporter gene) can be used to detect decreases in activity of the target membrane protein of interest upon binding of the displayed protein variant to the target membrane protein of interest. A counter-selectable marker may kill cells by inducing apoptosis, converting a nontoxic drug to a toxic compound, or transporting a toxic molecule into a cell. Counterselection can be performed by culturing the yeast host cells in a media comprising an agent that selectively kills cells expressing the counter-selectable marker. Exemplary counter selectable markers include CAN1 (counterselection with canavanine), URA3 (counterselection with 5-fluoro-orotic acid (5-FOA)), MET15 (counterselection with methylmercury), TRP1 (counterselection with 5-fluoroanthranilic acid (5-FAA)), and human Herpes virus thymidine kinase TK (counterselection with floxuridine (FUDR)).

In particular, a yeast periplasmic display library may be used for screening for antibodies that bind to and modulate the function of a GPCR. In some embodiments, a GPCR in the yeast host cell is replaced with a mammalian GPCR, e.g., human GPCR. In some embodiments, the yeast host cell expresses a mammalian GPCR, e.g., human GPCR, and the endogenous yeast GPCR. In some embodiments, antagonists and agonists are identified using a reporter system that couples the response of a GPCR to binding of a displayed antibody to levels of yeast pheromone secretion (see Examples). For this purpose, the yeast host cell can be genetically modified to express an engineered Gα subunit capable of being activated by the GPCR, wherein the activated engineered Gα subunit is capable of activating a detectable pheromone response in the yeast host cell. In certain embodiments, the engineered Gα subunit is a chimeric G protein alpha (Gα) subunit comprising an N-terminal domain of a yeast Gα subunit and a C-terminal domain of an exogenous Gα subunit. For example, the yeast Gα subunit may belong to a Gαi, Gαq, Gαs, or Gαo family G protein. In the chimeric Gα subunit, at least five C-terminal residues of a yeast Gα subunit may be replaced with corresponding C-terminal residues of a mammalian Gα subunit such that the chimeric Gα subunit is capable of being activated by a mammalian GPCR. In some embodiments, at least 20 C-terminal residues of the yeast Gα subunit are replaced with corresponding C-terminal residues of the mammalian Gα subunit such that the chimeric Gα subunit is capable of being activated by the mammalian GPCR. In another embodiment, the chimeric Gα subunit comprises at least 41 N-terminal residues of the yeast Gα subunit. Exemplary mammalian Gα subunits include G alpha-S, G alpha-I, G alpha-O, G alpha-T, G alpha-Z, G alpha-Q, G alpha-11, G alpha-12, G alpha-13, and transducin.

In particular, Δfar1, Δsst2, Δste14, Δste3 or Δmat yeast strains are useful in screening for antagonists and agonists of GPCRs. A Δmat strain may comprise, for example, a deleted or inactivated MATα locus or a deleted or inactivated MATα locus. The yeast host cell may further comprise a modified CLN3 protein comprising a C-terminal truncation that increases abundance of CLN3 in the yeast host cell compared to a wild-type CLN3 protein. For example, the modified CLN3 protein may retain at least N-terminal amino acids 1-387 or 1-408 of the wild-type CLN3 protein, or any number of N-terminal amino acids within these ranges, such as 1-388, 1-389, 1-390, 1-391, 1-392, 1-393, 1-394, 1-395, 1-396, 1-397, 1-398, 1-399, 1-400, 1-401, 1-402, 1-403, 1-404, 1-405, 1-406, 1-407, or 1-408, wherein the C-terminal truncation comprises a deletion of all or some of the remaining residues of the wild-type CLN3 protein. The yeast host cells used to prepare a periplasmic display library may be haploid or diploid. Exemplary yeast strains designed for use in antagonist and agonist selection are described in Examples 2 and 5, respectively.

In certain embodiments, the yeast host cell is a FAR1 strain, wherein inhibition of the pheromone response by an antibody acting as an antagonist that binds to an inhibits the GPCR in the yeast host cell results in cessation of cell cycle arrest and growth of the yeast host cell. In other embodiments, the yeast host cell is a Δfar1 strain comprising a pheromone-inducible PRM1 promoter operably linked to a reporter gene, wherein activation of the pheromone response by an antibody acting as an agonist that binds to and activates the GPCR in the yeast host cell results in increased expression of the reporter gene.

Any type of GPCR from any species may be screened using periplasmic display as described herein. In some embodiments, the target GPCR of interest is a mammalian GPCR (e.g., from human or nonhuman primate, rodent, laboratory animal, livestock). For example, the mammalian GPCR may be a human GPCR (e.g., CXCR4, CXCR5, SSTR2, MOR, AVPR2, FPR2/ALX, ADORA2A, CHRM3, CGRP2, CCR2, CCR4, CCR5, CHRM4, PAC1, b2AR, CXCR2, CYSLTR2, KSHV vGPCR, PKR1, PKR2, CB1, CB2, A3AR, and AT1R). The target GPCR of interest may have constitutive ligand-independent activity. Alternatively, a ligand may be added to activate the target GPCR of interest during screening for agonists or antagonists. In some embodiments, the yeast host cell expresses the target GPCR of interest, e.g., human GPCR of interest, and the endogenous yeast GPCR.

In some embodiments, the protein variants are antibodies. Any type of antibody may be screened using yeast periplasmic display by the methods described herein, including monoclonal antibodies, hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911: 15-26; dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276, 169, published 21 Sep. 1994); and, any functional fragments obtained from such molecules, wherein such fragments retain specific-binding properties of the parent antibody molecule.

In other embodiments, the protein variants are aptamers. Aptamers may be isolated from a combinatorial library and improved by directed mutation or repeated rounds of mutagenesis and selection. For a description of methods of producing aptamers, see, e.g., *Aptamers: Tools for Nanotherapy and Molecular Imaging* (R. N. Veedu ed., Pan Stanford, 2016), *Nucleic Acid and Peptide Aptamers: Methods and Protocols* (Methods in Molecular Biology, G. Mayer ed., Humana Press, 2009), *Aptamers Selected by Cell-SELEX for Theranostics* (W. Tan, X. Fang eds., Springer, 2015), Cox et al. (2001) Bioorg. Med. Chem. 9(10):2525-2531; Cox et al. (2002) Nucleic Acids Res. 30(20): e108, Kenan et al. (1999) Methods Mol. Biol. 118:217-231; Platella et al. (2016) Biochim. Biophys. Acta November 16 pii: S0304-4165(16)30447-0, and Lyu et al. (2016) Theranostics 6(9):1440-1452; herein incorporated by reference in their entireties.

In yet other embodiments, the protein variants are antibody mimetics. Any type of antibody mimetic may be used, including, but not limited to, affibody molecules (Nygren (2008) FEBS J. 275 (11):2668-2676), affilins (Ebersbach et al. (2007) J. Mol. Biol. 372 (1):172-185), affimers (Johnson et al. (2012) Anal. Chem. 84 (15):6553-6560), affitins (Krehenbrink et al. (2008) J. Mol. Biol. 383 (5):1058-1068), alphabodies (Desmet et al. (2014) Nature Communications 5:5237), anticalins (Skerra (2008) FEBS J. 275 (11):2677-2683), avimers (Silverman et al. (2005) Nat. Biotechnol. 23 (12):1556-1561), darpins (Stumpp et al. (2008) Drug Discov. Today 13 (15-16):695-701), fynomers (Grabulovski et al. (2007) J. Biol. Chem. 282 (5):3196-3204), and monobodies (Koide et al. (2007) Methods Mol. Biol. 352:95-109).

In addition, directed evolution with multiple rounds of mutagenesis and screening by yeast periplasmic display may be performed to enrich libraries for protein variants (e.g., antibodies) that bind with high affinity to a target protein of interest. Directed evolution may be particularly useful for improving the binding characteristics of candidates with desired functional activities but weak binding affinities.

III. EXEMPLARY EMBODIMENTS

Among the embodiments provided herein are:

1. A yeast periplasmic display library comprising a plurality of yeast host cells, wherein each yeast host cell comprises:

a) an antibody for display in the yeast host cell periplasmic space, wherein the displayed antibody is different in each yeast host cell such that the plurality of yeast host cells displays a plurality of antibodies;

b) a periplasm anchor protein, wherein the periplasm anchor protein is linked to the antibody such that the antibody is displayed in the periplasmic space; and c) a target membrane protein of interest, wherein the membrane protein of interest is located in the yeast host cell plasma membrane and accessible to the antibody displayed in the yeast host cell periplasmic space.

2. The yeast periplasmic display library of embodiment 1, wherein the antibody and the periplasm anchor protein are noncovalently linked together by molecular binding interactions in a complex or are linked by a covalent non-peptidic bond in a complex.

3. The yeast periplasmic display library of embodiment 1, wherein the antibody and the periplasm anchor protein are covalently linked together in a fusion protein.

4. The yeast periplasmic display library of any one of embodiments 1-3, wherein the periplasm anchor protein further comprises a signal sequence that directs transport of the periplasm anchor protein to the yeast host cell periplasm, plasma membrane, or cell wall such that the antibody is displayed in the periplasm.

5. The yeast periplasmic display library of any one of embodiments 1-3, wherein the periplasm anchor protein comprises a membrane-spanning transmembrane domain or a membrane associated protein domain that projects the antibody into the periplasm.

6. The yeast periplasmic display library of embodiment 5, wherein the membrane associated protein domain is a glycosylphosphatidylinositol (GPI)-plasma membrane anchoring domain.

7. The yeast periplasmic display library of embodiment 6, wherein the GPI-plasma membrane anchoring domain is a yapsin GPI plasma membrane anchoring domain.

8. The yeast periplasmic display library of embodiment 7, wherein the yapsin GPI plasma membrane anchoring domain is a YPS1, YPS2, YPS3, YPS4, YPS5, YPS6, or YPS7 yapsin GPI plasma membrane anchoring domain.

9. The yeast periplasmic display library of embodiment 2, wherein the periplasm anchor protein is a protein that binds to an inner face of the cell wall such that the antibody is projected into the periplasm.

10. The yeast periplasmic display library of embodiment 3, wherein the periplasm anchor protein is a protein that binds to an inner face of the cell wall that projects the fusion protein into the periplasm.

11. The yeast periplasmic display library of embodiment 2, wherein the periplasm anchor protein is sufficiently large such that the periplasm anchor protein and linked antibody are retained in the periplasm.

12. The yeast periplasmic display library of embodiment 3, wherein the periplasm anchor protein is sufficiently large that the fusion protein is retained in the periplasm.

13. A yeast periplasmic display library comprising a plurality of yeast host cells, wherein each yeast host cell comprises:
   a) an antibody for display in the yeast host cell periplasmic space, wherein the displayed antibody is different in each yeast host cell such that the plurality of yeast host cells displays a plurality of antibodies, wherein the antibody is linked to a signal sequence that directs transport of the antibody to the yeast host cell periplasm, plasma membrane or cell wall, such that the antibody is displayed in the yeast host cell periplasmic space; and
   b) a target membrane protein of interest, wherein the membrane protein of interest is located in the yeast host cell plasma membrane and accessible to the antibody displayed in the yeast host cell periplasmic space.

14. The yeast periplasmic display library of any one of embodiments 1-13, further comprising a reporter system comprising a reporter gene operably linked to an inducible promoter that is activated when the target membrane protein of interest is activated to allow detection of increases or decreases in activity of the target membrane protein of interest upon binding of the antibody to the target membrane protein of interest.

15. The yeast periplasmic display library of embodiment 14, wherein the reporter gene is a nutritional marker, antibiotic resistance marker, fluorescent marker, bioluminescent marker, or counter-selectable marker.

16. The yeast periplasmic display library of embodiment 15, wherein the nutritional marker is selected from the group consisting of HIS3, HIS7, ARG6, LEU2, URA3, and TRP1.

17. The yeast periplasmic display library of embodiment 15, wherein the antibiotic resistance marker confers resistance to an antibiotic selected from the group consisting of geneticin, zeocin, hygromycin B, nourseothricin, and bialaphos.

18. The yeast periplasmic display library of embodiment 15, wherein the fluorescent marker is selected from the group consisting of a green fluorescent protein, a red fluorescent protein, a blue fluorescent protein, a cyan fluorescent protein, a yellow fluorescent protein, and an orange fluorescent protein.

19. The yeast periplasmic display library of embodiment 15, wherein the bioluminescent marker is luciferase or aequorin.

20. The yeast periplasmic display library of embodiment 15, wherein the counter-selectable marker is selected from the group consisting of CAN1, URA3, MET15, TRP1, and TK.

21. The yeast periplasmic display library of embodiment 14, wherein the reporter gene is a selectable marker such that said increases in activity of the target membrane protein of interest upon binding of the antibody to the target membrane protein of interest are detectable by growth of the yeast host cells on a positive selection media.

22. The yeast periplasmic display library of embodiment 14, wherein the reporter gene is a counter-selectable marker such that said decreases in activity of the target membrane protein of interest upon binding of the antibody to the target membrane protein of interest are detectable by growth of the yeast host cells on a negative selection media.

23. The yeast periplasmic display library of any one of embodiments 1-22, wherein the target membrane protein of interest is selected from the group consisting of a receptor, an ion channel, and a transporter.

24. The yeast periplasmic display library of embodiment 23, wherein the receptor is a G-protein coupled receptor (GPCR).

25. The yeast periplasmic display library of embodiment 24, wherein the GPCR is an exogenous GPCR.

26. The yeast periplasmic display library of embodiment 25, wherein the yeast host cells further comprise an endogenous GPCR.

27. The yeast periplasmic display library of embodiment 25 or 26, further comprising an engineered Gα subunit capable of being activated by the exogenous GPCR, wherein the activated engineered Gα subunit is capable of activating a detectable pheromone response in the yeast host cell.

28. The yeast periplasmic display library of embodiment 27, wherein the engineered Gα subunit is a chimeric G protein alpha (Gα) subunit comprising an N-terminal domain of a yeast Gα subunit and a C-terminal domain of an exogenous Gα subunit.

29. The yeast periplasmic display library of embodiment 28, wherein the yeast Gα subunit belongs to a Gαi, Gαq, Gαs, or Gαo family G protein.

30. The yeast periplasmic display library of any one of embodiments 25-29, wherein the exogenous GPCR is a mammalian GPCR.

31. The yeast periplasmic display library of embodiment 30, wherein at least five C-terminal residues of the yeast Gα subunit are replaced with corresponding C-terminal residues of a mammalian Gα subunit such that the chimeric Gα subunit is capable of being activated by the mammalian GPCR.

32. The yeast periplasmic display library of embodiment 31, wherein at least 20 C-terminal residues of the yeast Gα subunit are replaced with corresponding C-terminal residues of the mammalian Gα subunit such that the chimeric Gα subunit is capable of being activated by the mammalian GPCR.

33. The yeast periplasmic display library of embodiment 31 or 32, wherein the mammalian Gα subunit is selected from the group consisting of G alpha-S, G alpha-I, G alpha-O, G alpha-T, G alpha-Z, G alpha-Q, G alpha-11, G alpha-12, G alpha-13, and transducin.

34. The yeast periplasmic display library of any one of embodiments 28-33, wherein the chimeric Gα subunit comprises at least 41 N-terminal residues of the yeast Gα subunit.

35. The yeast periplasmic display library of any one of embodiments 30-34, wherein the mammalian GPCR is a human GPCR.

36. The yeast periplasmic display library of embodiment 35, wherein the human GPCR is selected from the group consisting of CXCR4, CXCR5, SSTR2, MOR, AVPR2, FPR2/

ALX, ADORA2A, CHRM3, CGRP2, CCR2, CCR4, CCR5, CHRM4, PAC1, b2AR, CXCR2, CYSLTR2, KSHV vGPCR, PKR1, PKR2, CB1, CB2, A3AR, and AT1R.

37. The yeast periplasmic display library of any one of embodiments 24-36, wherein the GPCR target membrane protein of interest has constitutive ligand-independent activity.

38. The yeast periplasmic display library of any one of embodiments 24-37, wherein the yeast host cell is a FAR1 strain for selection of antibody antagonists of the GPCR target membrane protein of interest.

39. The yeast periplasmic display library of any one of embodiments 24-36, wherein the yeast host cell is a Δfar1 strain comprising a pheromone-inducible PRM1 promoter operably linked to a reporter gene for selection of antibody agonists of the GPCR target membrane protein of interest.

40. The yeast periplasmic display library of any one of embodiments 1-39, wherein the antibodies are selected from the group consisting of monoclonal antibodies, chimeric antibodies, humanized antibodies, nanobodies, recombinant fragments of antibodies, Fab fragments, Fab' fragments, F(ab')$_2$ fragments, F$_v$ fragments, and scFv fragments.

41. The yeast periplasmic display library of any one of embodiments 1-40, wherein the target membrane protein of interest comprises a mutation that increases or decreases its activity.

42. The yeast periplasmic display library of any one of embodiments 1-40, wherein the yeast host cell is a Δfar1, Δsst2, Δste14, Δste3, or Δmat strain.

43. The yeast periplasmic display library of embodiment 42, wherein the yeast host cell is a Δmat strain comprising a deleted or inactivated MATα locus or a deleted or inactivated MATα locus.

44. The yeast periplasmic display library of any one of embodiments 1-43, wherein the yeast host cell further comprises a modified CLN3 protein comprising a C-terminal truncation that increases abundance of CLN3 in the yeast host cell compared to a wild-type CLN3 protein.

45. The yeast periplasmic display library of embodiment 44, wherein the modified CLN3 protein retains at least N-terminal amino acids 1-387 of the wild-type CLN3 protein.

46. The yeast periplasmic display library of embodiment 44, wherein the modified CLN3 protein retains at least N-terminal amino acids 1-408 of the wild-type CLN3 protein.

47. The yeast periplasmic display library of any one of embodiments 1-46, wherein the yeast host cell is a haploid or diploid yeast host cell.

48. A method of making the yeast periplasmic display library of embodiment 1, the method comprising:
   a) providing a first plurality of recombinant polynucleotides encoding the antibodies for display in the yeast host cell periplasmic space, wherein the displayed antibody is different in each yeast host cell such that the plurality of yeast host cells displays a plurality of antibodies;
   b) providing a second recombinant polynucleotide encoding the periplasm anchor protein, wherein the periplasm anchor protein is linked to the antibody such that the antibody is displayed in the periplasmic space;
   c) transfecting the plurality of yeast host cells with the first plurality of recombinant polynucleotides and the second recombinant polynucleotide;
   d) transfecting the plurality of yeast host cells with a recombinant polynucleotide encoding the target membrane protein of interest; and
   e) culturing the plurality of yeast host cells under conditions that permit expression of the antibodies, the periplasm anchor protein and the target membrane protein of interest, wherein each yeast host cell displays a different antibody in the periplasmic space and the target membrane protein of interest localizes to the plasma membrane, such that the yeast periplasmic display library of embodiment 1 is produced.

49. The method of embodiment 48, wherein the recombinant polynucleotides encoding the antibodies or the recombinant polynucleotide encoding the periplasm anchor protein or the target membrane protein of interest are provided by expression vectors.

50. The method of embodiment 48, wherein the recombinant polynucleotides encoding the antibodies or the recombinant polynucleotide encoding the periplasm anchor protein or the target membrane protein of interest are integrated into the yeast host cell genome at a target locus.

51. A method of making the yeast periplasmic display library of embodiment 3, the method comprising:
   a) providing a plurality of recombinant polynucleotides encoding fusion proteins, wherein each recombinant polynucleotide encodes a different fusion protein comprising the periplasm anchor protein linked to a different antibody for display;
   b) transfecting the plurality of yeast host cells with the plurality of recombinant polynucleotides encoding the fusion proteins;
   c) transfecting the plurality of yeast host cells with a recombinant polynucleotide encoding the target membrane protein of interest; and
   d) culturing the plurality of yeast host cells under conditions that permit expression of the fusion proteins and the target membrane protein of interest, wherein each yeast host cell displays a different antibody in the periplasmic space and the target membrane protein of interest localizes to the plasma membrane, such that the yeast periplasmic display library of embodiment 3 is produced.

52. The method of embodiment 51, wherein the recombinant polynucleotides encoding the fusion proteins or the recombinant polynucleotide encoding the target membrane protein of interest are provided by expression vectors.

53. The method of embodiment 51, wherein the recombinant polynucleotides encoding the fusion proteins or the target membrane protein of interest are integrated into the yeast host cell genome at a target locus.

54. The method of any one of embodiment 48-53, wherein the target membrane protein of interest is selected from the group consisting of a receptor, an ion channel, and a transporter.

55. The method of embodiment 54, wherein the receptor is a G-protein coupled receptor (GPCR).

56. The method of any one of embodiments 48-55, further comprising introducing into the plurality of yeast host cells a recombinant polynucleotide encoding an engineered Gα subunit capable of being activated by the GPCR, wherein the activated engineered Gα subunit is capable of activating a detectable pheromone response in the yeast host cell.

57. The method of embodiment 56, wherein the engineered Gα subunit is a chimeric G protein alpha (Gα) subunit comprising an N-terminal domain of a yeast Gα subunit and a C-terminal domain of an exogenous Gα subunit.

58. The method of embodiment 57, wherein the yeast Gα subunit belongs to a Gαi, Gαq, Gαs, or Gαo family G protein.

59. The method of embodiment 57 or 58, wherein the exogenous Gα subunit is a mammalian Gα subunit.

60. The method of embodiment 59, wherein at least five C-terminal residues of the yeast Gα subunit are replaced with corresponding C-terminal residues of a mammalian Gα subunit such that the chimeric Gα subunit is capable of being activated by the mammalian GPCR.

61. The method of embodiment 60, wherein at least 20 C-terminal residues of the yeast Gα subunit are replaced with corresponding C-terminal residues of the mammalian Gα subunit such that the chimeric Gα subunit is capable of being activated by the mammalian GPCR.

62. The method of any one of embodiments 55-61, wherein the yeast host cell is a FAR1 strain for selection of antibody antagonists of the target GPCR of interest.

63. The method of any one of embodiments 55-61, wherein the yeast host cell is a Δfar1 strain comprising a pheromone-inducible PRM1 promoter operably linked to a reporter gene for selection of antibody agonists of the GPCR.

64. A method of screening the yeast periplasmic display library of embodiment 14 for an antibody that modulates activity of the target membrane protein of interest, the method comprising culturing at least a subset of the yeast host cells of the yeast periplasmic display library of embodiment 14 in a selection media; and detecting expression of the reporter gene, wherein increased expression of the reporter gene indicates that the antibody increases activity of target membrane protein of interest and decreased expression of the reporter gene indicates that the antibody decreases activity of the target membrane protein of interest.

65. The method of embodiment 64, wherein the reporter gene is a nutritional marker, antibiotic resistance marker, fluorescent marker, bioluminescent marker, or a counter-selectable marker.

66. The method of embodiment 65, further comprising performing positive selection for expression of the nutritional marker, wherein growth of the yeast host cells in a nutrient-deficient selection media indicates the target membrane protein of interest is activated.

67. The method of embodiment 66, wherein the nutritional marker is HIS3, HIS7, ARG6, LEU2, URA3, and TRP1.

68. The method of embodiment 65, further comprising performing positive selection for expression of the antibiotic resistance marker, wherein growth of the yeast host cells in a selection media comprising an antibiotic indicates the target membrane protein of interest is activated.

69. The method of embodiment 68, wherein the antibiotic resistance marker confers resistance to an antibiotic selected from the group consisting of geneticin, zeocin, hygromycin B, nourseothricin, and bialaphos.

70. The method of embodiment 65, further comprising performing positive selection for expression of the fluorescent marker, wherein detection of fluorescence emitted by the yeast host cells indicates the target membrane protein of interest is activated.

71. The method of embodiment 70, wherein the fluorescent marker is selected from the group consisting of a green fluorescent protein, a red fluorescent protein, a blue fluorescent protein, a cyan fluorescent protein, a yellow fluorescent protein, and an orange fluorescent protein.

72. The method of embodiment 65, further comprising performing positive selection for expression of the bioluminescent marker, wherein detection of bioluminescence emitted by the yeast host cells indicates the target membrane protein of interest is activated.

73. The method of embodiment 72, wherein the bioluminescent marker is luciferase or aequorin.

74. The method of embodiment 65, further comprising performing negative selection for expression of the counter-selectable marker, wherein decreases in activity of the target membrane protein of interest upon binding of the displayed antibody to the target membrane protein of interest are detectable by growth of the yeast host cells in a media comprising an agent that selects against cells expressing the counter-selectable marker.

75. The method of embodiment 74, wherein the counter-selectable marker is selected from the group consisting of CAN1, URA3, MET15, TRP1, and TK.

76. A method of screening the yeast periplasmic display library of embodiment 27 for an antibody that modulates the activity of the target GPCR of interest, the method comprising culturing at least a subset of the yeast host cells of the yeast periplasmic display library of embodiment 27 in a media, wherein detection of activation or inhibition of the pheromone response in at least one yeast host cell compared to a control yeast host cell not having an antibody displayed in the periplasmic space indicates that the displayed antibody in said at least one yeast host cell binds to and modulates the activity of the GPCR.

77. The method of embodiment 76, wherein the target GPCR of interest is a human GPCR.

78. The method of embodiment 77, further comprising contacting the human GPCR with a ligand.

79. The method of embodiment 78, wherein the GPCR has constitutive ligand-independent activity.

80. The method of any one of embodiments 76-79, wherein the yeast host cell is a FAR1 strain, wherein inhibition of the pheromone response by an antibody acting as an antagonist that binds to an inhibits the GPCR in the yeast host cell results in cessation of cell cycle arrest and growth of the yeast host cell.

81. The method of any one of embodiments 76-79, wherein the yeast host cell is a Δfar1 strain comprising a pheromone-inducible PRM1 promoter operably linked to a reporter gene, wherein activation of the pheromone response by an antibody acting as an agonist that binds to and activates the GPCR in the yeast host cell results in increased expression of the reporter gene.

82. The method of embodiment 73, wherein the reporter gene is a nutritional marker, antibiotic resistance marker, fluorescent marker, bioluminescent marker, or a counter-selectable marker.

83. The method of any one of embodiments 1-82, wherein the genus of the yeast host cells is selected from the group consisting of *Saccharomyces, Candida, Pichia, Kluyveromyces,* and *Yarrowia*.

84. The method of embodiment 83, wherein the genus of the yeast host cells is *Saccharomyces*.

85. The method of embodiment 84, wherein the species of the *Saccharomyces* is *Saccharomyces cerevisiae*.

86. A yeast host cell comprising:
   a) an antibody for display in the yeast host cell periplasmic space,
   b) a periplasm anchor protein, wherein the periplasm anchor protein is linked to the antibody such that the antibody is displayed in the periplasmic space; and
   c) a target membrane protein of interest, wherein the membrane protein of interest is located in the yeast host cell plasma membrane and accessible to the antibody displayed in the yeast host cell periplasmic space.

87. The yeast host cell of embodiment 86, wherein the antibody and the periplasm anchor protein are noncovalently linked together by molecular binding interactions in a complex or are linked by a covalent non-peptidic bond in a complex.

88. The yeast host cell of embodiment 86, wherein the antibody and the periplasm anchor protein are covalently linked together in a fusion protein.

89. The yeast host cell of any one of embodiments 86-88, wherein the periplasm anchor protein further comprises a signal sequence that directs transport of the periplasm anchor protein to the yeast host cell periplasm, plasma membrane, or cell wall such that the antibody is displayed in the periplasm.
90. The yeast host cell of any one of embodiments 86-88, wherein the periplasm anchor protein comprises a membrane-spanning transmembrane domain or a membrane associated protein domain that projects the antibody into the periplasm.
91. The yeast host cell of any one of embodiments 86-88, wherein the periplasm anchor protein is a protein that binds to an inner face of the cell wall such that the antibody is projected into the periplasm.
92. The yeast host cell of any one of embodiments 86-88, wherein the periplasm anchor protein is sufficiently large such that the periplasm anchor protein and linked antibody are retained in the periplasm.
93. The yeast host cell of any one of embodiments 86-92, wherein the target membrane protein of interest is selected from the group consisting of a receptor, an ion channel, and a transporter.
94. The yeast host cell of embodiment 93, wherein the receptor is a G-protein coupled receptor (GPCR).
95. The yeast host cell of any one of embodiments 86-94, further comprising introducing into the yeast host cell a recombinant polynucleotide encoding an engineered Gα subunit capable of being activated by the GPCR, wherein the activated engineered Gα subunit is capable of activating a detectable pheromone response in the yeast host cell.
96. The yeast host cell of embodiment 95, wherein the engineered Gα subunit is a chimeric G protein alpha (Gα) subunit comprising an N-terminal domain of a yeast Gα subunit and a C-terminal domain of an exogenous Gα subunit.
97. The yeast host cell of embodiment 96, wherein the yeast Gα subunit belongs to a Gαi, Gαq, Gαs, or Gαo family G protein.
98. The yeast host cell of embodiment 96 or 97, wherein the exogenous Gα subunit is a mammalian Gα subunit.
99. The yeast host cell of embodiment 98, wherein at least five C-terminal residues of the yeast Gα subunit are replaced with corresponding C-terminal residues of a mammalian Gα subunit such that the chimeric Gα subunit is capable of being activated by the mammalian GPCR.
100. The yeast host cell of embodiment 99, wherein at least 20 C-terminal residues of the yeast Gα subunit are replaced with corresponding C-terminal residues of the mammalian Gα subunit such that the chimeric Gα subunit is capable of being activated by the mammalian GPCR.
101. The yeast host cell of any one of embodiments 86-100, wherein the yeast host cell is a FAR1 strain for selection of antibody antagonists of the target GPCR of interest.
102. The yeast host cell of any one of embodiments 86-101, wherein the yeast host cell is a Δfar1 strain comprising a pheromone-inducible PRM1 promoter operably linked to a reporter gene for selection of antibody agonists of the GPCR.
103. The yeast host cell of any one of embodiments 86-101, wherein the genus of the yeast host cell is selected from the group consisting of *Saccharomyces, Candida, Pichia, Kluyveromyces*, and *Yarrowia*.
104. The yeast host cell of embodiment 103, wherein the genus of the yeast host cells is *Saccharomyces*.
105. The yeast host cell of embodiment 104, wherein the species of the *Saccharomyces* is *Saccharomyces cerevisiae*.
106. An antibody linked to a periplasm anchor protein.
107. The antibody of embodiment 106, wherein the antibody is localized to a yeast host cell periplasmic space.
108. The antibody of embodiment 106, wherein when the antibody is produced in a yeast host cell, the antibody is localized to the yeast host cell periplasmic space.
109. The antibody of any one of embodiments 106-108, wherein the antibody and the periplasm anchor protein are noncovalently linked together by molecular binding interactions in a complex or are linked by a covalent non-peptidic bond in a complex.
110. The antibody of any one of embodiments 106-108, wherein the antibody and the periplasm anchor protein are covalently linked together in a fusion protein.
111. The antibody of any one of embodiments 107-110, wherein the periplasm anchor protein further comprises a signal sequence that directs transport of the periplasm anchor protein to the yeast host cell periplasm, plasma membrane, or cell wall such that the antibody is displayed in the periplasm.
112. The antibody of any one of embodiments 107-110, wherein the periplasm anchor protein comprises a membrane-spanning transmembrane domain or a membrane associated protein domain that projects the antibody into the periplasm.
113. The antibody of embodiment 112, wherein the membrane associated protein domain is a glycosylphosphatidylinositol (GPI)-plasma membrane anchoring domain.
114. The antibody of any one of embodiments 107-110, wherein the periplasm anchor protein is a protein that binds to an inner face of the cell wall such that the antibody is projected into the periplasm.
115. The antibody of any one of embodiments 107-110, wherein the periplasm anchor protein is sufficiently large such that the periplasm anchor protein and linked antibody are retained in the periplasm.
116. The antibody of any one of embodiments 106-115, wherein the antibody is selected from the group consisting of a monoclonal antibody, a chimeric antibody, a humanized antibody, a nanobody, a recombinant fragment of an antibody, a Fab fragment, a Fab' fragment, a F(ab')$_2$ fragment, an F$_v$ fragment, and a scFv fragment.
117. The antibody of any one of embodiments 107-116, wherein the genus of the yeast host cell is selected from the group consisting of *Saccharomyces, Candida, Pichia, Kluyveromyces*, and *Yarrowia*.
118. The antibody of embodiment 117, wherein the genus of the yeast host cells is *Saccharomyces*.
119. The antibody of embodiment 118, wherein the species of the *Saccharomyces* is *Saccharomyces cerevisiae*.
120. A yeast host cell comprising the antibody of any one of embodiments 106-119.
121. A method of localizing an antibody to a yeast host cell periplasmic space comprising linking the antibody to a periplasm anchor protein such that the antibody is localized to the periplasmic space.
122. The method of embodiment 121, wherein the antibody and the periplasm anchor protein are noncovalently linked together by molecular binding interactions in a complex or are linked by a covalent non-peptidic bond in a complex.
123. The method of embodiment 122, wherein the antibody and the periplasm anchor protein are covalently linked together in a fusion protein.
124. The method of any one of embodiments 121-123, wherein the periplasm anchor protein further comprises a signal sequence that directs transport of the periplasm anchor protein to the yeast host cell periplasm, plasma membrane, or cell wall such that the antibody is displayed in the periplasm.

125. The method of any one of embodiments 121-123, wherein the periplasm anchor protein comprises a membrane-spanning transmembrane domain or a membrane associated protein domain that projects the antibody into the periplasm.

126. The method of embodiment 125, wherein the membrane associated protein domain is a glycosylphosphatidylinositol (GPI)-plasma membrane anchoring domain.

127. The method of any one of embodiments 121-123, wherein the periplasm anchor protein is a protein that binds to an inner face of the cell wall such that the antibody is projected into the periplasm.

128. The method of any one of embodiments 120-123, wherein the periplasm anchor protein is sufficiently large such that the periplasm anchor protein and linked antibody are retained in the periplasm.

129. The method of any one of embodiments 121-128, wherein the antibody is selected from the group consisting of a monoclonal antibody, a chimeric antibody, a humanized antibody, a nanobody, a recombinant fragment of an antibody, a Fab fragment, a Fab' fragment, a F(ab')$_2$ fragment, an F$_v$ fragment, and a scFv fragment.

130. The method of any one of embodiments 121-129, wherein the genus of the yeast host cell is selected from the group consisting of *Saccharomyces, Candida, Pichia, Kluyveromyces*, and *Yarrowia*.

131. The method of embodiment 130, wherein the genus of the yeast host cells is *Saccharomyces*.

132. The method of embodiment 131, wherein the species of the *Saccharomyces* is *Saccharomyces cerevisiae*.

133. A yeast periplasmic display library comprising a plurality of yeast host cells, wherein each yeast host cell comprises:
   a) an antibody for display in the yeast host cell periplasmic space, wherein the displayed antibody is different in each yeast host cell such that the plurality of yeast host cells displays a plurality of antibodies;
   b) a periplasm anchor protein, wherein the periplasm anchor protein is linked to the antibody such that the antibody is displayed in the periplasmic space; and
   c) a target membrane protein of interest, wherein the membrane protein of interest is located in the yeast host cell plasma membrane and accessible to the antibody displayed in the yeast host cell periplasmic space.

134. The yeast periplasmic display library of embodiment 133, wherein the antibody and the periplasm anchor protein are covalently linked together in a fusion protein.

135. The yeast periplasmic display library of embodiment 133, wherein the antibody and the periplasm anchor protein are noncovalently linked together by molecular binding interactions.

136. The yeast periplasmic display library of embodiment 133, further comprising a reporter system comprising a reporter gene operably linked to an inducible promoter that is activated when the target membrane protein of interest is activated to allow detection of increases or decreases in activity of the target membrane protein of interest upon binding of the antibody to the target membrane protein of interest.

137. The yeast periplasmic display library of embodiment 136, wherein the reporter gene is a nutritional marker, antibiotic resistance marker, fluorescent marker, bioluminescent marker, or counter-selectable marker.

138. The yeast periplasmic display library of embodiment 137, wherein the nutritional marker is selected from the group consisting of HIS3, HIS7, ARG6, LEU2, URA3, and TRP1.

139. The yeast periplasmic display library of embodiment 137, wherein the antibiotic resistance marker confers resistance to an antibiotic selected from the group consisting of geneticin, zeocin, hygromycin B, nourseothricin, and bialaphos.

140. The yeast periplasmic display library of embodiment 137, wherein the fluorescent marker is selected from the group consisting of a green fluorescent protein, a red fluorescent protein, a blue fluorescent protein, a cyan fluorescent protein, a yellow fluorescent protein, and an orange fluorescent protein.

141. The yeast periplasmic display library of embodiment 137, wherein the bioluminescent marker is luciferase or aequorin.

142. The yeast periplasmic display library of embodiment 137, wherein the counter-selectable marker is selected from the group consisting of CAN1, URA3, MET15, TRP1, and TK.

143. The yeast periplasmic display library of embodiment 136, wherein the reporter gene is a selectable marker such that said increases in activity of the target membrane protein of interest upon binding of the antibody to the target membrane protein of interest are detectable by growth of the yeast host cells on a positive selection media.

144. The yeast periplasmic display library of embodiment 136, wherein the reporter gene is a counter-selectable marker such that said decreases in activity of the target membrane protein of interest upon binding of the antibody to the target membrane protein of interest are detectable by growth of the yeast host cells on a negative selection media.

145. The yeast periplasmic display library of embodiment 133, wherein the target membrane protein of interest is selected from the group consisting of a receptor, an ion channel, and a transporter.

146. The yeast periplasmic display library of embodiment 145, wherein the receptor is a G-protein coupled receptor (GPCR).

147. The yeast periplasmic display library of embodiment 146, wherein the GPCR is an exogenous GPCR.

148. The yeast periplasmic display library of embodiment 147, further comprising an engineered Gα subunit capable of being activated by the exogenous GPCR, wherein the activated engineered Gα subunit is capable of activating a detectable pheromone response in the yeast host cell.

149. The yeast periplasmic display library of embodiment 148, wherein the engineered Gα subunit is a chimeric G protein alpha (Gα) subunit comprising an N-terminal domain of a yeast Gα subunit and a C-terminal domain of an exogenous Gα subunit.

150. The yeast periplasmic display library of embodiment 149, wherein the yeast Gα subunit belongs to a Gαi, Gαq, Gαs, or Gαo family G protein.

151. The yeast periplasmic display library of embodiment 149, wherein the exogenous GPCR is a mammalian GPCR.

152. The yeast periplasmic display library of embodiment 151, wherein at least five C-terminal residues of the yeast Gα subunit are replaced with corresponding C-terminal residues of a mammalian Gα subunit such that the chimeric Gα subunit is capable of being activated by the mammalian GPCR.

153. The yeast periplasmic display library of embodiment 152, wherein at least 20 C-terminal residues of the yeast Gα subunit are replaced with corresponding C-terminal residues of the mammalian Gα subunit such that the chimeric Gα subunit is capable of being activated by the mammalian GPCR.

154. The yeast periplasmic display library of embodiment 151, wherein the mammalian Gα subunit is selected from the group consisting of G alpha-S, G alpha-I, G alpha-O, G alpha-T, G alpha-Z, G alpha-Q, G alpha-11, G alpha-12, G alpha-13, and transducin.

155. The yeast periplasmic display library of embodiment 149, wherein the chimeric Gα subunit comprises at least 41 N-terminal residues of the yeast Gα subunit.

156. The yeast periplasmic display library of embodiment 151, wherein the mammalian GPCR is a human GPCR.

157. The yeast periplasmic display library of embodiment 156, wherein the human GPCR is selected from the group consisting of CXCR4, b2AR, CXCR2, CYSLTR2, KSHV vGPCR, PKR1, PKR2, CB2, A3AR, and AT1R.

158. The yeast periplasmic display library of embodiment 146, wherein the GPCR has constitutive ligand-independent activity.

159. The yeast periplasmic display library of embodiment 146, wherein the yeast host cell is a FAR1 strain for selection of antibody antagonists of the GPCR.

160. The yeast periplasmic display library of embodiment 146, wherein the yeast host cell is a Δfar1 strain comprising a pheromone-inducible PRM1 promoter operably linked to a reporter gene for selection of antibody agonists of the GPCR.

161. The yeast periplasmic display library of embodiment 133, wherein the antibodies are selected from the group consisting of monoclonal antibodies, chimeric antibodies, humanized antibodies, nanobodies, recombinant fragments of antibodies, Fab fragments, Fab' fragments, F(ab')$_2$ fragments, F$_v$ fragments, and scFv fragments.

162. The yeast periplasmic display library of embodiment 133, wherein the target membrane protein of interest comprises a mutation that increases or decreases its activity.

163. The yeast periplasmic display library of embodiment 133, wherein the yeast host cell is a Δfar1, Δsst2, Δste14, Δste3, or Δmat strain.

164. The yeast periplasmic display library of embodiment 163 wherein the Δmat strain comprises a deleted or inactivated MATα locus or a deleted or inactivated MATα locus.

165. The yeast periplasmic display library of embodiment 133, wherein the yeast host cell further comprises a modified CLN3 protein comprising a C-terminal truncation that increases abundance of CLN3 in the yeast host cell compared to a wild-type CLN3 protein.

166. The yeast periplasmic display library of embodiment 165, wherein the modified CLN3 protein retains at least N-terminal amino acids 1-387 of the wild-type CLN3 protein.

167. The yeast periplasmic display library of embodiment 166, wherein the modified CLN3 protein retains at least N-terminal amino acids 1-408 of the wild-type CLN3 protein.

168. The yeast periplasmic display library of embodiment 133, wherein the yeast host cell is a haploid or diploid yeast host cell.

169. The yeast periplasmic display library of embodiment 133, wherein the periplasm anchor protein further comprises a signal sequence that directs transport of the fusion protein to the yeast host cell periplasm, plasma membrane, or cell wall such that the fused protein variant is displayed in the periplasm.

170. The yeast periplasmic display library of embodiment 133, wherein the periplasm anchor protein comprises a membrane-spanning transmembrane domain or a membrane associated protein domain that projects the fused protein variant into the periplasm.

171. The yeast periplasmic display library of embodiment 170, wherein the membrane associated protein domain is a glycosylphosphatidylinositol (GPI)-plasma membrane anchoring domain.

172. The yeast periplasmic display library of embodiment 171, wherein the GPI-plasma membrane anchoring domain is a yapsin GPI plasma membrane anchoring domain.

173. The yeast periplasmic display library of embodiment 172, wherein the yapsin GPI plasma membrane anchoring domain is a YPS1, YPS2, YPS3, YPS4, YPS5, YPS6, or YPS7 yapsin GPI plasma membrane anchoring domain.

174. The yeast periplasmic display library of embodiment 133, wherein the periplasm anchor protein is a protein that binds to an inner face of the cell wall such that the displayed protein variant is projected into the periplasm.

175. The yeast periplasmic display library of embodiment 133, wherein the periplasm anchor protein is sufficiently large that the fusion protein is retained in the periplasm, 176. A method of making the yeast periplasmic display library of embodiment 134, the method comprising:
   a) providing a plurality of recombinant polynucleotides encoding fusion proteins, wherein each recombinant polynucleotide encodes a different fusion protein comprising the periplasm anchor protein linked to a different antibody for display;
   b) transfecting the plurality of yeast host cells with the plurality of recombinant polynucleotides encoding the fusion proteins;
   c) transfecting the plurality of yeast host cells with a recombinant polynucleotide encoding the target membrane protein of interest; and
   d) culturing the plurality of yeast host cells under conditions that permit expression of the fusion proteins and the target membrane protein of interest, wherein each yeast host cell displays a different antibody in the periplasmic space and the target membrane protein of interest localizes to the plasma membrane, such that the yeast periplasmic display library of embodiment 134 is produced.

177. The method of embodiment 176, wherein the recombinant polynucleotides encoding the fusion proteins or the recombinant polynucleotide encoding the target membrane protein of interest are provided by expression vectors.

178. The method of embodiment 176, wherein the recombinant polynucleotides encoding the fusion proteins or the target membrane protein of interest are integrated into the yeast host cell genome at a target locus.

179. The method of embodiment 176, wherein the target membrane protein of interest is selected from the group consisting of a receptor, an ion channel, and a transporter.

180. The method of embodiment 179, wherein the receptor is a G-protein coupled receptor (GPCR).

181. The method of embodiment 180, further comprising introducing into the plurality of yeast host cells a recombinant polynucleotide encoding an engineered Gα subunit capable of being activated by the GPCR, wherein the activated engineered Gα subunit is capable of activating a detectable pheromone response in the yeast host cell.

182. The method of embodiment 181, wherein the engineered Gα subunit is a chimeric G protein alpha (Gα) subunit comprising an N-terminal domain of a yeast Gα subunit and a C-terminal domain of an exogenous Gα subunit.

183. The method of embodiment 182, wherein the yeast Gα subunit belongs to a Gαi, Gαq, Gαs, or Gαo family G protein.

184. The method of embodiment 182, wherein the exogenous Gα subunit is a mammalian Gα subunit.

185. The method of embodiment 184, wherein at least five C-terminal residues of the yeast Gα subunit are replaced with corresponding C-terminal residues of a mammalian Gα subunit such that the chimeric Gα subunit is capable of being activated by the mammalian GPCR.

186. The method of embodiment 185, wherein at least 20 C-terminal residues of the yeast Gα subunit are replaced with corresponding C-terminal residues of the mammalian Gα subunit such that the chimeric Gα subunit is capable of being activated by the mammalian GPCR.

187. The method of embodiment 181, wherein the yeast host cell is a FAR1 strain for selection of antibody antagonists of the target GPCR of interest.

188. The method of embodiment 181, wherein the yeast host cell is a Δfar1 strain comprising a pheromone-inducible PRM1 promoter operably linked to a reporter gene for selection of antibody agonists of the GPCR.

189. A method of screening the yeast periplasmic display library of embodiment 136 for an antibody that modulates activity of the target membrane protein of interest, the method comprising culturing at least a subset of the yeast host cells of the yeast periplasmic display library of embodiment 136 in a selection media; and detecting expression of the reporter gene, wherein increased expression of the reporter gene indicates that the antibody increases activity of target membrane protein of interest and decreased expression of the reporter gene indicates that the antibody decreases activity of the target membrane protein of interest.

190. The method of embodiment 189, wherein the reporter gene is a nutritional marker, antibiotic resistance marker, fluorescent marker, bioluminescent marker, or a counter-selectable marker.

191. The method of embodiment 190, further comprising performing positive selection for expression of the nutritional marker, wherein growth of the yeast host cells in a nutrient-deficient selection media indicates the target membrane protein of interest is activated.

192. The method of embodiment 191, wherein the nutritional marker is HIS3, HIS7, ARG6, LEU2, URA3, and TRP1.

193. The method of embodiment 190, further comprising performing positive selection for expression of the antibiotic resistance marker, wherein growth of the yeast host cells in a selection media comprising an antibiotic indicates the target membrane protein of interest is activated.

194. The method of embodiment 193, wherein the antibiotic resistance marker confers resistance to an antibiotic selected from the group consisting of geneticin, zeocin, hygromycin B, nourseothricin, and bialaphos.

195. The method of embodiment 190, further comprising performing positive selection for expression of the fluorescent marker, wherein detection of fluorescence emitted by the yeast host cells indicates the target membrane protein of interest is activated.

196. The method of embodiment 195, wherein the fluorescent marker is selected from the group consisting of a green fluorescent protein, a red fluorescent protein, a blue fluorescent protein, a cyan fluorescent protein, a yellow fluorescent protein, and an orange fluorescent protein.

197. The method of embodiment 190, further comprising performing positive selection for expression of the bioluminescent marker, wherein detection of bioluminescence emitted by the yeast host cells indicates the target membrane protein of interest is activated.

198. The method of embodiment 197, wherein the bioluminescent marker is luciferase or aequorin.

199. The method of embodiment 190, further comprising performing negative selection for expression of the counter-selectable marker, wherein decreases in activity of the target membrane protein of interest upon binding of the displayed antibody to the target membrane protein of interest are detectable by growth of the yeast host cells in a media comprising an agent that selects against cells expressing the counter-selectable marker.

200. The method of embodiment 199, wherein the counter-selectable marker is selected from the group consisting of CAN1, URA3, MET15, TRP1, and TK.

201. A method of screening the yeast periplasmic display library of embodiment 148 for an antibody that modulates the activity of the target GPCR of interest, the method comprising culturing at least a subset of the yeast host cells of the yeast periplasmic display library of embodiment 148 in a media, wherein detection of activation or inhibition of the pheromone response in at least one yeast host cell compared to a control yeast host cell not having an antibody displayed in the periplasmic space indicates that the displayed antibody in said at least one yeast host cell binds to and modulates the activity of the GPCR.

202. The method of embodiment 201, further comprising contacting the human GPCR with a ligand.

203. The method of embodiment 201, wherein the GPCR has constitutive ligand-independent activity.

204. The method of embodiment 201, wherein the yeast host cell is a FAR1 strain, wherein inhibition of the pheromone response by an antibody acting as an antagonist that binds to an inhibits the GPCR in the yeast host cell results in cessation of cell cycle arrest and growth of the yeast host cell.

205. The method of embodiment 201, wherein the yeast host cell is a Δfar1 strain comprising a pheromone-inducible PRM1 promoter operably linked to a reporter gene, wherein activation of the pheromone response by an antibody acting as an agonist that binds to and activates the GPCR in the yeast host cell results in increased expression of the reporter gene.

206. The method of embodiment 205, wherein the reporter gene is a nutritional marker, antibiotic resistance marker, fluorescent marker, bioluminescent marker, or a counter-selectable marker.

IV. EXPERIMENTAL

The invention will be more fully understood by reference to the following examples of specific embodiments for carrying out the present invention. The examples are offered for illustrative purposes only, and are not intended to limit the scope of the present invention in any way. Various modifications or changes in light thereof will be suggested to persons skilled in the art and are to be included within the spirit and purview of this application and scope of the appended claims.

Efforts have been made to ensure accuracy with respect to numbers used (e.g., amounts, temperatures, etc.), but some experimental error and deviation should, of course, be allowed for.

Example 1

Yeast Display for Selection of Antibodies that Modulate GPCR Function

Overview

A plethora of therapeutic targets in such diseases as cancer and inflammation involve G-protein coupled receptors (GPCRs). However, many GPCRs with the greatest therapeutic potential for high-impact diseases are difficult to drug. Although small molecules affecting GPCR function are easily found, they are often non-specific due to structural similarity between GPCR ligand-binding pockets, potentially causing significant off-target side effects. Unlike small molecules, antibodies and related affinity molecules (e.g., nanobodies and ScFvs and Fabs), are an appealing therapeutic class due to their potentially superior specificity, functional diversity, and pharmacological properties. Additionally, antibodies can better interact with extracellular domains and loops, which can modulate the structure (and thus function) of GPCRs in more sophisticated ways than small molecules. However, there is to date not a single approved GPCR antibody therapeutic in the United States, and only one worldwide, in Japan.

Current yeast or phage display workflows identify antibodies that tightly bind but often do not affect the function of GPCRs. The antigens used are often GPCR fragments that do not represent the functional GPCR accessible to the antibody in vivo, or are heterogeneously structured full-length protein preparations. The workflow also overlooks a tremendous fraction of total functional diversity, because most antibodies are never functionally assayed. What is needed is a high-throughput platform to directly select for antibodies that modulate GPCR function.

However, it is much less straightforward to develop antibodies that alter the function of GPCRs (Jo 2015, Hutchings 2010). This is due primarily to the following issues with many current solutions: 1) The antigens used are lacking. Antigens derived from extracellular GPCR peptides or fragments may be good for developing antibodies for Western blots, but do not structurally represent therapeutically relevant targets. Further, homogenously, functionally folded full-length protein in lipids or detergents can be hard to prepare in sufficient amounts for immunization, phage display, or yeast display. 2) Antibodies selected for their high affinity are mostly non-functional; they bind to regions in the GPCR that do not affect function. 3) Workflows lose significant antibody diversity—and therefore functionality—in selected antibodies. By first selecting for antibodies that bind tightly and discarding the rest, huge amounts of functional diversity are lost. Mammalian cell systems have been created to functionally screen antibody candidate subsets in an autocrine fashion (Zhang 2014), which partially addresses issue 2, but due to transformation efficiencies ($\sim 10^4$) and limited engineerability of selectable/screenable readouts, they are limited to screens of small subsets of candidates.

Our innovation includes combining GPCR-to-yeast pheromone response coupling and expressing affinity molecules that act in cis in the same cell in a high-throughput platform. This enables direct and high-throughput functional selection of affinity molecules (FIG. 1). To do this, we combine two strategies that are optimal for yeast:
1. Functional Expression of a Human GPCR, Coupled to Yeast Pheromone Response Readouts Yeast are the system of choice for expressing full length, functional GPCRs from humans for in vitro biochemical and structural studies. Remarkably, yeast have also been used successfully to functionally couple human GPCRs to the yeast pheromone response pathway and, depending on the readout, screen/select for small molecule, peptide, or protein ligands that functionally interact with a GPCR (King 1990, Brown 2000, Erlenbach 2001, Minic 2005, Dowell 2009, Dong 2010, Liu 2016). The most "universal" method of coupling is to modify the yeast Gα subunit, Gpa1, to bind to a human GPCR and transduce signals by transplanting the 5 C-terminal residues of the cognate human Gα to replace the native 5 C-terminal amino acids in Gpa1 to make a "Gα transplant" (Conklin 1993, Brown 2000, Erlenbach 2001). Other methods include complete replacement of Gpa1 with the full-length cognate Gα of the human receptor (King 1990), or construction of a more complex Gpa1/Gα chimera, with different portions of each combined into a hybrid human/yeast Gα (Klein 1998, Price 1995).

2. Yeast Display of Affinity Molecules—Antibodies, Nanobodies, and ScFvs

There is also substantial knowledge about expressing and secreting affinity molecules like IgGs, ScFvs, Fabs, and nanobodies in yeast (Horwitz 1988, Hamilton 2006, Jeong 2011). Multiple antibody clinical candidates were developed by yeast display-based companies like Adimab. Many academic labs and companies have refined methods to express these molecules and "display" them on yeast by fusing the affinity molecules to proteins that are covalently attached to the extracellular surface of the cell wall, e.g., Aga1 and Aga2 (Boder 1997, Bidlingmaier 2015). Libraries of complexities of $10^9$ have been routinely developed in yeast, which is sufficient for normal binding studies and more than adequate for our functional selection platform (for reasons described in FIG. 1).

In addition, we endeavored to tether secreted affinity molecules not to the cell wall facing outward, as in the case of conventional yeast display, but rather tethered to the extracellular face of the cell membrane. In this way, the affinity molecule can functionally interact in cis with GPCRs in the membrane. We tested four different domains, and determined GPI-anchoring domain of YPS1 (Frieman 2003) to be the best, based on assessing membrane fluorescence of cells expressing GFP fusions to the tested domains.

Example 2

Low-Background Yeast Strain

We created a yeast strain that, when treated with a GPCR ligand, does not grow, and is not prone to frequently occurring mutations that would allow growth. We aimed for a $10^{-7}$ background/false positive rate.

Haploid yeast of mating type "a" ("MATa" cells) undergo cell cycle arrest when the mating pheromone, alpha factor (a factor) activates its cognate GPCR receptor Ste2. This growth-arrest phenotype can be used in selection of Ste2 antagonists. Unfortunately, spontaneous "pheromone resistant" mutants arise at a staggering rate. The background or "false positive" rate in our parental haploid strain is $\sim 10^{-4}$, i.e., ~100 colonies grow when $10^6$ cells are spread in α-factor plates. To reduce the background, we engineered a pheromone-responsive diploid base strain (Herskowitz 1989). False positives caused by loss-of-function mutations appear much less frequently in diploids. However, normal diploid yeast carry both MATα and MATalpha genes; a/alpha cells do not express Ste2 nor respond to pheromones. We constructed a diploid that behaves like a MATα haploid by deleting the entire MATalpha locus from its genome. The MATa/Δmatalpha diploid had a ~100-fold lower background rate.

Almost none of the "false positives" in the diploid strain responded to pheromone at all. Presumably, they carried gain-of-function mutations that inactivated the signaling cascade. We thus developed a selectable marker that is only active in cells with a functioning pheromone response pathway. This marker depends on the pathway's basal level of signaling for its expression—this signaling does not require pheromone or the pheromone receptor and is instead dependent on stochastic "baseline" activation of the cognate G-protein (Hagen 1991; Oehlen 1995). This low basal signaling is not enough to trigger cell cycle arrest; that response requires activation of the GPCR Ste2 by α-factor. Some constitutively-expressed yeast genes depend on the basal activity of the pheromone response pathway to be expressed. We constructed our selectable marker by placing the promoter of one such gene, MFA1, driving the expression of HIS3, a gene required for cells to synthesize its own histidine. (Daniel 2006). The P(MFA1)-HIS3 construct confers growth to cells in media lacking histidine (H-media) only if they can signal from the G-proteins down to the pheromone response transcription factor Ste12. The engineered diploid strain (NIY326) carrying P(MFA1)-HIS3 and plated in H-media with α-factor had a background rate of $10^{-7}$.

TABLE 1

Summary of strain development to reduce background rate. Background is colonies formed per $10^7$ cells plated on pheromone-containing agar

| Strain | Background rate |
|---|---|
| Parent haploid | $10^{-4}$ |
| Engineered diploid | $10^{-6}$ |
| Engineered diploid + pathway function confirmation cassette | $10^{-7}$ |

Example 3

Construction of a Periplasm-Localized Nanobody Library

We constructed a set of periplasm-targeting expression vectors driving expression of a chimera with an N-terminal secretion signal, MFalpha PrePro (Brake 1984), followed by an 18-amino-acid linker containing a single FLAG epitope (DYKDDDDK) and ending in the YPS1 glycophosphatidylinositol (GPI) anchoring domain. The PrePro signal targets the protein for translocation into the endoplasmic reticulum and secretion, and is later cleaved off, while processing of the YPS1 GPI domain in the ER results in an N-terminal GPI anchor that retains the chimera tethered to the plasma membrane (Frieman 2003). Restriction sites immediately after the MFalphaPrePro coding sequence allow cloning of affinity molecules (e.g., for creation of a nanobody cDNA library). The vectors carry the selectable marker URA3, which allows for positive selection in uracil-deficient media and also for counterselection (see below).

Figure 4A:
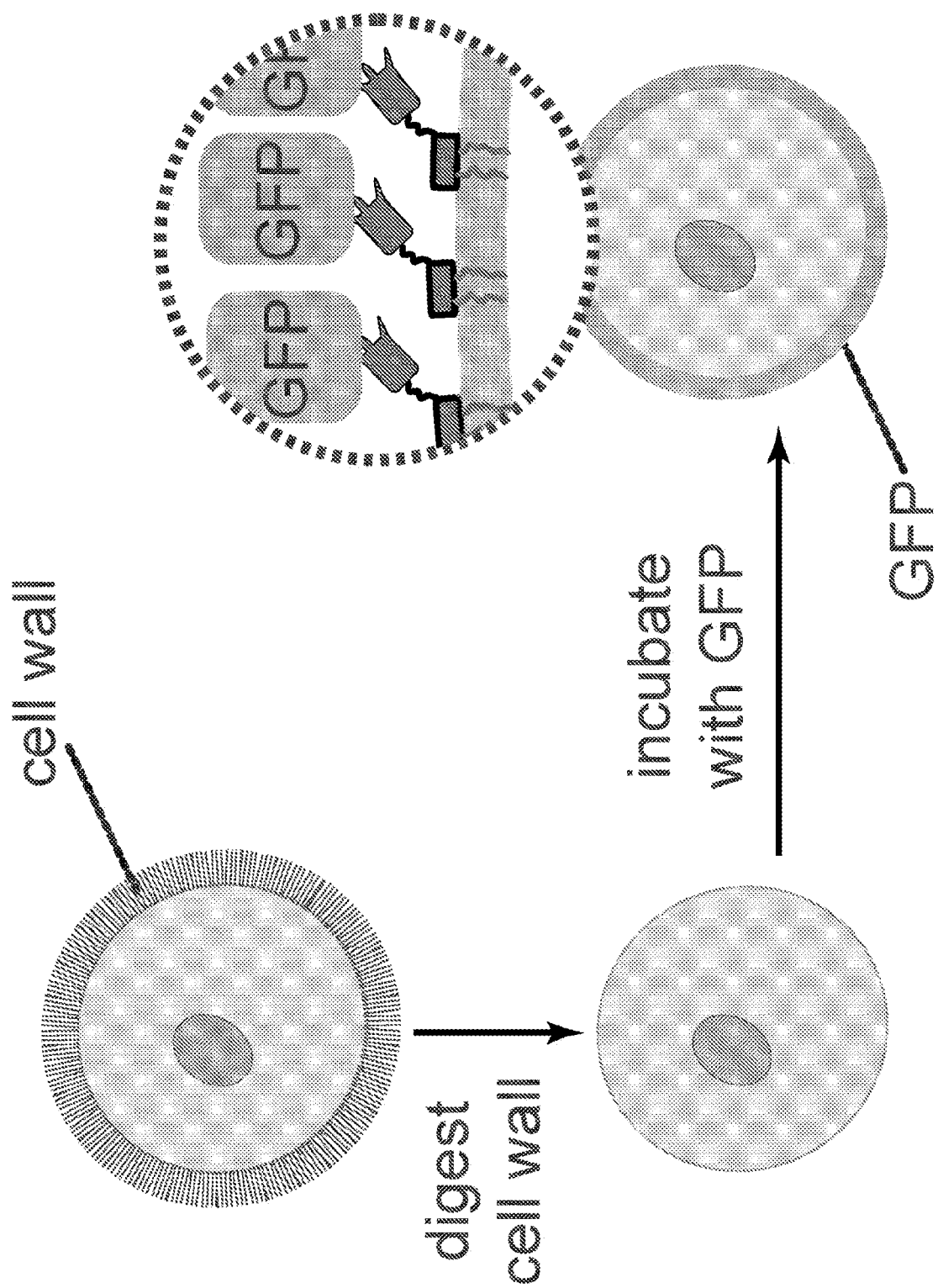
FIGS. 4A and 4B show verification of affinity molecule expression/targeting vector.
Figure 4B:
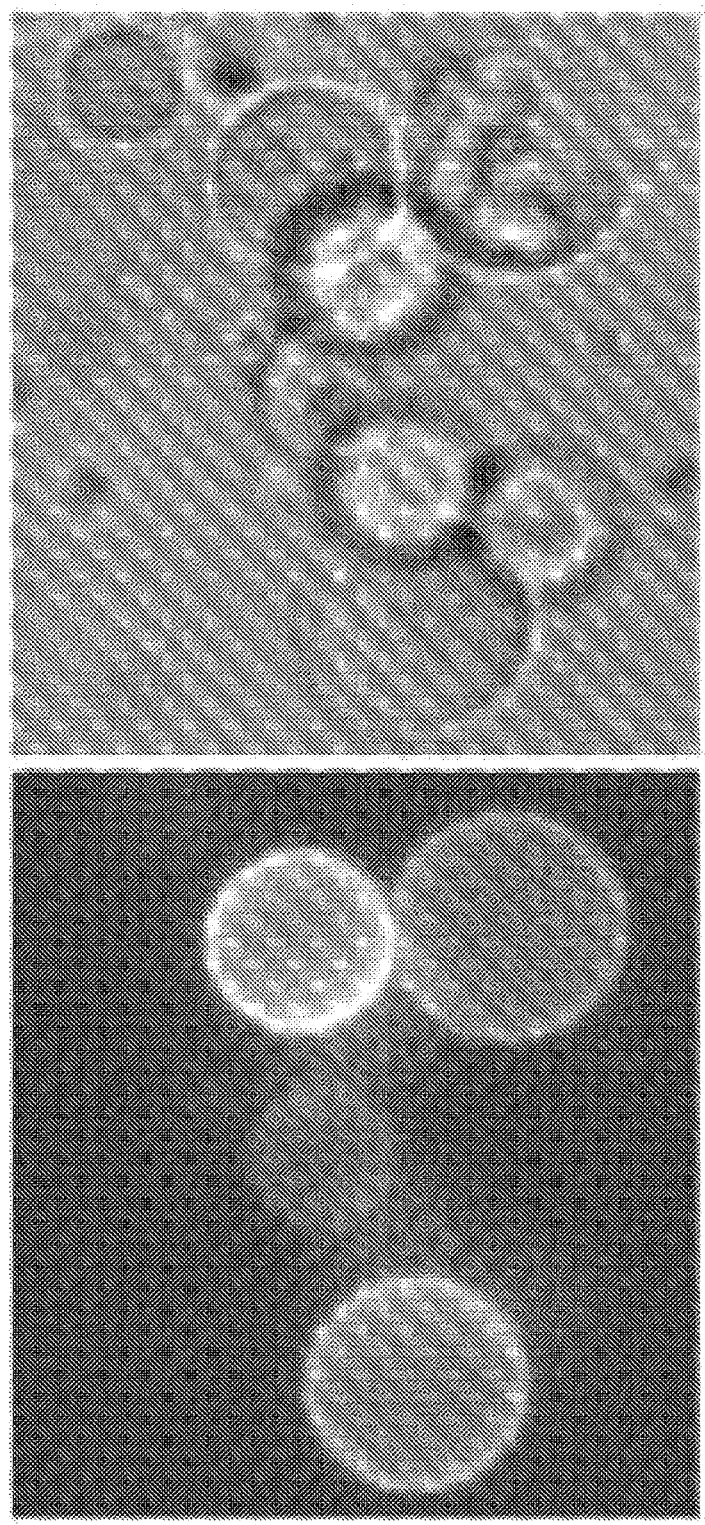

We confirmed that these expression vectors localized a nanobody to the extracellular face of the membrane by cloning an anti-GFP nanobody (Kirchhoffer 2009). When we digested the cell walls of these cells and applied GFP extracellularly, we observed green fluorescence coinciding with their cell membranes (FIG. 4), which confirmed the periplasmic localization of the anti-GFP nanobody.

We next constructed a nanobody library. We used as a source, a library of nanobodies with a $10^6$ clone titer, previously cloned in an E. coli vector (Salema 2013). We amplified the nanobody coding sequences by PCR, and cloned them into a plasma-membrane targeting vector by yeast homologous recombination, using the low background platform strain NIY326 (van Leeuwen 2015). We obtained ~$1 \times 10^6$ independent colonies on uracil and histidine deficient (U-/H-) agar media. We scraped the colonies with cryogenic storage media and stored the slurry in aliquots at −80° C. (Library 001).

Example 4

Selection of Nanobodies that Act as Ste2 Autocrine Antagonists

Figure 5A:
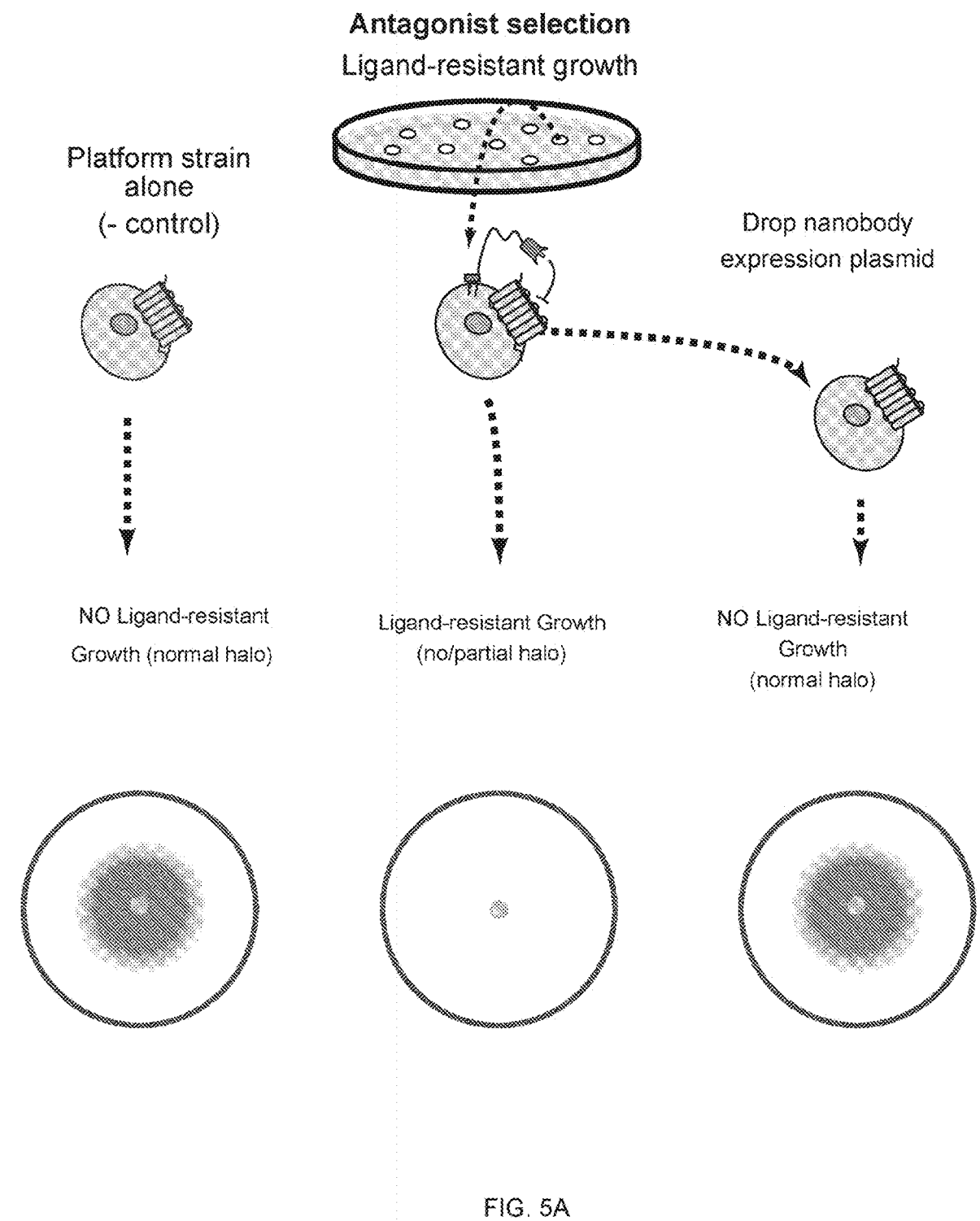
FIGS. 5A and 5B show verification of the plasmid dependence of alpha factor resistant clones.
Figure 5B:
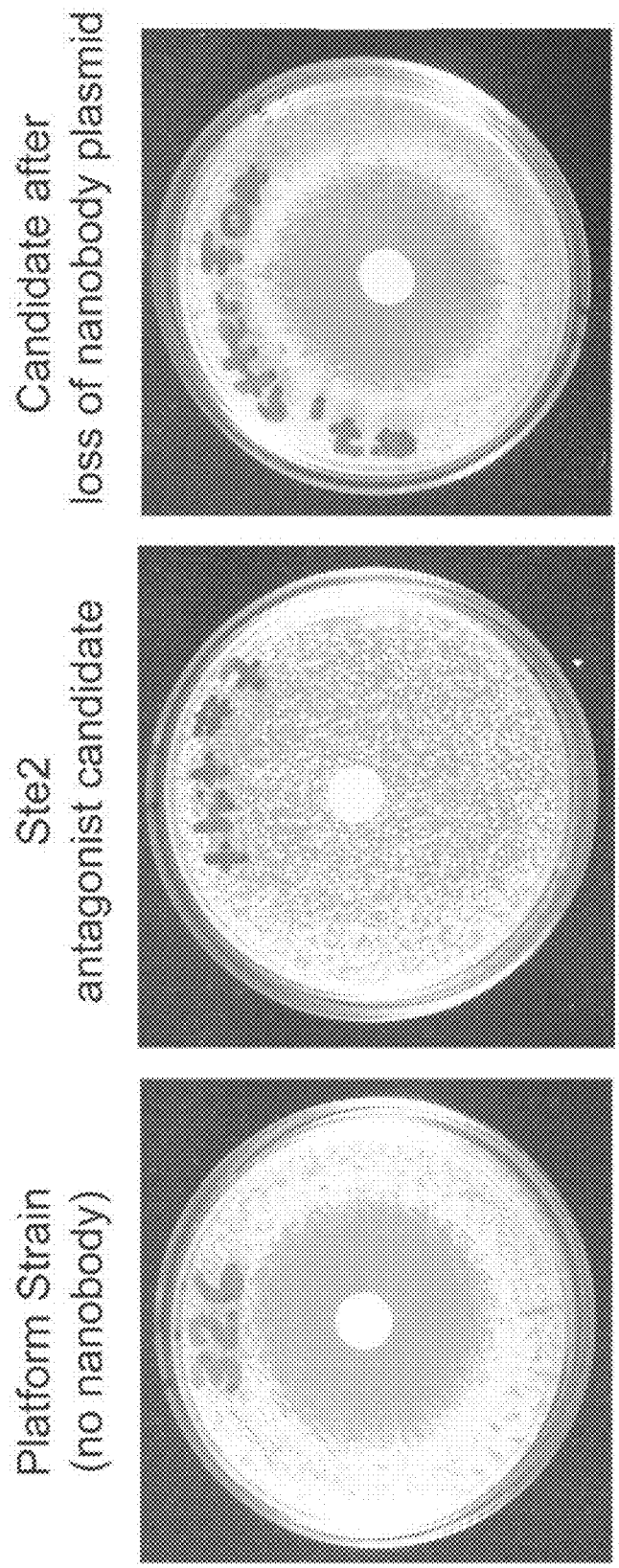
Figure 6:
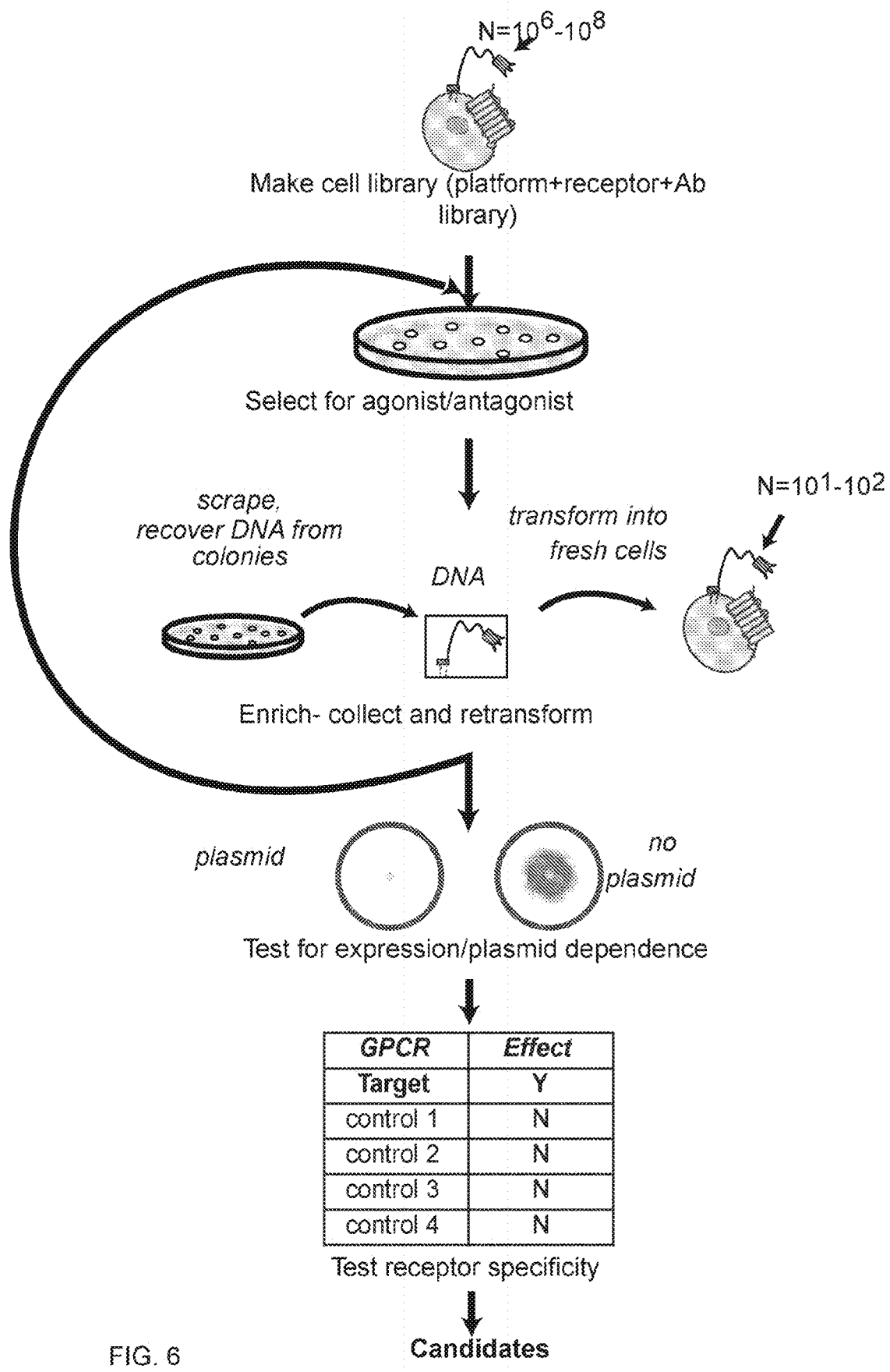
FIG. 6 shows a workflow schematic.

A. Selection of Pheromone-Resistant Clones from Nanobody Library:

We selected for pheromone-resistant clones from the Library 001 described in Example 3. We plated $10^8$ cells onto several U-/H-plates with α-factor and incubated them for 5 days. We analyzed a random sample of 90 colonies out of approximately 300 that grew. We next determined if their ability to grow on α-factor was plasmid-dependent. We selected clones that had lost the plasmid spontaneously by plating them onto media containing 5-FOA, which is toxic to cells expressing URA3. We then tested clones that grew before 5-FOA selection, but did not grow afterward. We performed halo assays and found that 12 clones out of 90 initially isolated lost their ability to grow on α-factor-containing agar media after 5-FOA selection in halo assays (FIG. 5).

B. Specificity and Site of Action Tests:

To test whether the candidate nanobody affinity molecules are specific (i.e., require the target receptor Ste2 to block the pheromone response), we express the candidates in a MATalpha strain. MATalpha cells express the a-factor receptor Ste3 and do not express Ste2. Ste3 is a GPCR only distantly related to Ste2, and its ligand, the a-factor pheromone, is a glycosylated peptide entirely different from α-factor. For both, the pheromone signaling cascades of MATα and MATalpha downstream of the receptor are identical. Both MATα and MATalpha cells arrest their cell cycle and activate pheromone-inducible genes in response to their cognate pheromone. Our MATα and MATalpha tester cells carry a pheromone-inducible transcriptional reporter, P(PRM1)-YFP that can be used to test pathway function in the absence and presence of the antagonist candidates. We thus assess specificity by comparing the effect of the antagonist candidates by measuring cell cycle arrest and induction of YFP in MATα and MATalpha cells exposed to their cognate pheromones. We advance candidates if they act as antagonists solely in the MATα (Ste2) strain.

C. Assess Site of Action by Applying Purified Nanobody Extracellularly

Though unlikely, GPCR antagonism could result from intracellular binding and disruption of Ste2 localization to the plasma membrane. Since any "binder" antibody could potentially act in this way, we are testing the ability of the candidates to modulate GPCR function when added exogenously.

We express and purify the nanobody proteins, apply them to cells in the presence of pheromone, and use growth in pheromone and reporter induction assays to measure their effect on Ste2 (and Ste3) function. We express the candidates in bacteria with a C-terminal 6×His tag, using vector pET28b and BL21(DE3) cells, and purify them using non-denaturing 6His affinity purification (Bornhorst 2000). Due to their small size (15 kDa), nanobodies are able to diffuse through the yeast cell wall (Ries 2012). In addition to this functional test, we label the recombinant nanobodies with a fluorescent dye (Alexa 488, compatible with GFP wavelengths; Kit #A20181, Thermo-Fisher Scientific) and test their ability to stain the plasma membrane of Ste2-expressing cells and not control Ste3-expressing cells. The immunofluorescence experiments also allow us to compare the staining of fixed cells with and without their cell walls (which can be easily removed with a lyticase enzymatic treatment), and thus confirm that the nanobodies can diffuse effectively through the cell wall. Finally, immunofluorescence is used to confirm that antagonist candidates directly bind the receptor rather than the ligand to exert their effects.

Example 5

Agonist Selection Strains

We construct agonist selection strains that require Ste2 stimulation to grow. In a version of our platform strain lacking the P(MFA1)-HIS3 marker, we disable the pheromone-induced cell cycle arrest function by deleting both genomic copies of FAR1 using a CRISPR-Cas9 approach (Horwitz 2015). Next, we replace the PRM1 open reading frame in one of the PRM1 alleles in this diploid strain with a HIS3 ORF, creating a P(PRM1)-HIS3 selectable-marker. We have incorporated P(PRM1)-HIS3 in other strains and observed no significant "leakiness", i.e., these cells grow on H-plates only in the presence of α-factor. We create MATα and MATα versions of this strain for the specificity tests. As expected, the false positive rate of P(PRM1)-HIS3 strains is much lower than for the antagonist selection strain because mutations that turn on the pheromone cascade are rarer than those that turn it off (Brown 2000). In case we observe an abundance of weak "growers" in H-plates when plating cells expressing the nanobody library, we are using the minimal, empirically determined concentration of the His3 inhibitor 3-aminotriazole that blocks their growth due to leakiness of HIS3 expression (a standard strategy for yeast HIS3 selection applications).

Similar to the antagonist screens, we select yeast clones expressing candidate agonist nanobodies for Ste2 based on growth in H-plates. We test whether growth is plasmid/expression dependent and confirm specificity by testing hits in the Ste3 agonist selection strain (using the P(PRM1)-HIS3 and P(PRM1)-YFP reporter). Also, as above, we produce the nanobodies in bacteria and add them directly to cells to test their effectiveness.

Example 6

Coupling Human GPCRs to the Yeast Pheromone Pathway

A. Gpa1-Transplant Panel

A widely used method for coupling human GPCRs to the yeast pheromone pathway is to modify the yeast Gα, Gpa1, such that its 5 C-terminal amino acids are changed to those of a human Gα, generating a "GPA1 transplant" (Brown 2000, Erlenbach 2001). For each receptor, the suitable Gα is often found empirically (Dowell 2009). In most cases, coupling is achieved with transplants for either Gαi, Gαq, Gαs or Gαo (Dong 2010). Using a CRISPR approach (Horwitz 2015), we are creating a panel of diploid agonist and antagonist GPA1-transplant strains for these 4 Gα transplant strains.

B. Test Human GPCRs in our System

In most cases, human GPCRs express best in yeast from a genome-integrated construct driven by a moderate promoter like P(ACT1) (Shiroishi 2012, Schutz 2016). Often, the well-expressed GPCRs are chimeras with an N-terminal cleavable secretory signal (typically the MFalpha PrePro), followed by a FLAG epitope tag for immunodetection, and sometimes a C-terminal GFP. We have constructed vectors with these features, and can be modified easily on a case-by-case basis. We clone the receptors in Table 2 into these vectors and test their expression level and plasma membrane localization by fluorescence microscopy and/or anti-FLAG immunofluorescence.

We transform the transplant strains with the GPCR-expressing constructs. For each GPCR, and test the strength of their coupling to the pheromone response using the P(PRM1)-HIS3 and P(PRM1)-YFP reporters in the agonist selection strain.

TABLE 2

Candidate human therapeutic GPCR targets for coupling and antagonist/agonist discovery

| Target | Indication | Collaborator | Selection Type | Ligand/ Constitutive mutant | Yeast | Nb/ScFv |
|---|---|---|---|---|---|---|
| CXCR4 | Cancer (11, 40), inflammation (72) | Handel (29), Gutkind (76) | Antagonist | SDF-1 cytokine, small molecule agonist (79), and constitutive mutant (79) | (73) | (36, 40) |
| b2AR | Asthma (48), COPD (2) | Kobilka (66) | Agonist | N/A (agonist selection) | (17) | (45, 54) |
| CXCR2 | Immuno-oncology (75, 37) | Handel (18), Gutkind (24) | Antagonist | IL-8 cytokine, constitutive mutant (53) | (53) | |
| CYSLTR2 | Oncology (70) | Gutkind (35) | Antagonist | N/A (constitutively active) (70) | | |

TABLE 2-continued

Candidate human therapeutic GPCR targets for coupling and antagonist/agonist discovery

| Target | Indication | Collaborator | Selection Type | Ligand/ Constitutive mutant | Yeast | Nb/ScFv |
|---|---|---|---|---|---|---|
| KSHV VGPCR | Oncology (9) | Gutkind (47) | Antagonist | N/A (constitutively active) (3) | | |
| PKR1 | Oncology/ Angiogenesis (33) | Ferrara (63) | Antagonist | EG-VEGF, BV8, peptide (50, 10) | | |
| PKR2 | Oncology/ Angiogenesis (33) | Ferrara | Antagonist | EG-VEGF, BV8 (50) | | |
| CB2 | Immune suppression (57), RA (25), IBD/Crohn's (44) | | Agonist | N/A (agonist selection) | | |
| A3AR | RA (22), asthma (58), psoriasis (78) | | Agonist | N/A (agonist selection) | | |
| AT1R | Cardiac disease (68), diabetes (68) | | Antagonist | Angiotensin II, small molecule (27) | (51) | |

Example 7

Screening for Antibodies that Modulate GPCR Function

A. Submit Selected GPCRs to Antibody Selection Process

We follow an approach similar to our previous work with Ste2, except for the following. We are using a diversified human ScFv library (guaranteed $10^8$-$10^9$ diversity, Oak Biosciences). We clone this library in the same affinity molecule vector as before, expressing the ScFvs in the plasma membrane as YPS1 GPI-anchored chimeras. For antagonist selection, signaling from the coupled receptors is not expected to be strong enough to trigger cell cycle arrest. We therefore are using a P(FUS2)-CAN1 counter-selectable marker (Erlenbach 2001). P(FUS2) is a pheromone inducible promoter, like P(PRM1). CAN1 encodes a plasma membrane transporter for arginine and also for the toxic arginine-analog canavanine. Cells carrying P(FUS2)-CAN1 cannot grow in canavanine plates if they carry an activated human GPCR coupled to the pheromone response. This phenotype enables us to select for antagonistic antibodies for human GPCRs in canavanine plates. For agonist selection, we use the P(PRM1)-HIS3 marker as before. After selecting candidates, as above, we isolate plasmid-free derivatives of these clones to test the plasmid-dependency of their pheromone-blocking phenotypes.

B. Test Specificity and Site of Action of Candidate Antibodies

1) Test on other GPCRs

We validate the specificity of the plasmid-dependent candidates by transforming the plasmids in strains expressing other receptors. In this case, we test them on the MATα (Ste2) and MATα (Ste3) strains as well as in strains expressing at least 2 other human GPCRs coupled to the pheromone response via a GPA1 transplant (i.e., to check that the agonist or antagonist does not act on other GPCRs).

2) Test by Applying Purified Nanobody Protein Extracellularly

While nanobodies (15 kDa) can diffuse through the yeast cell wall (Ries 2012), larger ScFvs (27 kDa) might be significantly constrained. We perform immunofluorescence with labeled candidate ScFvs in yeast, with and without digesting the cell wall.

Example 8

Testing the Impact of Anti-CB2 VHH Domain Agonist Presentation on Growth Rate

Figure 7:
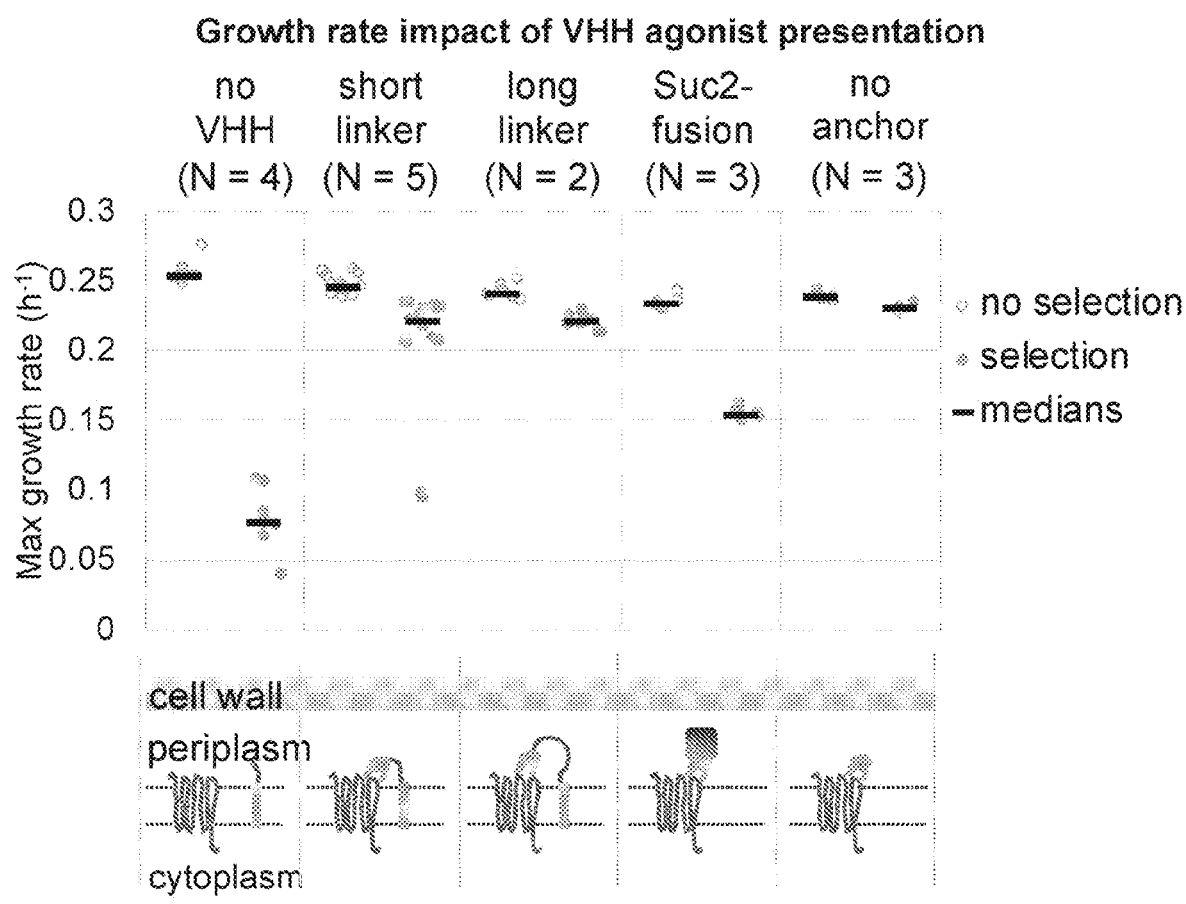
FIG. 7 shows the impact on growth rate of yeast cells by activation of the cannabinoid receptor type 2 (CB2 receptor) using VHH domain agonists displayed in the periplasmic space in various ways.

To determine the effect of agonist presentation on growth rate of yeast cells, we constructed yeast strains expressing a human GPCR protein, the human cannabinoid receptor type 2 (CB2 receptor), and transformed them with either empty plasmid (no VHH) or with agonist expression plasmids in which the single-domain VHH antibody Ab101 is presented in different ways. We tested four different agonist VHH expression plasmids in which the VHH domain is presented by 1) a short linker connected to a Yps1 plasma membrane anchor 2) a long linker connected to a Yps1 plasma membrane anchor 3) an N-terminal fusion connected to the soluble periplasmid enzyme Suc2 and 4) direct secretion of untagged VHH into the periplasm. From two to five independent clones were grown to saturation in the absence of selection. Saturated cells were used to start cultures with technical duplicates in a 96-well microtiter plate for automated absorbance measurements (OD630) in a plate reader. Two culture media formulations were used. The first culture media formulation requires no expression from the pheromone response reporter (no selection). The second culture media formulation was the same as the first, but lacks one amino acid that can be produced only as a result of pheromone response reporter expression (selection). Absorbance measurements were taken every five minutes for 48 hours. For each technical replicate, a max growth rate was extracted from raw absorbance measurements computationally. All data generated were graphed, and the median growth rate is indicated by a horizonal bar (FIG. 7). The cartoons below the graph depict each presentation modality (FIG. 7).

Each of the four agonist VHH expression plasmids increased the growth rate in the second culture media formulation compared to cells transformed with empty plasmid (no VHH). This demonstrates that various ways of presenting the agonist in the periplasm can be used to activate the activity of the GPCR protein CB2 receptor. In particular, we demonstrated that the CB2 receptor can be activated by VHH domain antibodies that are covalently connected to a plasma membrane anchor protein, whether through a long or a short linker. We also demonstrated that functional VHH domain agonist antibodies can be localized to the periplasm by fusing the antibody to a periplasmic protein, Suc2, that is sufficiently large such that the fusion protein is retained in the periplasm. Suc2 forms oligomers comprising multiple Suc2 proteins linked by non-covalent interactions and this multimerization is required for retention of Suc2 in the periplasm. Therefore, this condition also demonstrates retention in the periplasm partly through non-covalent interactions between the antibody and the anchor protein. Finally, this experiment demonstrates that direct secretion of untagged VHH domain antibodies into the periplasm can activate the CB2 receptor.

Although preferred embodiments of the subject invention have been described in some detail, it is understood that obvious variations can be made without departing from the spirit and the scope of the invention as described herein.

What is claimed is:

1. A yeast periplasmic display library comprising a plurality of yeast host cells, wherein each yeast host cell comprises:
    a) an antibody for display in the yeast host cell periplasmic space, wherein the displayed antibody is different in each yeast host cell such that the plurality of yeast host cells displays a plurality of antibodies;
    b) a periplasm anchor protein, wherein the periplasm anchor protein is linked to the antibody such that the antibody is displayed in the periplasmic space; and
    c) a target membrane protein of interest, wherein the membrane protein of interest is located in the yeast host cell plasma membrane and accessible to the antibody displayed in the yeast host cell periplasmic space;
    d) a reporter system comprising a reporter gene operably linked to an inducible promoter that is activated when the target membrane protein of interest is activated to allow detection of increases or decreases in activity of the target membrane protein of interest upon binding of the antibody to the target membrane protein of interest, wherein the reporter gene is a nutritional marker, antibiotic resistance marker, or a counter-selectable marker.

2. The yeast periplasmic display library of claim 1, wherein the antibody and the periplasm anchor protein are covalently linked together in a fusion protein.

3. The yeast periplasmic display library of claim 1, wherein the periplasm anchor protein further comprises a signal sequence that directs transport of the periplasm anchor protein to the yeast host cell periplasm, plasma membrane, or cell wall such that the antibody is displayed in the periplasm.

4. The yeast periplasmic display library of claim 1, wherein the periplasm anchor protein comprises a membrane-spanning transmembrane domain or a membrane associated protein domain that projects the antibody into the periplasm.

5. The yeast periplasmic display library of claim 1, wherein the periplasm anchor protein is a protein that binds to an inner face of the cell wall such that the antibody is projected into the periplasm.

6. The yeast periplasmic display library of claim 2, wherein the periplasm anchor protein is a protein that binds to an inner face of the cell wall that projects the fusion protein into the periplasm.

7. The yeast periplasmic display library of claim 1, wherein the target membrane protein of interest is selected from the group consisting of a receptor, an ion channel, and a transporter.

8. The yeast periplasmic display library of claim 7, wherein the receptor is a G-protein coupled receptor (GPCR).

9. The yeast periplasmic display library of claim 8, wherein the GPCR is an exogenous GPCR.

10. The yeast periplasmic display library of claim 9, further comprising an engineered Ga subunit capable of being activated by the exogenous GPCR, wherein the activated engineered Ga subunit is capable of activating a detectable pheromone response in the yeast host cell.

11. The yeast periplasmic display library of claim 1, wherein the antibodies are selected from the group consisting of monoclonal antibodies, chimeric antibodies, humanized antibodies, nanobodies, recombinant fragments of antibodies, Fab fragments, Fab' fragments, F(ab')$_2$ fragments, F$_v$ fragments, and scFv fragments.

12. The yeast periplasmic display library of claim 1, wherein the genus of the yeast host cells is selected from the group consisting of *Saccharomyces*, *Candida*, *Pichia*, *Kluyveromyces*, and *Yarrowia*.

* * * * *